(12) United States Patent
Enomura

(10) Patent No.: US 8,623,415 B2
(45) Date of Patent: Jan. 7, 2014

(54) METHOD FOR PRODUCING BIOLOGICALLY INGESTIBLE MICROPARTICLES, BIOLOGICALLY INGESTIBLE MICROPARTICLES, AND DISPERSION AND PHARMACEUTICAL COMPOSITION CONTAINING THE SAME

(75) Inventor: Masakazu Enomura, Izumi (JP)

(73) Assignee: M. Technique Co., Ltd., Osaka (JP)

( * ) Notice: Subject to any disclaimer, the term of this patent is extended or adjusted under 35 U.S.C. 154(b) by 171 days.

(21) Appl. No.: 12/668,021

(22) PCT Filed: Jul. 4, 2008

(86) PCT No.: PCT/JP2008/062234
§ 371 (c)(1),
(2), (4) Date: Feb. 1, 2010

(87) PCT Pub. No.: WO2009/008391
PCT Pub. Date: Jan. 15, 2009

(65) Prior Publication Data
US 2010/0322997 A1    Dec. 23, 2010

(30) Foreign Application Priority Data

| Jul. 6, 2007 | (JP) | 2007-179098 |
| Jul. 6, 2007 | (JP) | 2007-179102 |
| Jul. 6, 2007 | (JP) | 2007-179104 |
| Jul. 9, 2007 | (JP) | 2007-180349 |
| Aug. 6, 2007 | (JP) | 2007-203850 |
| Aug. 21, 2007 | (JP) | 2007-214821 |

(51) Int. Cl.
*A61K 9/14* (2006.01)
*B01J 13/00* (2006.01)
*B01J 19/06* (2006.01)

(52) U.S. Cl.
USPC ............... 424/489; 422/224; 977/895

(58) Field of Classification Search
None
See application file for complete search history.

(56) References Cited

U.S. PATENT DOCUMENTS

| 2004/0028582 A1 | 2/2004 | Carpenter et al. | |
| 2004/0032792 A1* | 2/2004 | Enomura | 366/263 |
| 2004/0191319 A1 | 9/2004 | Yun et al. | |
| 2004/0241430 A1* | 12/2004 | Jachuck et al. | 428/330 |
| 2006/0147535 A1 | 7/2006 | Muthukumaran et al. | |
| 2006/0286015 A1* | 12/2006 | Holl | 422/224 |

FOREIGN PATENT DOCUMENTS

| EP | 1371610 A1 | 12/2003 |
| JP | 57-42308 A | 3/1982 |
| JP | 4-295420 A | 10/1992 |
| JP | 6-227967 A | 8/1994 |
| JP | 7-277729 A | 10/1995 |
| JP | 2002-538227 A | 11/2002 |
| JP | 2003-159696 A | 6/2003 |
| JP | 2003-210957 A | 7/2003 |
| JP | 2004-49957 | 2/2004 |
| JP | 2004-154635 A | 6/2004 |
| JP | 2004-174297 A | 6/2004 |
| JP | 2005-270745 A | 10/2005 |
| JP | 2006-028108 A | 2/2006 |
| JP | 2006-089386 A | 4/2006 |
| JP | 2006-104193 A | 4/2006 |
| JP | 2006-341232 A | 12/2006 |
| JP | 2007-077061 A | 3/2007 |
| JP | 2007-230957 A | 9/2007 |
| WO | WO 03/033097 A2 | 4/2003 |
| WO | WO 2006/120945 A1 | 11/2006 |

OTHER PUBLICATIONS

Oxley et al. (Evaluation of spinning disk reactor technology for the manufacture of pharmaceuticals, 39 Ind. Eng. Chem. Res. 2175 (2000)).*
Oxley (Evaluation of spinning disk reactor technology for the manufacture of pharmaceuticals, 39 Ind. Eng. Chem. Res. 2175 (2000).*
Rasenack et al., "Dissolution Rate Enhancement by in Situ Micronization of Poorly Water-Soluble Drugs," Pharmaceutical Research, vol. 19, No. 12, Dec. 2002, pp. 1894-1900, XP008021339.
Rasenack et al., "Preparation of microcrystals by in situ microzation," Powder Technology, vols. 143-144, 2004 (available online: Jun. 17, 2004), pp. 291-296, XP055039215.
Steckel et al., "In-situ-micronization of disodium cromoglycate for pulmonary delivery," European Journal of Phamaceutics and Biophamaceutics, vol. 55, 2003, pp. 173-180, XP004414205.

* cited by examiner

*Primary Examiner* — Robert A Wax
*Assistant Examiner* — H. Sarah Park
(74) *Attorney, Agent, or Firm* — Birch, Stewart, Kolasch & Birch, LLP

(57) ABSTRACT

A method of separating biologically ingestible microparticles is used to obtain biologically ingestible microparticles in a thin film fluid formed between two processing formed by a fluid to be processed containing at least a first solvent in which an objective substance to be pulverized is dissolved and a second solvent in which the solubility of the microparticles is lower than in the first solvent. The biologically ingestible microparticles are separated by a neutralization reaction in the thin film fluid.

17 Claims, 29 Drawing Sheets

FIG. 1 (A)
FIG. 1 (B)
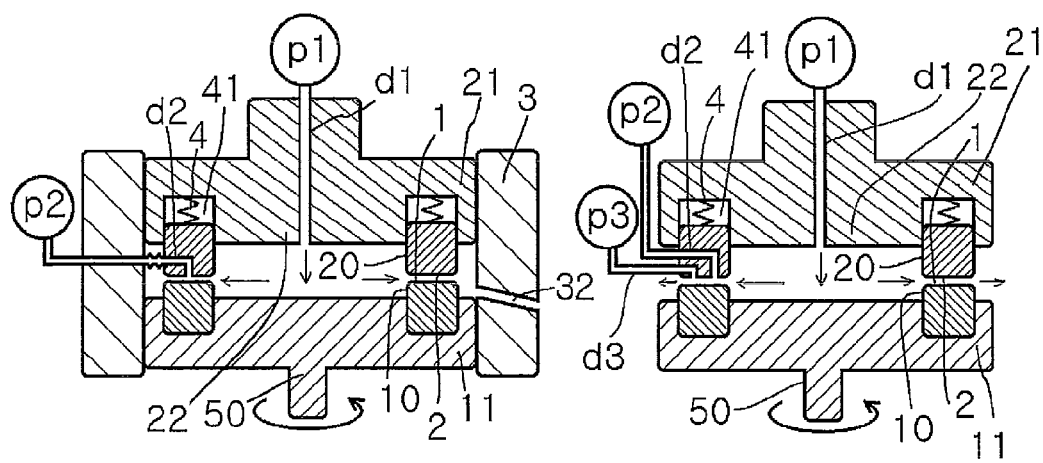
FIG. 1 (C)
FIG. 1 (D)
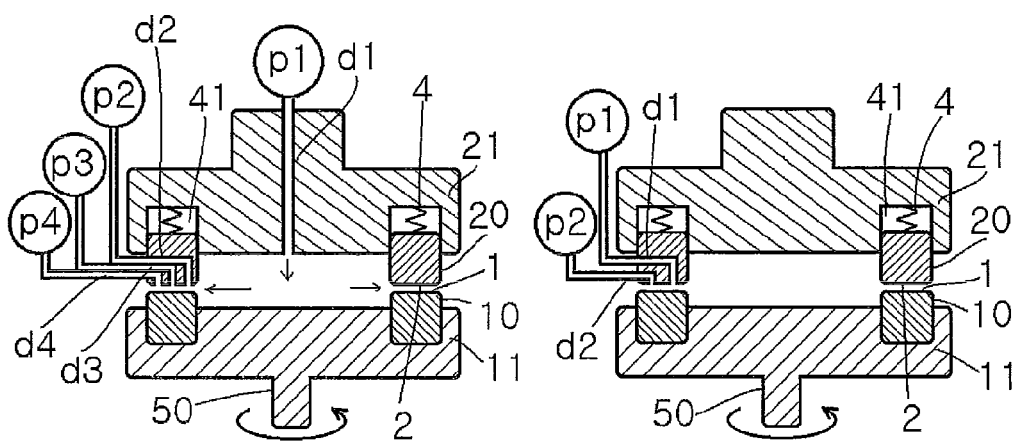

FIG. 2 (A)
FIG. 2 (B)
FIG. 2 (C)
FIG. 2 (D)
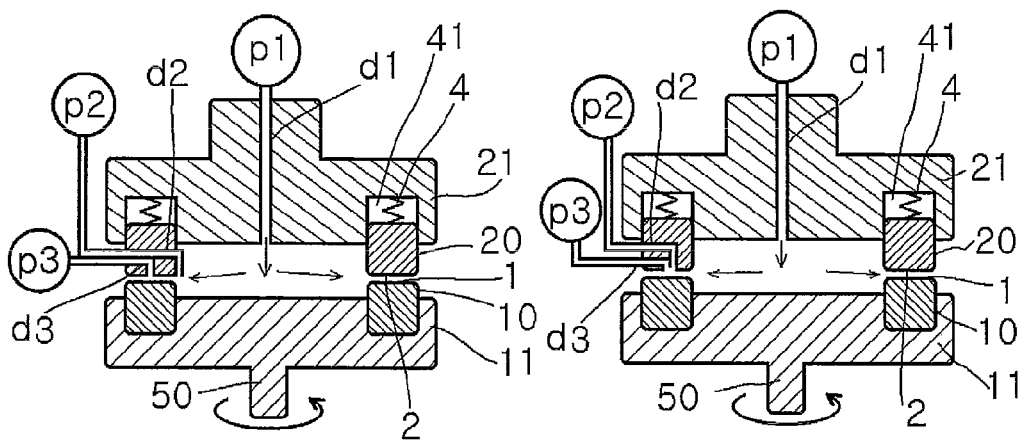
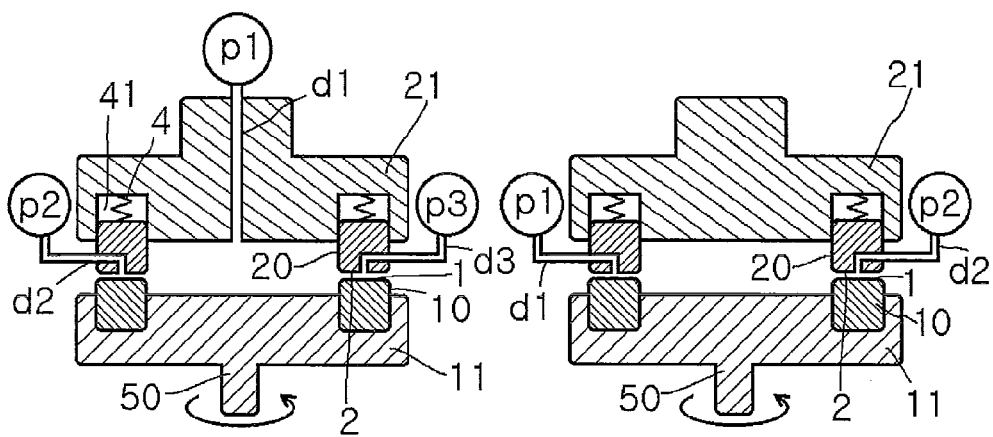

METHOD FOR PRODUCING BIOLOGICALLY INGESTIBLE MICROPARTICLES, BIOLOGICALLY INGESTIBLE MICROPARTICLES, AND DISPERSION AND PHARMACEUTICAL COMPOSITION CONTAINING THE SAME

TECHNICAL FIELD

The present invention relates to a method for producing biologically ingestible microparticles, wherein the microparticles excellent in redispersibility can be formed easily and uniformly in a large amount with high energy efficiency. The present invention also relates to biologically ingestible microparticles produced by the production method, as well as a dispersion and a pharmaceutical composition containing the same.

BACKGROUND ART

Patent Document 1: JP-A H04-295420
Patent Document 2: JP-A 2006-104193
Patent Document 3: JP-A H07-277729
Patent Document 4: JP-A 2005-270745
Patent Document 5: JP-A 2003-159696
Patent Document 6: JP-A 2003-210957
Patent Document 7: JP-A H06-227967
Patent Document 8: JP-A 2007-77061
Non-Patent Document 1: "Nanotechnology Handbook, Part I, Creation", first edition, first print, 2003, published by Ohmsha Ltd. (Kandanishiki-cho 3-1, Chiyoda-ku, Tokyo, JP)

The nanotechnology attracts a great deal of attention as a scientific technology raising a new industrial revolution. Because a conventional substance can exhibit new functions by converting the substance into microparticles, the conversion of the substance into nanoparticles is an important theme in the whole industrial world, and the interest in the technology of conversion into nanoparticles is extremely increasing for advance of the nanotechnology. (Non-Patent Document 1) (Non-Patent Document 1)

Particularly with respect to substances intended to be ingested by the living body (biologically ingestible substances), such as foods, food additives, cosmetics and pharmaceutical preparations for drugs and medicines, microparticulation technology draws increasing attention, and particularly the microparticulation of drugs and medicines in pharmaceutical preparations is known to bring about improvements in solubility, that is, significant improvements in the degree of biological absorption, and is increasingly expected.

On the other hand, a long time for development and depletion of possible substances become problematic in creation of a new possible substance for drugs and medicines, and one of such causes is that the possible compound is poorly water-soluble so that a change in the structure of the compound may be necessary and thus the development may be increasingly delayed or deadlocked. Because possible compounds selected to be developed are low in solubility, there is also a problem that not only formulation of drugs and medicines but a toxicity test and evaluation of their dynamics cannot be advanced. However, some compounds are highly membrane-permeable even being low in solubility in water, and can be sufficiently absorbed after oral administration, so that when compounds are dropped in view of solubility only, promising compounds may be also left out. Accordingly, there is a desire to develop formulating technology for improving solubility and consequently for improving the degree of absorption into the living body.

It is reported that, in many cases, even a poorly water-soluble drug, when finely atomized, increases its surface area and increases the rate of dissolution, thereby increasing absorption into the living body. For example, the biological availability (BA) of an anti-endometriosis drug danazol was 5.1% when its commercial product (average particle diameter: 10 µm) was administered to a dog in the form of a suspension, while the BA of danazol was significantly increased to 82.3% when the drug was administered in the form of a nano-suspension having an average particle diameter of 169 nm (Int J. Pharm. 125, 1995, 91-97). When an anti-inflammatory agent naproxen was administered to a rat, its absorption was increased four times as much by atomizing its bulk powder of 20 to 30 µm into powder of 270 nm (Int J. Pharm 125, 1995, 309-313). Accordingly, when a poorly water-soluble drug can be formed successfully into nanoparticles, the absorptivity of the drug can be significantly improved.

Under this background, manufacturing technologies of atomizing (nano atomization) a drug have been desired, and for industrial application of such technologies, the establishment of a production method capable of stable mass production is one of the most important tasks in the application of nanotechnology to pharmaceuticals.

Generally, as a method for producing microparticles, there are: a break-down method (crushing method) of mechanically crushing and atomizing a bulk-state material to obtain microparticles; and a bottom-up method (developing method) of aggregating atoms and molecules thereby developing them into microparticles of suitable size.

As a crushing method, included are a mechanical crushing style of using a mill such as a ball mill, an attritor mill, a vibrator mill, a sand mill, a roller mill or a Cowles-type mixer, and another style of radiating femtosecond laser to solid particles such as a laser ablation. In the case of the mechanical crushing style, however, there is a fundamental limit to the degree of atomization by crushing, and there are problems of, for example, mix of impurities and lack of purity in products, since use of a crushing force generated by contacting a medium mill inevitably causes mix of broken particles of bead itself. Further, enormous energy is required, so that at present there is also a problem in energy costs. The laser ablation method is a process of utilizing a crushing force by strong light, and thus the possibility of photodecomposition at the molecular level cannot be denied. The substantial amount of production under the present situation is about 0.1 mg/h and cannot be said to be at an industrially practicable level.

Further, microparticles produced by the crushing method generate active sites easily on their fracture surfaces as a result of physical crushing, so that the crushed microparticles are aggregated again to easily form coarser aggregates than before crushing. Accordingly, the utility value of the product may be deteriorated, or anomalies such as increase of viscosity in the dispersion system as a whole may be caused, so that there are many problems in the crushing methods themselves.

Patent Document 1 describes a method of obtaining drug microparticles, specifically a method of obtaining particles of less than 250 nm by means of a mill such as a ball mill, an attritor mill, a vibrator mill, a sand mill, a roller mill or a Cowles-type mixer. As for mix of foreign materials due to, for example, abrasion of media, it is merely referred to therein as not causing unacceptable contamination, and a risk of mix of foreign materials may arise a critical problem for pharmaceutical preparations in which high qualities always are required.

Next, the bottom-up method used as a method of preparing microparticles is a method utilizing various reaction means such as chemical reaction, crystallization and sublimation, wherein a reaction is used in combination with a polymer dispersing method, a thermal decomposition method, a supercritical method or a sonication method, thereby aggregating atoms and molecules to form microparticles.

As reaction means, a reaction method using a batch reaction container as described in Patent Document 3 or a gaseous phase method using plasma in a high vacuum as described in Patent Document 4 is used in some cases. Further, a microreactor and a micro-flow path reactor as described in Patent Documents 5 and 6 is utilized in some cases.

In a batch system, controlling temperature in the batch is generally difficult, and so is conducting a uniform reaction. Further, the control of concentration in a completely uniform state is not feasible, and thus the control of reaction conditions is difficult. Moreover, the reaction time should be prolonged, and thus a uniform reaction hardly proceeds under the control of all reaction conditions.

In a gaseous phase method, the amount of nanoparticles formed per unit time is small, and a high-energy apparatus to evaporate materials is necessary, such as an electron beam, plasma, a laser and induction heating. Further, the yield is low, so a gaseous phase method cannot be said to be very suitable for mass production in view of production costs. Furthermore, it is a problem that the nanoparticles obtained by a gaseous phase method are readily aggregated and fused together while a size of the particles varies, since the particles are microparticles of a pure substance.

It has been attempted to use a microreactor or a micromixer known in microchemical processing in a method for producing the biologically ingestible minute microparticles described above. However, when the microparticles are produced by these methods, the methods are not applicable to all the reactions, since the micro-flow path is closed with high possibility by clogging of the flow path with bubbles and byproducts generated by the reaction, and the reactions are allowed to proceed fundamentally by molecular diffusion only. The microchemical process uses a scale-up method of increasing the number of reactors arranged in parallel, but a problem is that because the manufacturing ability of one reactor is small, and scaling up in a large volume is not practical, and the respective reactors are difficult to be supplied with the same performance, thus failing to provide uniform products. When the reaction solution is highly viscous or the reaction causes increasing viscosity, very high pressure is necessary for passing of the solution through a minute flow path, so it concerns that a usable pump is limited, and leakage of the solution from an apparatus cannot cease due to the high pressure.

Particularly in the case of pharmaceutical preparations, high qualities are definitely required. Strongly desired are physicochemical qualities such as a crystal form or a crystal particle size, and basic qualities of having mixing of impurities and, further, insoluble microparticles, in the pharmaceutical preparations, so superb technologies of production meeting such requirements for qualities are required. However, substances produced in the chemical industry and produced as foods and pharmaceutical preparations often contain aggregates of fine crystals, and those with a mother liquid and impurities in crystals. Also, when atomization is done with a crushing device using media, mix of a media-derived foreign material is inevitable. From now on, consciousness of environmental issues and saving of resources and energy is necessary, thus including this, there are many problems to be resolved. Further in the process for producing biologically ingestible microparticles, mix of a foreign material and growth of bacteria in the process may cause a problem too, so the proposal of a production method capable of providing biologically ingestible microparticles in a safer and more inexpensive way by reducing production time is required.

Some poorly water-soluble drugs are soluble not only in organic solvents but also in acidic or alkaline solutions, but many of the drugs are known to be poor in stability of compounds in aqueous solutions in which they have been dissolved. For example, pirenoxine is hydrolyzed when dissolved in an aqueous solution of pH 6 or higher. Accordingly, many of pirenoxine eye drops commercially available should, just before use, be dissolved in an attached solvent and be prepared.

An aqueous suspension having a poorly water-soluble drug suspended therein is known too. However, the diameter of drug particles in aqueous suspended eye drops commercially available is several μm to several dozen μm, and thus these aqueous suspended eye drops are hardly subjected to filtering sterilization. For assuring the sterility of the preparations, it is necessary that sterilization such as final high-pressure steam sterilization or dry heat sterilization of the main raw material be done, and the whole of the production process thereafter be conducted by an aseptic operation. However, it is known that, when the final high-pressure steam sterilization is conducted, in a state from large to small particles mixed in it, small particles dissolve and disappear, while larger particles further grow (Ostwald ripening). In a sterilizing operation involving intense changes of the temperature, the particles further become coarser and coarser. During sterilization, a surface modifier/particle-solving agent is separated, which is accompanied by coarsened particles, and thus it is difficult to maintain dispersibility (JP-A H06-227967/Patent Document 7). When the dry heat sterilization of the main raw material is conducted, the thermal denaturation, adhesion and strong aggregation of the main raw material are caused, and thus mechanical crushing and dispersion treatment for a longer time are necessary, and as a result, an aseptic operation for a long time is required. In the case of the production method involving such aseptic operations, it costs for the aseptic facilities and operations, and aspects of production such as workability and of quality assurance such as maintenance of asepsis matter.

As an aqueous suspension of pirenoxine, a method capable of filtering sterilization and providing eye drops is shown in which pirenoxine is ultrafinely atomized by mechanical crushing to provide inexpensive eye drops (JP-A 2007-77061/Patent Document 8). However, the conventional mechanical production method requires a long time in atomization and suffers from problems such as productivity and increasing burden of costs due to high processing energy and complexity of the process. Further, many of atomizing machines use media, which indicates mix of media as foreign material and difficulty in acquisition of uniform particles and easy aggregation. It is also noted that coarse particles act as cores to promote aggregation.

Meanwhile, the fact that atomization of pirenoxine can improve osmotic properties to corneas and, in the form of an aqueous suspension, improving stability to light is known, and the same effect can be expected for other eye drops.

In the method for atomizing a pharmaceutical composition, particularly in the case of a poorly water-soluble drug, there is a method of improving solubility such as a pH regulating method, an organic solvent method, a micelle method, a complex method, a microemulsion method, and a microparticulation method. The methods other than the microparticulation method depend on physical properties of individual drugs and are thus not always applicable to every drug. The microparticulation method of crushing by a mechanical means can be applied widely to drugs, but there are problems such as easy aggregation, difficulty in acquisition of uniform particles, and mix of impurities in the crushing process.

The method of atomizing a drug includes a dry crushing method, a wet crushing method, a crystallization method, and so on. Generally, a pharmaceutical preparation is heat-labile, so that in the dry crushing method, there are problems due to heat generation during crushing process such as conversion into an amorphous compound, and occurrence of dust. The wet crushing method also suffers from problems such as a long processing time, and difficulty in regulating the diameter of attained particles. Further, use of media inevitably causes mix of a foreign material attributable to abrasion of the media, and the mixed foreign material is difficult to be isolated, thus making the resulting particles unusable in products requiring high purity.

In most cases, it takes long time for the wet crushing as described above to process, so that bacteria may grow over the time. In addition, a great burden of costs out of high processing energy and complexity of the process is concerned.

The method for producing drug microparticles includes a method of dissolving a compound in a solvent and then mixing the solution with a new solvent to separate crystals, and a method of dissolving a compound in a solvent by pH regulation and then changing the pH with an acid or an alkali to separate crystals. In such reaction methods, two liquids have been mixed usually by means of a dynamic mixing apparatus having a movable part in its mixing area, for example, a stirring and mixing apparatus having an impeller. It should be careful when such a mixing apparatus is used to process a compound having an extremely high rate of crystal growth. If it takes a long time to mix a solution of such a compound with a new solvent, separation of crystals is initiated in its solution in a state of nonuniform concentration, then particles having broad particle size distribution/particle diameter distribution, and coarse particles, depending on growth of crystals, are mixed, resulting in not obtaining the objective crystals having sharp particle size distribution/particle diameter distribution. There is also a method of separating microparticles by allowing a solution to be in contact with abase having protrusions, which are hardly different from each other, at density of at least 100 protrusions per square centimeter on the surface thereof (JP-A 2006-104193/Patent Document 2), but there still are many to be solved such as an amount of production.

It has been desired to provide stable and dispersible drug particles in nanomicron size, in which particle diameters are easily regulated; aggregation or precipitation after aggregation is unlikely to occur; other than main drugs, fewer additives such as surfactant and stabilizer are contained; and redispersibility is excellent. In addition, it has been strongly requested to provide a pharmaceutical composition, in which no contamination due to mechanical abrasion and the like happens; safety and stability are securely maintained; and bioavailability is excellent.

DISCLOSURE OF INVENTION

An object of the present invention is to provide, regarding a method for producing particles by separating crystals through crystallization, a method for producing biologically ingestible microparticles in particular, and to improve an in vivo bioabsorption rate of a biologically ingestible material into the living body by atomization thereof. Because growth of bacteria can be problematic, another object of the present invention is to provide a safer and inexpensive biologically ingestible material (drug) by reducing the processing time.

The present invention relates to a method for producing biologically ingestible microparticles, which comprises separating biologically ingestible microparticles by a neutralization reaction in a thin film fluid formed between two processing surfaces arranged to be opposite to each other to be able to approach to and separate from each other, at least one of which rotates relative to the other, wherein the temperature in the thin film fluid is highly uniform and stirring in a reaction container is highly uniform, so that biologically ingestible microparticles that are monodisperse can be prepared according to the intended object; self-dischargeability prevents clogging with products; large pressure is not necessary; and productivity is excellent.

Still, another object of the present invention is to provide safe and inexpensive aseptic suspended eye drops by preparing a stable suspension.

The present inventor has found stable and highly dispersible biologically ingestible microparticles and a method for producing biologically ingestible microparticles having a high degree of crystallization. These particles can be formed into a pharmaceutical preparation indicating significantly high bioavailability. The above-mentioned problems have been solved by a method for producing biologically ingestible microparticles, which comprises separating biologically ingestible microparticles in a thin film fluid formed between two processing surfaces having a solution of a compound (first solvent) and a new solvent (second solvent) arranged to be opposite to each other to be able to approach to and separate from each other, at least one of which rotates relative to the other, as well as by an apparatus performing diffusion, stirring and mixing in a thin film fluid formed between processing surfaces arranged to be opposite to each other. The living body as described above includes not only the human body but also bodies of other living things.

Specifically, the above-mentioned problems are solved by the following aspects of the present invention.

A first aspect of the invention provides a method for producing biologically ingestible microparticles, wherein, in producing biologically ingestible microparticles by processing raw materials of biologically ingestible microparticles in a fluid, the fluid is formed into a thin film fluid between two processing surfaces arranged so as to be able to approach to and separate from each other, at least one of which rotates relative to the other, and biologically ingestible microparticles are separated in the thin film fluid.

A second aspect of the invention according to claim 2 of the present application provides the method for producing biologically ingestible microparticles according to claim 1, wherein at least two fluids are used, wherein at least one kind of the fluids is a fluid having at least one of the raw materials of biologically ingestible microparticles dissolved in a first solvent, at least one kind of a fluid other than the above fluid is a solvent capable of serving as a second solvent having lower solubility than that of the first solvent, and the respective fluids join together in a thin film fluid between two processing surfaces arranged so as to be able to approach to and separate from each other, at least one of which rotates relative to the other, whereby biologically ingestible microparticles are separated in the thin film fluid.

A third aspect of the invention provides the method for producing biologically ingestible microparticles, wherein at least two fluids are used, wherein at least one kind of the fluids is a fluid containing at least one acidic substance or cationic substance, at least one kind of a fluid other than the above fluid is a fluid containing at least one basic substance or anionic substance, and the respective fluids join together in a thin film fluid between two processing surfaces arranged so as to be able to approach to and separate from each other, at least one of which rotates relative to the other, whereby biologically ingestible microparticles are separated by a neutralization reaction in the thin film fluid.

A fourth aspect of the invention provides the method for producing biologically ingestible microparticles, wherein the separation reaction includes a fluid pressure imparting mechanism that imparts predetermined pressure to a fluid to be processed, at least two processing members of a first processing member and a second processing member capable of approaching to and separating from the first processing member, and a rotation drive mechanism that rotates the first processing member and the second processing member relative to each other, wherein each of the processing members is provided with at least two processing surfaces of a first processing surface and a second processing surface disposed in a position they are faced with each other; each of the processing surfaces constitutes part of a sealed flow path through which the fluid under the predetermined pressure is passed; two or more fluids to be processed, at least one of which contains a reactant, are uniformly mixed and positively reacted between the processing surfaces; of the first and second processing members, at least the second processing member is provided with a pressure-receiving surface, and at least part of the pressure-receiving surface is comprised of the second processing surface, the pressure-receiving surface receives pressure applied to the fluid by the fluid pressure imparting mechanism thereby generating a force to move in the direction of separating the second processing surface from the first processing surface; and the fluid under the predetermined pressure is passed between the first and second processing surfaces being capable of approaching to and separating from each other and rotating relative to each other, whereby the processed fluid forms a fluid film of predetermined thickness while passing between both the processing surfaces, and the separation reaction further includes another introduction path independent of the flow path through which the fluid to be processed under the predetermined pressure is passed, and at least one opening leading to the separate introduction path and being arranged in at least either the first processing surface or the second processing surface, wherein at least one processed fluid sent from the introduction path is introduced into between the processing surfaces, whereby the reactant contained in at least any one of the aforementioned processed fluids, and a fluid other than said processed fluid enable a state of desired reaction by mixing under uniform stirring in the fluid film.

A fifth aspect of the invention provides the method for producing biologically ingestible microparticles, wherein heat (warmth) is added between the processing surfaces; ultraviolet ray (UV) is irradiated between the processing surfaces; or ultrasonic energy is supplied between the processing surfaces.

A sixth aspect of the invention provides the method for producing biologically ingestible microparticles, wherein the neutralization reaction is conducted in a container capable of securing a depressurized or vacuum state, and a secondary side at which the fluid after processing is discharged can be depressurized or vacuumized to remove a gas generated during the reaction, to remove a gas discharged from the processing member, or to remove the solvent of the fluid.

A seventh aspect of the invention provides the method for producing biologically ingestible microparticles, wherein at least one of the fluids comprises at least one kind selected from a dispersant, a water-soluble polymer, a stabilizer, a preservative, a pH regulating agent and a tonicity agent.

An eighth aspect of the invention provides the method for producing biologically ingestible microparticles, wherein each of the fluids is subjected to aseptic filtration before or after the processing.

A ninth aspect of the invention provides the method for producing biologically ingestible microparticles, wherein the objective substance is a drug selected from the group consisting of analgesic agents, anti-inflammatory agents, anthelmintic agents, antiarrhythmic agents, antibiotics, anticoagulants, antihypotensive drugs, antidiabetic agents, antiepileptic drugs, antihistaminic agents, anti-malignant tumor agents, anorectic drugs, anti-obesity drugs, antihypertensive agents, antimuscarinic drugs, antimycobacterial agents, antineoplastic agents, immunosuppressive agents, antithyroid agents, antibacterial agents, antiviral agents, anti-anxiety drugs, astringents, beta-adrenoreceptor blockers, blood preparations, plasma substitutes, myocardial inotropic agents, contrast media, corticosteroids, cough suppressants, diagnostic agents, diagnostic image-forming agents, diuretic agents, dopaminergic agents, hemostatic drugs, immunological agents, lipid regulatory agents, muscle relaxants, parasympathomimetic agents, parathyroid calcitonin, biphosphonates, prostaglandins, radioactive agents, sex hormones, antiallergic agents, stimulants, anorexigenic agents, sympathomimetics, thyroid agents, vasodilators and xanthines, cataract remedies, and adrenal corticosteroids.

A tenth aspect of the invention provides biologically ingestible microparticles obtained by the production method.

An eleventh aspect of the invention provides the biologically ingestible microparticles, wherein the degree of crystallization thereof is 50% or more based on the total mass of the obtained biologically ingestible microparticles, and a liquid containing the particles does not visually show precipitation after aggregation or particle aggregation for two days or more after the preparation thereof.

A twelfth aspect of the invention provides the biologically ingestible microparticles, wherein the average primary particle size is 0.5 nm to 10000 nm.

A thirteenth aspect of the invention provides the biologically ingestible microparticles, wherein 90% particle diameter in particle size distribution/particle diameter distribution is 500 nm or less.

A fourteenth aspect of the invention provides a dispersant comprising the biologically ingestible microparticles.

A fifteenth aspect of the invention provides a pharmaceutical composition comprising a dispersant comprising the biologically ingestible microparticles and a pharmaceutically acceptable carrier.

The present invention makes it possible that various kinds of biologically ingestible microparticles not accompanied by unacceptable contamination can be prepared. Further, single crystals can be stably obtained, and thus mass production is feasible with high production efficiency. Moreover, a method in which drug particle diameters can be freely controlled by regulating the distance between processing surfaces arranged to be opposite to each other, without causing unacceptable dust levels occurred in the conventional dry crushing method or without abrasion of media by wet crushing, is provided. In addition, more inexpensive biologically ingestible microparticles can be provided by reducing the processing time which may otherwise cause the problem of growth of bacteria.

The present invention also makes it possible that a pharmaceutical composition exhibiting unexpectedly high biological availability, and a pharmaceutical composition containing a low water-soluble drug and being suitable for intravenous injection, can be provided.

The biologically ingestible microparticles obtained in the present invention are superior in redispersibility to those obtained by the conventional methods and can provide monodisperse biologically ingestible microparticles not causing aggregation. Depending on a necessary amount of production, an apparatus effecting the present invention can be developed in size by using general scale-up concept. Further, the present invention can improve energy efficiency as compared with the conventional methods.

In the production method of the present invention, aseptic filtration is also possible. The dispersant when used as suspended dye drops is excellent in corneal permeability. As compared with the case where raw materials of biologically ingestible microparticles are sterilized by dry heat and mechanically crushed or dispersed, the time for reaching the same final particle diameter can be significantly reduced.

BRIEF DESCRIPTION OF DRAWINGS

FIG. 1(A) is a schematic vertical sectional view showing the concept of the apparatus used for carrying out the present invention, FIG. 1(B) is a schematic vertical sectional view showing the concept of another embodiment of the apparatus, FIG. 1(C) is a schematic vertical sectional view showing the concept of still another embodiment of the apparatus, and FIG. 1(D) is a schematic vertical sectional view showing the concept of still another embodiment of the apparatus.

FIG. 2(A) to FIG. 2(D) each show a schematic vertical sectional view showing the concept of still another embodiment of the apparatus shown in FIG. 1.

FIG. 29(A) is a bottom view of the second processing member, and FIG. 29(B) is an enlarged sectional view showing an important part thereof.

BEST MODE FOR CARRYING OUT THE INVENTION

Figure 3:
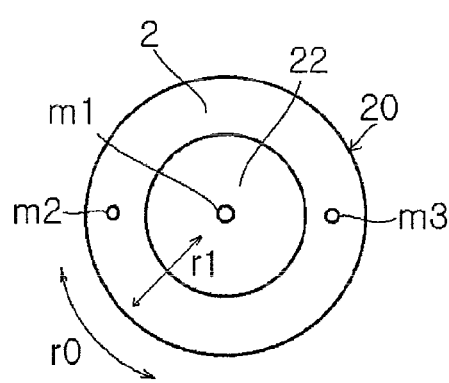
FIG. 3(A) is a schematic bottom view showing an important part of the apparatus shown in FIG. 2(C)
FIG. 3(B) is a schematic bottom view showing an important part of another embodiment of the apparatus.
FIG. 3(C) is a schematic bottom view showing an important part of still another embodiment of the apparatus.
FIG. 3(D) is a schematic bottom view showing the concept of still another embodiment of the apparatus.
FIG. 3(E) is a schematic bottom view showing the concept of still another embodiment of the apparatus.
FIG. 3(F) is a schematic bottom view showing the concept of still another embodiment of the apparatus.
Figure 3:
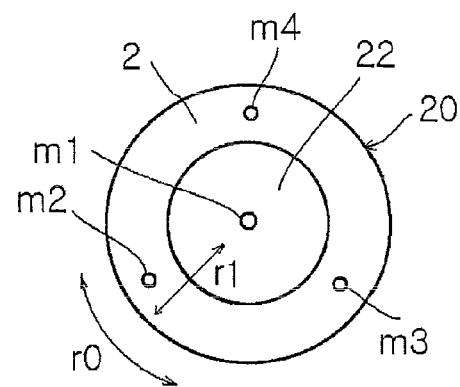
Figure 3:
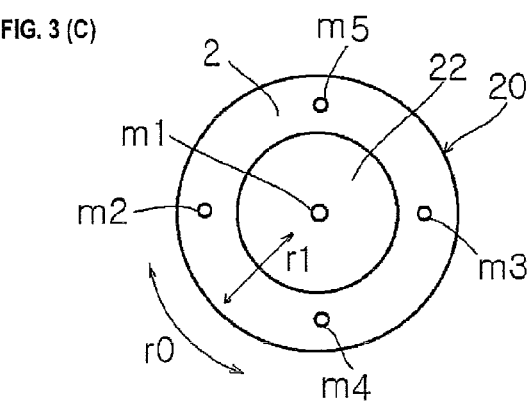
Figure 3:
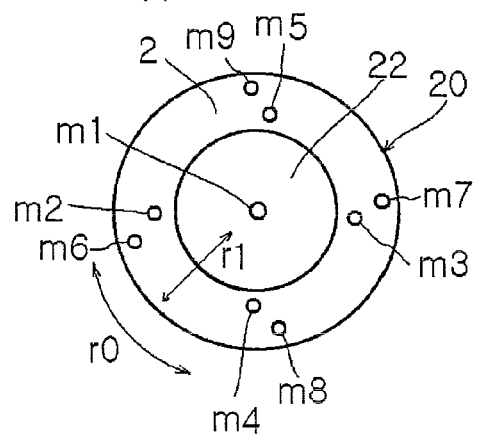
Figure 3:
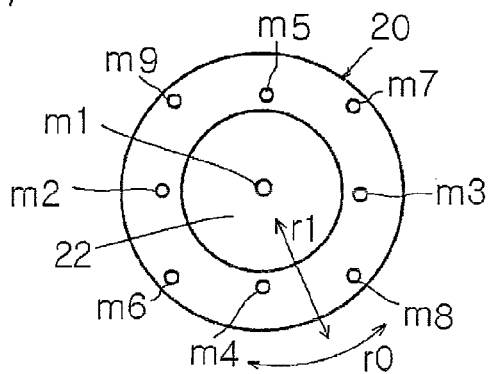
Figure 3:
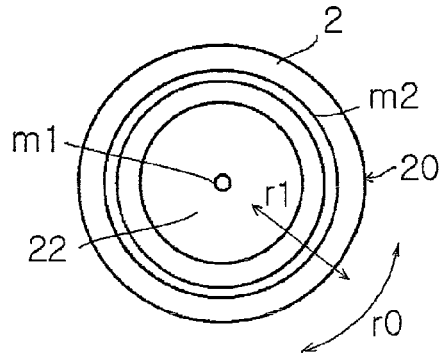

Hereinafter, the present invention will be described in detail. The technical scope of the present invention is not limited by the following embodiments and examples, and the present invention can be carried out with various modifications without changing the gist thereof.

The method of the present invention comprises separating, in a thin film fluid, raw materials of biologically ingestible microparticles as a reactant, thereby producing biologically ingestible microparticles, wherein the fluid is formed into a thin film fluid between two processing surfaces arranged so as to be able to approach to and separate from each other, at least one of which rotates relative to the other, and biologically ingestible microparticles are separated in the thin film fluid.

An apparatus of the same principle as described in JP-A 2004-49957 filed by the present applicant, for example, can be used in the method of uniform stirring and mixing in a thin film fluid formed between processing surfaces arranged to be opposite to each other so as to be able to approach to and separate from each other, at least one of which rotates relative to the other.

Hereinafter, the fluid processing apparatus suitable for carrying out this method is described.

As shown in FIG. 1(A), this apparatus includes opposing first and second processing members 10 and 20, at least one of which rotates to the other. The opposing surfaces of both the processing members 10 and 20 serve as processing surfaces 1 and 2 to process a fluid to be processed therebetween. The first processing member 10 includes a first processing surface 1, and the second processing member 20 includes a second processing surface 2.

Both the processing surfaces 1 and 2 are connected to a flow path of the fluid to constitute a part of the flow path of the fluid.

Specifically, this apparatus constitutes flow paths of at least two fluids to be processed and joins the flow paths together.

That is, this apparatus is connected to a flow path of a first fluid to form a part of the flow path of the first fluid and simultaneously forms a part of a flow path of a second fluid other than the first fluid. This apparatus joins both the flow paths together thereby mixing and reacting both the fluids between the processing surfaces 1 and 2. In the embodiment shown in FIG. 1(A), each of the flow paths is hermetically closed and made liquid-tight (when the processed fluid is a liquid) or air-tight (when the processed fluid is a gas).

Specifically, this apparatus as shown in FIG. 1(A) includes the first processing member 10, the second processing member 20, a first holder 11 for holding the first processing member 10, a second holder 21 for holding the second processing member 20, a surface-approaching pressure imparting mechanism 4, a rotation drive member, a first introduction part d1, a second introduction part d2, a fluid pressure imparting mechanism p1, a second fluid supply part p2, and a case 3.

Illustration of the rotation drive member is omitted.

At least one of the first processing member 10 and the second processing member 20 is able to approach to and separate from each other, and the processing surfaces 1 and 2 are able to approach to and separate from each other.

In this embodiment, the second processing member 20 approaches to and separates from the first processing member 10. On the contrary, the first processing member 10 may approach to and separate from the second processing member 20, or both the processing members 10 and 20 may approach to and separate from each other.

The second processing member 20 is disposed over the first processing member 10, and the lower surface of the second processing member 20 serves as the second processing surface 2, and the upper surface of the first processing member 10 serves as the first processing surface 1.

As shown in FIG. 1(A), the first processing member 10 and the second processing member 20 in this embodiment are circular bodies, that is, rings. Hereinafter, the first processing member 10 is referred to as a first ring 10, and the second processing member 20 as a second ring 20.

Both the rings 10 and 20 in this embodiment are metallic members having, at one end, a mirror-polished surface, respectively, and their mirror-polished surfaces are referred to as the first processing surface 1 and the second processing surface 2, respectively. That is, the upper surface of the first ring 10 is mirror-polished as the first processing surface 1, and the lower surface of the second ring 20 is mirror-polished as the second processing surface 2.

At least one of the holders can rotate relative to the other holder by the rotation drive member. In FIG. 1(A), numerical 50 indicates a rotary shaft of the rotation drive member. The rotation drive member may use an electric motor. By the rotation drive member, the processing surface of one ring can rotate relative to the processing surface of the other ring.

In this embodiment, the first holder 11 receives drive power on the rotary shaft 50 from the rotation drive member and rotates relative to the second holder 21, whereby the first ring 10 integrated with the first holder 11 rotates relative to the second ring 20. Inside the first ring 10, the rotary shaft 50 is disposed in the first holder 11 so as to be concentric, in a plane, with the center of the circular first ring 10.

The first ring 10 rotates centering on the shaft center of the first ring 10. The shaft center (not shown) is a virtual line referring to the central line of the first ring 10.

In this embodiment as described above, the first holder 11 holds the first ring 10 such that the first processing surface 1 of the first ring 10 is directed upward, and the second holder 21 holds the second ring 20 such that the second processing surface 2 of the second ring 20 is directed downward.

Specifically, the first and second holders 11 and 21 include a ring-accepting concave part, respectively. In this embodiment, the first ring 10 is fitted in the ring-accepting part of the first holder 11, and the first ring 10 is fixed in the ring-accepting part so as not to rise from, and set in, the ring-accepting part of the first holder 11.

That is, the first processing surface 1 is exposed from the first holder 11 and faces the second holder 21.

Examples of the material for the first ring 10 include metal, ceramics, sintered metal, abrasion-resistant steel, metal subjected to hardening treatment, and rigid materials subjected to lining, coating or plating. The first processing member 10 is preferably formed of a lightweight material for rotation. A material for the second ring 20 may be the same as that for the first ring 10.

The ring-accepting part 41 arranged in the second holder 21 accepts the processing surface 2 of the second ring 20 such that the processing member can rise and set.

The ring-accepting part 41 of the second holder 21 is a concave portion for mainly accepting that side of the second ring 20 opposite to the processing surface 2, and this concave portion is a groove which has been formed into a circle when viewed in a plane.

The ring-accepting part 41 is formed to be larger in size than the second ring 20 so as to accept the second ring 20 with sufficient clearance between itself and the second ring 20.

By this clearance, the second ring 20 in the ring-accepting part 41 can be displaced not only in the axial direction of the circular ring-accepting part 41 but also in a direction perpendicular to the axial direction. In other words, the second ring 20 can, by this clearance, be displaced relative to the ring-accepting part 41 to make the central line of the second ring 20 unparallel to the axial direction of the ring-accepting part 41.

Hereinafter, that portion of the second holder 21 which is surrounded by the second ring 20 is referred to as a central portion 22.

In other words, the second ring 20 is displaceably accepted within the ring-accepting part 41 not only in the thrust direction of the ring-accepting part 41, that is, in the direction in which the second ring 20 rises from and sets in the part 41, but also in the decentering direction of the second ring 20 from the center of the ring-accepting part 41. Further, the second ring 20 is accepted in the ring-accepting part 41 such that the second ring 20 can be displaced (i.e. run-out) to vary the width between itself upon rising or setting and the ring-accepting part 41, at each position in the circumferential direction of the second ring 20.

The second ring 20, while maintaining the degree of its move in the above three directions, that is, the axial direction, decentering direction and run-out direction of the second ring 20 relative to the ring-accepting part 41, is held on the second holder 21 so as not to follow the rotation of the first ring 10. For this purpose, suitable unevenness (not shown) for regulating rotation in the circumferential direction of the ring-accepting part 41 may be arranged both in the ring-accepting part 41 and in the second ring 20. However, the unevenness should not deteriorate displacement in the degree of its move in the three directions.

The surface-approaching pressure imparting mechanism 4 supplies the processing members with force exerted in the direction of approaching the first processing surface 1 and the second processing surface 2 each other. In this embodiment, the surface-approaching pressure imparting mechanism 4 is disposed in the second holder 21 and biases the second ring 20 toward the first ring 10.

The surface-approaching pressure imparting mechanism 4 uniformly biases each position in the circumferential direction of the second ring 20, that is, each position of the second processing surface 2, toward the first ring 10. A specific structure of the surface-approaching pressure imparting mechanism 4 will be described later.

As shown in FIG. 1(A), the case 3 is arranged outside the outer circumferential surfaces of both the rings 10 and 20, and accepts a product formed between the processing surfaces 1 and 2 and discharged to the outside of both the rings 10 and 20. As shown in FIG. 1(A), the case 3 is a liquid-tight container for accepting the first holder 11 and the second holder 21. However, the second holder 21 may be that which as a part of the case 3, is integrally formed with the case 3.

As described above, the second holder 21 whether formed as a part of the case 3 or formed separately from the case 3 is not movable so as to influence the distance between both the rings 10 and 20, that is, the distance between the processing surfaces 1 and 2. In other words, the second holder 21 does not influence the distance between the processing surfaces 1 and 2.

The case 3 is provided with an outlet 32 for discharging a product to the outside of the case 3.

The first introduction part d1 supplies a first fluid to be processed to the space between the processing surfaces 1 and 2.

The fluid pressure imparting mechanism p1 is connected directly or indirectly to the first introduction part d1 to impart fluid pressure to the first fluid. A compressor or a pump can be used in the fluid pressure imparting mechanism p1.

In this embodiment, the first introduction part d1 is a fluid path arranged inside the central part 22 of the second holder 21, and one end of the first introduction part d1 is open at the central position of a circle, when viewed in a plane, of the second ring 20 on the second holder 21. The other end of the first introduction part d1 is connected to the fluid pressure imparting mechanism p1 outside the second holder 21, that is, outside the case 3.

The second introduction part d2 supplies a second fluid to be reacted with the first fluid to the space between the processing surfaces 1 and 2. In this embodiment, the second introduction part is a fluid passage arranged inside the second ring 20, and one end of the second introduction part is open at the side of the second processing surface 2, and a second fluid-feeding part p2 is connected to the other end.

A compressor or a pump can be used in the second fluid-feeding part p2.

The first processed fluid pressurized with the fluid pressure imparting mechanism p1 is introduced from the first introduction part d1 to the space between the rings 10 and 20 and will pass through the space between the first processing surface 1 and the second processing surface 2 to the outside of the rings 10 and 20.

At this time, the second ring 20 receiving the supply pressure of the first fluid stands against the bias of the surface-approaching pressure imparting mechanism 4, thereby receding from the first ring 10 and making a minute space between the processing surfaces. The space between both the processing surfaces 1 and 2 by approach and separation of the surfaces 1 and 2 will be described in detail later.

A second fluid is supplied from the second introduction part d2 to the space between the processing surfaces 1 and 2, flows into the first fluid, and is subjected to a reaction promoted by rotation of the processing surface. Then, a reaction product formed by the reaction of both the fluids is discharged from the space between the processing surfaces 1 and 2 to the outside of both the rings 10 and 20. The reaction product discharged to the outside of the rings 10 and 20 is discharged finally through the outlet 32 of the case 3 to the outside of the case 3.

The mixing and reaction of the processed fluid are effected between the first processing surface 1 and the second processing surface 2 by rotation, relative to the second processing member 20, of the first processing member 10 with the drive member.

Between the first and second processing surfaces 1 and 2, a region downstream from an opening m2 of the second introduction part d2 serves as a reaction chamber where the first and second processed fluids are reacted with each other. Specifically, as shown in FIG. 11(C) illustrating a bottom face of the second ring 20, a region H shown by oblique lines, outside the second opening m2 of the second introduction part in the radial direction r1 of the second ring 20, serves as the processing chamber, that is, the reaction chamber. Accordingly, this reaction chamber is located downstream from the openings m1 and m2 of the first introduction part d1 and the second introduction part d2 between the processing surfaces 1 and 2.

The first fluid introduced from the first opening m1 through a space inside the ring into the space between the processing surfaces 1 and 2, and the second fluid introduced from the second opening m2 into the space between the processing surfaces 1 and 2, are mixed with each other in the region H serving as the reaction chamber, and both the processed fluids are reacted with each other. The fluid will, upon receiving supply pressure from the fluid pressure imparting mechanism p1, move through the minute space between the processing surfaces 1 and 2 to the outside of the rings, but because of rotation of the first ring 10, the fluid mixed in the reaction region H does not move linearly from the inside to the outside of the rings in the radial direction, but moves from the inside to the outside of the ring spirally around the rotary shaft of the ring when the processing surfaces are viewed in a plane. In the region H where the fluids are thus mixed and reacted, the fluids can move spirally from inside to outside to secure a zone necessary for sufficient reaction in the minute space between the processing surfaces 1 and 2, thereby promoting their uniform reaction.

The product formed by the reaction becomes a uniform reaction product in the minute space between the first processing surface 1 and the second processing surface 2 and appears as microparticles particularly in the case of crystallization or separation.

By the balance among at least the supply pressure applied by the fluid pressure imparting mechanism p1, the bias of the surface-approaching pressure imparting mechanism 4, and the centrifugal force resulting from rotation of the ring, the distance between the processing surfaces 1 and 2 can be balanced to attain a preferable minute space, and further the processed fluid receiving the supply pressure applied by the fluid pressure imparting mechanism p1 and the centrifugal force by rotation of the ring moves spirally in the minute space between the processing surfaces 1 and 2, so that their reaction is promoted.

The reaction is forcedly effected by the supply pressure applied by the fluid pressure imparting mechanism p1 and the rotation of the ring. That is, the reaction occurs under forced uniform mixing between the processing surfaces 1 and 2 arranged opposite to each other so as to be able to approach to and separate from each other, at least one of which rotates relative to the other.

Accordingly, the crystallization and separation of the product formed by the reaction can be regulated by relatively easily controllable methods such as regulation of supply pressure applied by the fluid pressure imparting mechanism p1 and regulation of the rotating speed of the ring, that is, the number of revolutions of the ring.

As described above, this processing apparatus is excellent in that the space between the processing surfaces 1 and 2, which can exert influence on the size of a product, and the distance in which the processed fluid moves in the reaction region H, which can exert influence on production of a uniform product, can be regulated by the supply pressure and the centrifugal force.

The reaction processing gives not only deposit of the product but also liquids.

The rotary shaft 50 is not limited to the vertically arranged one and may be arranged in the horizontal direction or arranged at a slant. This is because during processing, the reaction occurs in such a minute space between the processing surfaces 1 and 2 that the influence of gravity can be substantially eliminated.

In FIG. 1(A), the first introduction part d1 extends vertically and coincides with the shaft center of the second ring 20 in the second holder 21. However, the first introduction part d1 is not limited to the one having a center coinciding with the shaft center of the second ring 20 and may be arranged in other positions in the central portion 22 of the second holder 21 as long as the first fluid can be supplied into the space surrounded by the rings 10 and 20, and the first introduction part d1 may extend obliquely as well as vertically.

Figure 12:
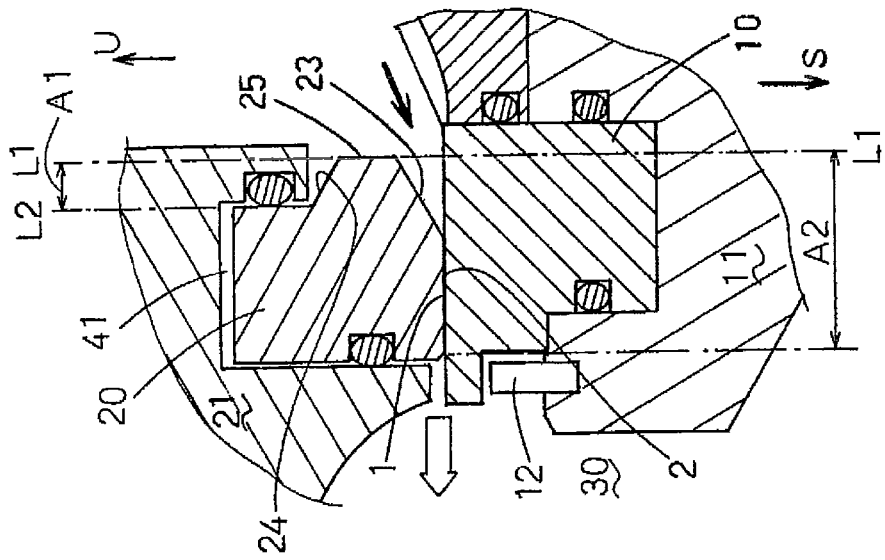
FIG. 12(A) is a schematic vertical sectional view showing an important part of another embodiment of a pressure-receiving surface in the apparatus shown in FIG. 1(A)
FIG. 12(B) is a schematic vertical sectional view showing an important part of still another embodiment of the apparatus.
Figure 12:
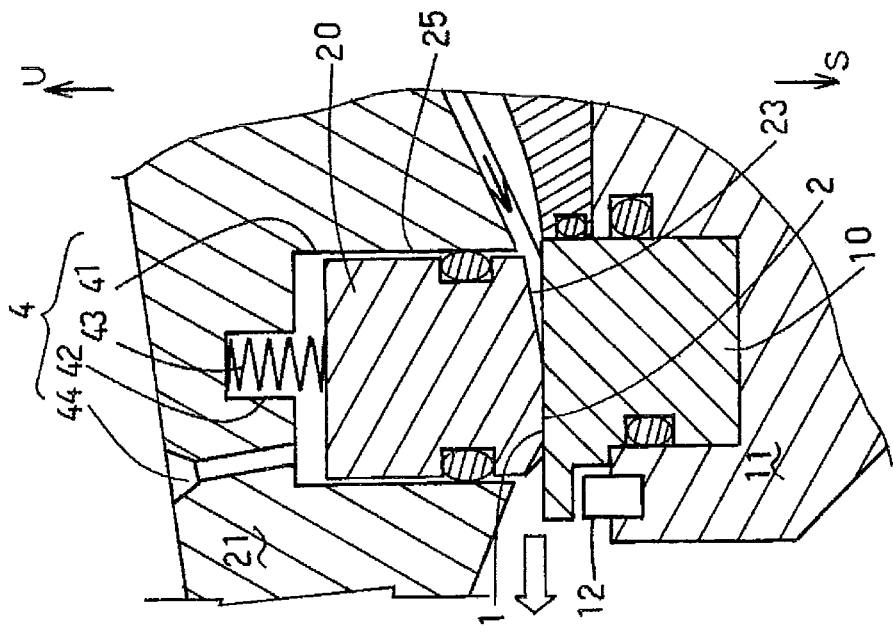

A more preferable embodiment of the apparatus is shown in FIG. 12(A). As shown in this figure, the second processing member 20 has the second processing surface 2 and a pressure-receiving surface 23 which is positioned inside, and situated next to, the second processing surface 2. Hereinafter, the pressure-receiving surface 23 is also referred to as a separation-regulating surface 23. As shown in the figure, the separation-regulating surface 23 is an inclined surface.

As described above, the ring-accepting part 41 is formed in the bottom (i.e. a lower part) of the second holder 21, and the second processing member 20 is accepted in the ring-accepting part 41. The second processing member 20 is held by the second holder 21 so as not to be rotated with a baffle (not shown). The second processing surface 2 is exposed from the second holder 21.

In this embodiment, a material to be processed is introduced inside the first processing member 10 and the second processing member 20 between the processing surfaces 1 and 2, and the processed material is discharged to the outside of the first processing member 10 and the second processing member 20.

The surface-approaching pressure imparting mechanism 4 presses by pressure the second processing surface 2 against the first processing surface 1 to make them contacted with or close to each other, and generates a thin film fluid of predetermined thickness by the balance between the surface-approaching pressure and the force, e.g. fluid pressure, of separating the processing surfaces 1 and 2 from each other. In other words, the distance between the processing surfaces 1 and 2 is kept in a predetermined minute space by the balance between the forces.

Specifically, the surface-approaching pressure imparting mechanism 4 in this embodiment is comprised of the ring-accepting part 41, a spring-accepting part 42 arranged in the depth of the ring-accepting part 41, that is, in the deepest part of the ring-accepting part 41, a spring 43, and an air introduction part 44.

However, the surface-approaching pressure imparting mechanism 4 may be the one including at least one member selected from the ring-accepting part 41, the spring-accepting part 42, the spring 43, and the air introduction part 44.

The ring-accepting part 41 has the second processing member 20 fit into it with play to enable the second processing member 20 to be displaced vertically deeply or shallowly, that is, vertically in the ring-accepting part 41.

One end of the spring 43 is abutted against the depth of the spring-accepting part 42, and the other end of the spring 43 is abutted against the front (i.e., the upper part) of the second processing member 20 in the ring-accepting part 41. In FIG. 12A, only one spring 43 is shown, but a plurality of springs 43 are preferably used to press various parts of the second processing member 20. This is because as the number of springs 43 increases, pressing pressure can be given more uniformly to the second processing member 20. Accordingly, several to a few dozen springs 43 comprising a multi-spring type preferably attach to the second holder 21.

In this embodiment, air can be introduced through the air introduction part 44 into the ring-accepting part 41. By such introduction of air, air pressure together with pressure by the spring 43 can be given as pressing pressure from the space, as a pressurizing chamber, between the ring-accepting part 41 and the second processing member 20 to the second processing member 20. Accordingly, adjusting the pressure of air introduced through the air introduction part 44 can regulate the surface-approaching pressure of the second processing surface 2 toward the first processing surface 1 during operation. A mechanism of generating pressing pressure with another fluid pressure such as oil pressure can be utilized in place of the air introduction part 44 utilizing air pressure.

The surface-approaching pressure imparting mechanism 4 not only supplies and regulates a part of the pressing pressure, that is, the surface-approaching pressure, but also serves as a displacement regulating mechanism and a buffer mechanism.

Specifically, the surface-approaching pressure imparting mechanism 4 as a displacement regulating mechanism can maintain initial pressing pressure by regulating air pressure against the change in the axial direction caused by elongation or abrasion at the start of or in the operation. As described above, the surface-approaching pressure imparting mechanism 4 uses a floating mechanism of maintaining the second processing member 20 so as to be displaced, thereby also functioning as a buffer mechanism for micro-vibration or rotation alignment.

Now, the state of the thus constituted processing apparatus during use is described with reference to FIG. 1(A).

At the outset, a first fluid to be processed is pressurized with the fluid pressure imparting mechanism p1 and introduced through the first introduction part d1 into the internal space of the sealed case. On the other hand, the first processing member 10 is rotated with the rotation of the rotary shaft 50 by the rotation drive member. The first processing surface 1 and the second processing surface 2 are thereby rotated relatively with a minute space kept therebetween.

The first processed fluid is formed into a thin film fluid between the processing surfaces 1 and 2 with a minute space kept therebetween, and a second fluid to be processed which is introduced through the second introduction part d2 flows into the thin film fluid between the processing surfaces 1 and 2 to comprise apart of the thin film fluid. By this, the first and second processed fluids are mixed with each other, and a uniform reaction of both of the fluids being reacted with each other is promoted to form a reaction product. When the reaction is accompanied by separation, relatively uniform and fine particles can be formed. Even when the reaction is not accompanied by separation, a uniform reaction can be realized. The separated reaction product may be further finely atomized by shearing between the first processing surface 1 and the second processing surface 2 with the rotation of the first processing surface 1. The first processing surface 1 and the second processing surface 2 are regulated to form a minute space of 1 μm to 1 mm, particularly 1 μm to 10 μm, thereby realizing a uniform reaction and enabling production of superfine particles of several nm in diameter.

The product is discharged from the processing surfaces 1 and 2 through an outlet 32 of the case 3 to the outside of the case. The discharged product is atomized in a vacuum or depressurized atmosphere with a well-known decompression device and converted into liquid in the atmosphere to collide with each other, then what trickled down in the liquid is able to be collected as degassed liquid.

In this embodiment, the processing apparatus is provided with a case 3, but may be carried out without a case. For example, a decompression tank for degassing, that is, a vacuum tank, is arranged, and the processing apparatus may be arranged in this tank. In this case, the outlet mentioned above is naturally not arranged in the processing apparatus.

As described above, the first processing surface 1 and the second processing surface 2 can be regulated to form a minute space in the order of μm which cannot be formed by arranging mechanical clearance. Now, this mechanism is described.

The first processing surface 1 and the second processing surface 2 are capable of approaching to and separating from each other, and simultaneously rotate relative to each other. In this example, the first processing surface 1 rotates, and the second processing surface 2 slides in the axial direction thereby approaching to and separating from the first processing surface 1.

In this example, therefore, the position of the second processing surface 2 in the axial direction is arranged accurately in the order of μm by the balance between forces, that is, the balance between the surface-approaching pressure and the separating pressure, thereby establishing a minute space between the processing surfaces 1 and 2.

As shown in FIG. 12(A), the surface-approaching pressure includes the pressure by air pressure (positive pressure) from the air introduction part 44 by the surface-approaching pressure imparting mechanism 4, the pressing pressure with the spring 43, and the like.

The embodiments shown in FIG. 12 to FIG. 15 and FIG. 17 are shown by omitting the second introduction part d2 to simplify the drawings. In this respect, these drawings may be assumed to show sections at a position not provided with the second introduction part d2. In the figures, U and S show upward and downward directions respectively.

On the other hand, the separating force include the fluid pressure acting on the pressure-receiving surface at the separating side, that is, on the second processing surface 2 and the separation regulating surface 23, the centrifugal force resulting from rotation of the first processing member 10, and the negative pressure when negative pressure is applied to the air introduction part 44.

When the apparatus is washed, the negative pressure applied to the air introduction part 44 can be increased to significantly separate the processing surfaces 1 and 2 from each other, thereby facilitating washing.

By the balance among these forces, the second processing surface 2 while being remote by a predetermined minute space from the first processing surface 1 is stabilized, thereby realizing establishment with accuracy in the order of μm.

The separating force is described in more detail.

With respect to fluid pressure, the second processing member 20 in a closed flow path receives feeding pressure of a processed fluid, that is, fluid pressure, from the fluid pressure imparting mechanism p1. In this case, the surfaces opposite to the first processing surface in the flow path, that is, the second processing surface 2 and the separation regulating surface 23, act as pressure-receiving surfaces at the separating side, and the fluid pressure is applied to the pressure-receiving surfaces to generate a separating force due to the fluid pressure.

With respect to centrifugal force, the first processing member 10 is rotated at high speed, centrifugal force is applied to the fluid, and a part of this centrifugal force acts as separating force in the direction in which the processing surfaces 1 and 2 are separated from each other.

When negative pressure is applied from the air introduction part 44 to the second processing member 20, the negative pressure acts as separating force.

In the foregoing description of the present invention, the force of separating the first and second processing surfaces 1 and 2 from each other has been described as a separating force, and the above-mentioned force is not excluded from the separating force.

By forming a balanced state of the separating force and the surface-approaching pressure applied by the surface-approaching pressure imparting mechanism 4 via the fluid between the processing surfaces 1 and 2 in the flow path of the closed fluid, a uniform reaction is realized between the processing surfaces 1 and 2, and simultaneously a thin film fluid suitable for crystallization and separation of microscopic reaction products is formed as described above. In this manner, this apparatus can maintain a minute space between the processing surfaces 1 and 2 by forced thin film fluid, the minute space of which is not achievable with a conventional mechanical apparatus, and microparticles can be formed highly accurately as the reaction product.

In other words, the thickness of the thin film fluid between the processing surfaces 1 and 2 is regulated as desired by regulating the separating force and surface-approaching pressure, thereby realizing a necessary uniform reaction to form and process microscopic products. Accordingly, when the thickness of the thin film fluid is to be decreased, the surface-approaching pressure or separating force may be regulated such that the surface-approaching pressure is made relatively higher than the separating force. When the thickness of the thin film fluid is to be increased, the separating force or surface-approaching pressure may be regulated such that the separating force is made relatively higher than the surface-approaching pressure.

When the surface-approaching pressure is increased, air pressure, that is, positive pressure is applied from the air introduction part 44 by the surface-approaching pressure imparting mechanism 4, or the spring 43 is changed to the one having higher pressing pressure, or the number of springs may be increased.

When the separating force is to be increased, the feeding pressure of the fluid pressure imparting mechanism p1 is increased, or the area of the second processing surface 2 or the separation regulating surface 23 is increased, or in addition, the rotation of the first processing member 10 is regulated to increase centrifugal force or reduce pressure from the air introduction part 44. Alternatively, negative pressure may be applied. The spring 43 shown is a pressing spring that generates pressing pressure in an extending direction, but may be a pulling spring that generates a force in a compressing direction to constitute a part or the whole of the surface-approaching pressure imparting mechanism 4.

When the separating force is to be decreased, the feeding pressure of the fluid pressure imparting mechanism p1 is reduced, or the area of the second processing surface 2 or the separation regulating surface 23 is reduced, or in addition, the rotation of the first processing member 10 is regulated to decrease centrifugal force or increase pressure from the air introduction part 44. Alternatively, negative pressure may be reduced.

Further, properties of a processed fluid, such as viscosity, can be added as a factor for increasing or decreasing the surface-approaching pressure and separating force, and regulation of such properties of a processed fluid can be performed as regulation of the above factor.

In the separating force, the fluid pressure exerted on the pressure-receiving surface at the separating side, that is, the second processing surface 2 and the separation regulating surface 23 is understood as a force constituting an opening force in mechanical seal.

In the mechanical seal, the second processing member 20 corresponds to a compression ring, and when fluid pressure is applied to the second processing member 20, the force of separating the second processing member 20 from the first processing member 10 is regarded as opening force.

More specifically, when the pressure-receiving surfaces at a separating side, that is, the second processing surface 2 and the separation regulating surface 23 only are arranged in the second processing member 20 as shown in the first embodiment, all feeding pressure constitutes the opening force. When a pressure-receiving surface is also arranged at the backside of the second processing member 20, specifically in the case of FIG. 12(B) and FIG. 17 described later, the difference between the feeding pressure acting as a separating force and the feeding pressure acting as surface-approaching pressure is the opening force.

Now, other embodiments of the second processing member 20 are described with reference to FIG. 12(B).

As shown in FIG. 12(B), an approach regulating surface 24 facing upward, that is, at the other side of the second processing surface 2, is disposed at the inner periphery of the second processing member 20 exposed from the ring-accepting part 41.

That is, the surface-approaching pressure imparting mechanism 4 in this embodiment is comprised of a ring-accepting part 41, an air introduction part 44, and the approach regulating surface 24. However, the surface-approaching pressure imparting mechanism 4 may be one including at least one member selected from the ring-accepting part 41, the spring-accepting part 42, the spring 43, the air introduction part 44, and the approach regulating surface 24.

The approach regulating surface 24 receives predetermined pressure applied to a processed fluid to generate a force of approaching the second processing surface 2 to the first processing surface 1, thereby functioning in feeding surface-approaching pressure as a part of the surface-approaching pressure imparting mechanism 4. On the other hand, the second processing surface 2 and the separation regulating surface 23 receive predetermined pressure applied to a processed fluid to generate a force of separating the second processing surface 2 from the first processing surface 1, thereby functioning in feeding apart of the separating force.

The approach regulating surface 24, the second processing surface 2 and the separation regulating surface 23 are pressure-receiving surfaces receiving feeding pressure of the processed fluid, and depending on its direction, exhibits different actions, that is, generation of the surface-approaching pressure and generation of a separating force.

The ratio (area ratio A1/A2) of a projected area A1 of the approach regulating surface 24 projected on a virtual plane perpendicular to the direction of approaching and separating the processing surfaces, that is, in the direction of rising and setting of the second ring 20, to a total area A2 of the projected area of the second processing surface 2 and the separation regulating surface 23 of the second processing member 20 projected on the virtual plane is called balance ratio K which is important for regulation of the opening force.

Both the top of the approach regulating surface 24 and the top of the separation regulating surface 23 are defined by the inner periphery 25 of the circular second regulating part 20, that is, by top line L1. Accordingly, the balance ratio is regulated for deciding the place where base line L2 of the approach regulating surface 24 is to be placed.

That is, in this embodiment, when the feeding pressure of the processed fluid is utilized as opening force, the total projected area of the second processing surface 2 and the separation regulating surface 23 is made larger than the projected area of the approach regulating surface 24, thereby generating an opening force in accordance with the area ratio.

The opening force can be regulated by the pressure of the processed fluid, that is, the fluid pressure, by changing the balance line, that is, by changing the area A1 of the approach regulating surface 24.

Sliding surface actual surface pressure P, that is, the fluid pressure out of the surface-approaching pressure, is calculated according to the following equation:

$$P = P1 \times (K-k) + Ps$$

wherein P1 represents the pressure of a processed fluid, that is, fluid pressure; K represents the balance ratio; k represents an opening force coefficient; and Ps represents a spring and back pressure.

By regulating this balance line to regulate the sliding surface actual surface pressure P, the space between the processing surfaces 1 and 2 is formed as a desired minute space, thereby forming a film of the fluid to make the product minute and effecting uniform reaction processing.

Usually, as the thickness of a thin film fluid between the processing surfaces 1 and 2 is decreased, the product can be made finer. On the other hand, as the thickness of the thin film fluid is increased, processing becomes rough and the throughput per unit time is increased. By regulating the sliding surface actual surface pressure P on the sliding surface, the space between the processing surfaces 1 and 2 can be regulated to realize the desired uniform reaction and to obtain the minute product. Hereinafter, the sliding surface actual surface pressure P is referred to as surface pressure P.

From this relation, it is concluded that when the product is to be made coarse, the balance ratio may be decreased, the surface pressure P may be decreased, the space may be increased and the thickness of the film may be increased. On the other hand, when the product is to be made finer, the balance ratio may be increased, the surface pressure P may be increased, the space may be decreased and the thickness of the film may be decreased.

As a part of the surface-approaching pressure imparting mechanism 4, the approach regulating surface 24 is formed, and at the position of the balance line, the surface-approaching pressure may be regulated, that is, the space between the processing surfaces may be regulated.

As described above, the space is regulated in consideration of the pressing pressure of the spring 43 and the air pressure of the air introduction part 44. Regulation of the fluid pressure, that is, the feeding pressure of the processed fluid, and regulation of the rotation of the first processing member 10 for regulating centrifugal force, that is, the rotation of the first holder 11, are also important factors to regulate the space.

As described above, this apparatus is constituted such that for the second processing member 20 and the first processing member 10 that rotates relative to the second processing member 20, a predetermined thin film fluid is formed between the processing surfaces by pressure balance among the feeding pressure of the processed fluid, the rotation centrifugal force, and the surface-approaching pressure. At least one of the rings is formed in a floating structure by which alignment such as run-out is absorbed to eliminate the risk of abrasion and the like.

The embodiment shown in FIG. 1(A) also applies to the embodiment in FIG. 12(B) except that the regulating surface is arranged.

Figure 17:
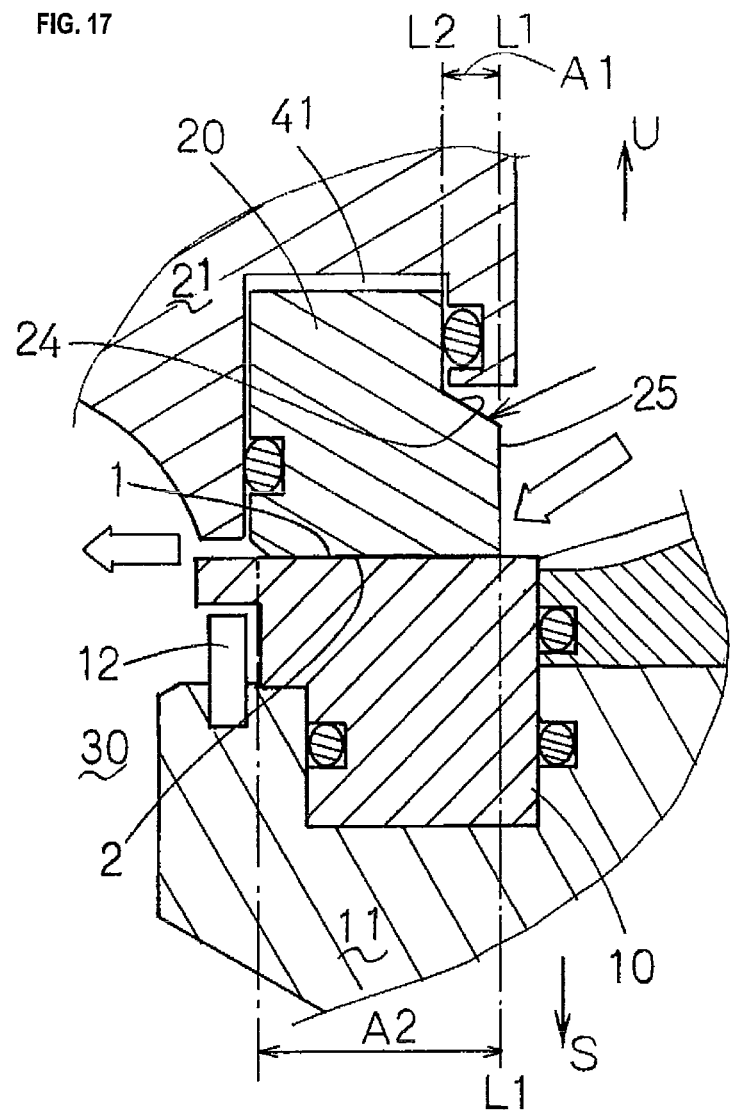
FIG. 17 is a schematic vertical sectional view showing an important part of still another embodiment of the apparatus shown in FIG. 12(A).

The embodiment shown in FIG. 12(B) can be carried out without arranging the separation regulating surface 23 on the separating side, as shown in FIG. 17.

When the approach regulating surface 24 is arranged as shown in the embodiment shown in FIG. 12(B) and FIG. 17, the area A1 of the approach regulating surface 24 is made larger than the area A2, whereby all of the predetermined pressure exerted on the processed fluid functions as surface-approaching pressure, without generating an opening force. This arrangement is also possible, and in this case, both the processing surfaces 1 and 2 can be balanced by increasing other separating force.

With the area ratio described above, the force acting in the direction of separating the second processing surface 2 from the first processing surface 1 is fixed as the resultant force exerted by the fluid.

Figure 13:
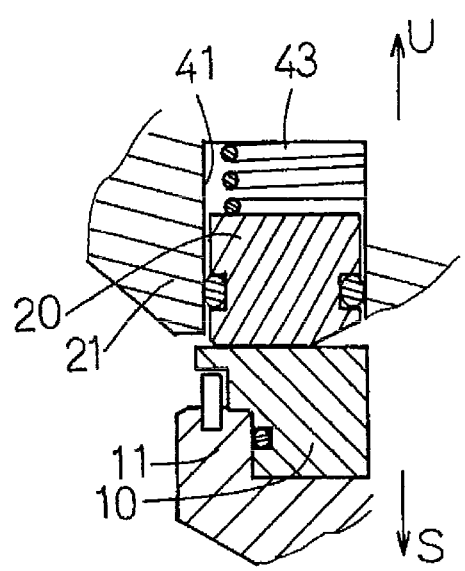
FIG. 13 is a schematic vertical sectional view showing an important part of another embodiment of a surface-approaching pressure imparting mechanism 4 in the apparatus shown in FIG. 12(A).

In this embodiment, as described above, the number of springs 43 is preferably larger in order to impart uniform stress on the sliding surface, that is, the processing surface. However, the spring 43 may be a single coil-type spring as shown in FIG. 13. As shown in the figure, this spring is a single coil spring having a center concentric with the circular second processing member 20.

The space between the second processing member 20 and the second holder 21 is sealed air-tightly with methods well known in the art.

Figure 14:
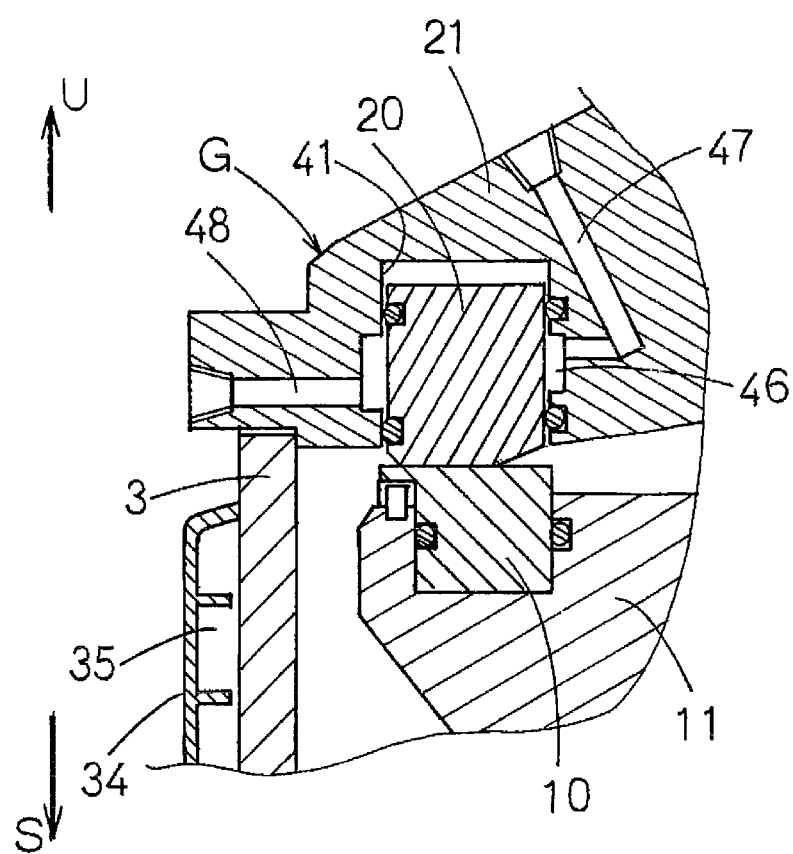
FIG. 14 is a schematic vertical sectional view showing an important part of another embodiment of the apparatus shown in FIG. 12(A), which is provided with a temperature regulating jacket.

As shown in FIG. 14, the second holder 21 is provided with a temperature regulation jacket 46 capable of regulating the temperature of the second processing member 20 by cooling or heating. Numerical 3 in FIG. 14 is the above-mentioned case, and the case 3 is also provided with a jacket 35 for the same purpose of temperature regulation.

The temperature regulation jacket 46 for the second holder 21 is a water-circulating space formed at a side of the ring-accepting part 41 and communicates with paths 47 and 48 leading to the outside of the second holder 21. One of the paths 47 and 48 introduces a cooling or heating medium into the temperature regulation jacket 46, and the other discharges the medium.

The temperature regulation jacket 35 for the case 3 is a path for passing heating water or cooling water, which is arranged between the outer periphery of the case 3 and a covering part 34 for covering the outer periphery of the case 3.

In this embodiment, the second holder 21 and the case 3 are provided with the temperature regulation jacket, but the first holder 11 can also be provided with such a jacket.

Figure 15:
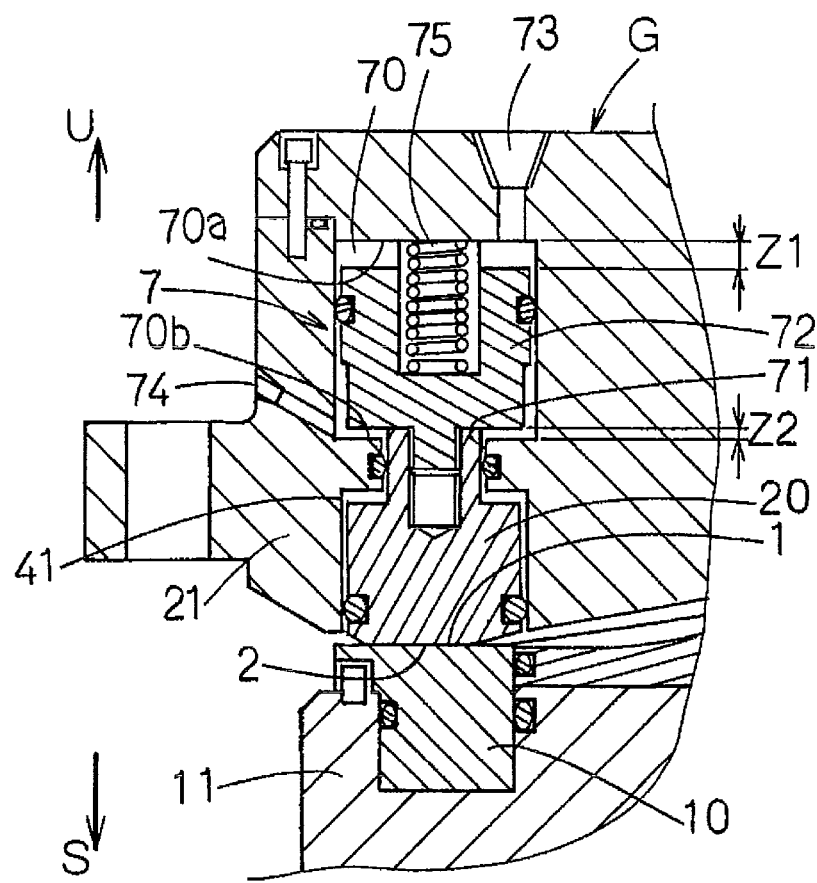
FIG. 15 is a schematic vertical sectional view showing an important part of still another embodiment of the surface-approaching pressure imparting mechanism 4 in the apparatus shown in FIG. 12(A).

As a part of the surface-approaching pressure imparting mechanism 4, a cylinder mechanism 7 shown in FIG. 15 may be arranged besides the members described above.

The cylinder mechanism 7 includes a cylinder space 70 arranged in the second holder 21, a communicating part 71 that communicates the cylinder space 70 with the ring-accepting part 41, a piston 72 that is accepted in the cylinder space 70 and connected via the communication part 71 to the second processing member 20, a first nozzle 73 that communicates to the upper part of the cylinder space 70, a second nozzle 74 that communicates to the lower part of the cylinder space 70, and a pressing body 75 such as spring between the upper part of the cylinder space 70 and the piston 72.

The piston 72 can slide vertically in the cylinder space 70, and the second processing member 20 can slide vertically with sliding of the piston 72, to change the gap between the first processing surface 1 and the second processing surface 2.

Although not shown in the figure, specifically, a pressure source such as a compressor is connected to the first nozzle 73, and air pressure, that is, positive pressure is applied from the first nozzle 73 to the upper part of the piston 72 in the cylinder space 70, thereby sliding the piston 72 downward, to narrow the gap between the first and second processing surfaces 1 and 2. Although not shown in the figure, a pressure source such as a compressor is connected to the second nozzle 74, and air pressure, that is, positive pressure is applied from the second nozzle 74 to the lower part of the piston 72 in the cylinder space 70, thereby sliding the piston 72 upward, to widen the gap between the first and second processing surfaces 1 and 2, that is, to enable it to move in the direction of opening the gap. In this manner, the surface-approaching pressure can be regulated by air pressure with the nozzles 73 and 74.

Even if there is a space between the upper part of the second processing member 20 in the ring-accepting part 41 and the uppermost part of the ring-accepting part 41, the piston 72 is arranged so as to abut against the uppermost part 70a of the cylinder space 70, whereby the uppermost part 70a of the cylinder space 70 defines the upper limit of the width of the gap between the processing surfaces 1 and 2. That is, the piston 72 and the uppermost part 70a of the cylinder space 70 function as a separation preventing part for preventing the separation of the processing surfaces 1 and 2 from each other, in other words, function in regulating the maximum opening of the gap between both the processing surfaces 1 and 2.

Even if the processing surfaces 1 and 2 do not abut on each other, the piston 72 is arranged so as to abut against a lowermost part 70b of the cylinder space 70, whereby the lowermost part 70b of the cylinder space 70 defines the lower limit of the width of the gap between the processing surfaces 1 and 2. That is, the piston 72 and the lowermost part 70b of the cylinder space 70 function as an approach preventing part for preventing the approaching of the processing surfaces 1 and 2 each other, in other words, function in regulating the minimum opening of the gap between both the processing surfaces 1 and 2.

In this manner, the maximum and minimum openings of the gap are regulated, while a distance z1 between the piston 72 and the uppermost part 70a of the cylinder space 70, in other words, a distance z2 between the piston 72 and the lowermost part 70b of the cylinder space 70, is regulated with air pressure by the nozzles 73 and 74.

The nozzles 73 and 74 may be connected to a different pressure source respectively, and further may be connected to a single pressure source alternatively or switched the connections to the sources.

The pressure source may be a source applying positive or negative pressure. When a negative pressure source such as a vacuum is connected to the nozzles 73 and 74, the action described above goes to the contrary.

In place of the other surface-approaching pressure imparting mechanism 4 or as a part of the surface-approaching pressure imparting mechanism 4, such cylinder mechanism 7 is provided to set the pressure of the pressure source connected to the nozzle 73 and 74, and the distances z1 and z2 according to the viscosity and properties of the fluid to be processed in a fashion to bring the thickness value of thin film fluid of the fluid to a desired level under a shear force to realize a uniform reaction for forming fine particles. Particularly, such cylinder mechanism 7 can be used to increase the reliability of cleaning and sterilization by forcing the sliding part open and close during cleaning and steam sterilization.

As shown in FIG. 16(A) to FIG. 16(C), the first processing surface 1 of the first processing member 10 may be provided with groove-like depressions 13 . . . 13 extending in the radial direction, that is, in the direction from the center to the outside of the first processing member 10. In this case, as shown in FIG. 16(A), the depressions 13 . . . 13 can be curved or spirally elongated on the first processing surface 1, and as shown in FIG. 16(B), the individual depressions 13 may be bent at a right angle, or as shown in FIG. 16(C), the depressions 13 . . . 13 may extend straight radially.

As shown in FIG. 16(D), the depressions 13 in FIG. 16(A) to FIG. 16(C) preferably deepen gradually in the direction toward the center of the first processing surface 1. The groove-like depressions 13 may continue in sequence or intermittence.

Formation of such depression 13 may correspond to the increase of delivery of the processed fluid or to the decrease of calorific value, while having effects of cavitation control and fluid bearing.

Figure 16:
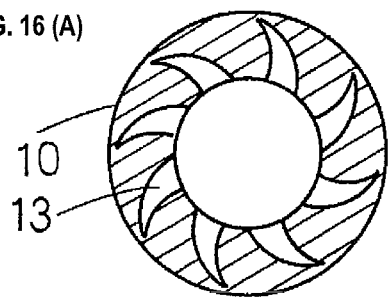
FIG. 16(A) is a schematic transverse sectional view showing an important part of still another embodiment of the apparatus shown in FIG. 12(A), FIG. 16(B), FIG. 16(C) and FIG. 16(E) to FIG. 16(G) are schematic transverse sectional views each showing an important part of still another embodiment of the apparatus.
FIG. 16(D) is a partially cut schematic vertical sectional view showing an important part of still another embodiment of the apparatus.
Figure 16:
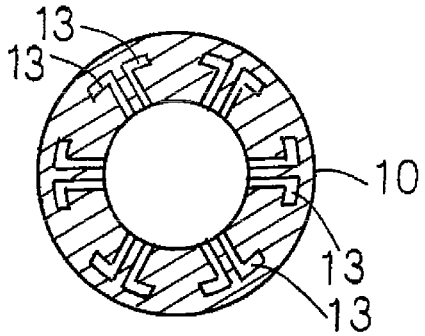
Figure 16:
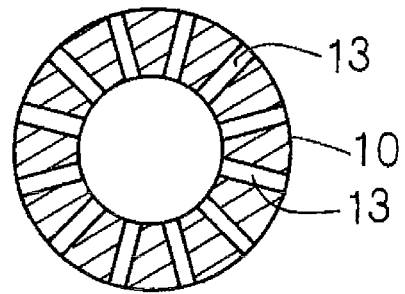
Figure 16:
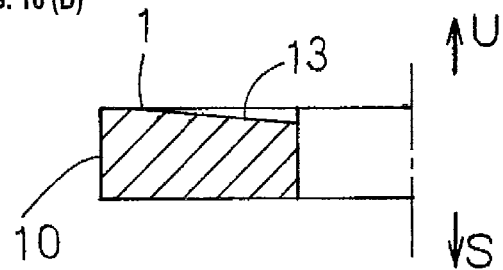
Figure 16:
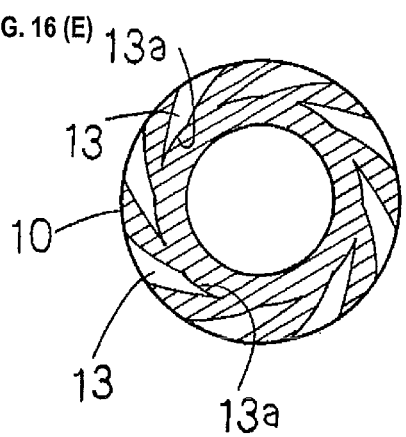
Figure 16:
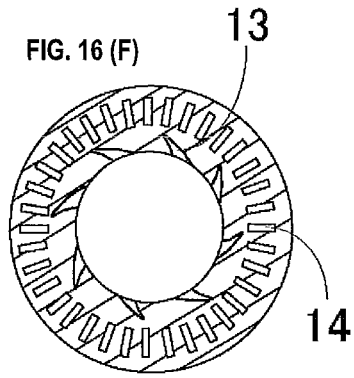
Figure 16:
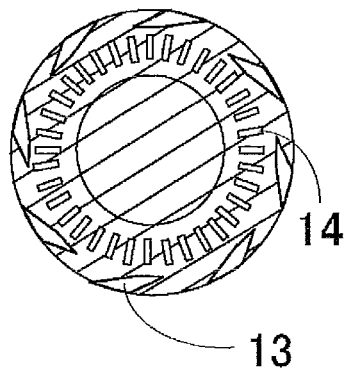

In the embodiments shown in FIG. 16, the depressions 13 are formed on the first processing surface 1, but may be formed on the second processing surface 2 or may be formed on both the first and second processing surfaces 1 and 2.

When the depressions 13 or tapered sections are not provided on the processing surface or are arranged unevenly on a part of the processing surface, the influence exerted by the surface roughness of the processing surfaces 1 and 2 on the processed fluid is greater than that by the above depressions 13. In this case, the surface roughness should be reduced, that is, the surface should be fine-textured, as the particle size of the processed fluid are to be decreased. Particularly, regarding the surface roughness of the processing surface, the mirror surface, that is, a surface subjected to mirror polishing is advantageous in realizing uniform reaction for the purpose of uniform reaction, and in realizing crystallization and separation of fine monodisperse reaction products for the purpose of obtaining microparticles.

In the embodiments shown in FIG. 13 to FIG. 17, structures other than those particularly shown are the same as in the embodiments shown in FIG. 1(A) or FIG. 11(C).

In the embodiments described above, the case is closed. Alternatively, the first processing member 10 and the second processing member 20 may be closed inside but may be open outside. That is, the flow path is sealed until the processed fluid has passed through the space between the first processing surface 1 and the second processing surface 2, to allow the processed fluid to receive the feeding pressure, but after the passing, the flow path may be opened so that the processed fluid after processing does not receive feeding pressure.

The fluid pressure imparting mechanism p1 preferably uses a compressor as a pressure device described above, but if predetermined pressure can always be applied to the processed fluid, another means may be used. For example, the own weight of the processed fluid can be used to apply certain pressure constantly to the processed fluid.

In summary, the processing apparatus in each embodiment described above is characterized in that predetermined pressure is applied to a fluid to be processed, at least two processing surfaces, that is, a first processing surface 1 and a second processing surface 2 capable of approaching to and separating from each other are connected to a sealed flow path through which the processed fluid receiving the predetermined pressure flows, a surface-approaching pressure of approaching the processing surfaces 1 and 2 each other is applied to rotate the first processing surface 1 and the second processing surface 2 relative to each other, thereby allowing a thin film fluid used for seal in mechanical seal to be generated out of the processed fluid, and the thin film fluid is leaked out consciously (without using the thin film fluid as seal) from between the first processing surface 1 and the second processing surface 2, contrary to mechanical seal, whereby reaction processing is realized between the processed fluid formed into a film between the surfaces 1 and 2, and the product is recovered.

By this epoch-making method, the space between the processing surfaces 1 and 2 can be regulated in the range of 1 μm to 1 mm, particularly 1 μm to 10 μm.

In the embodiment described above, a flow path for a sealed fluid is constituted in the apparatus, and the processed fluid is pressurized with the fluid pressure imparting mechanism p1 arranged at the side of the introduction part (for the first processing fluid) in the processing apparatus.

Alternatively, the flow path for the processed fluid may be opened without pressurization with the fluid pressure imparting mechanism p1.

Figure 18:
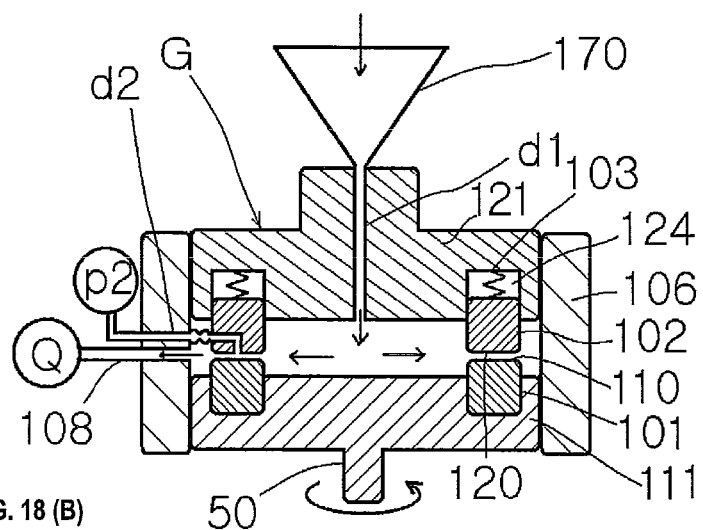
FIG. 18(A) is a schematic vertical sectional view showing the concept of still another embodiment of the apparatus used for carrying out the present invention.
FIG. 18(B) is a partially cut explanatory view showing an important part of the apparatus.
Figure 18:
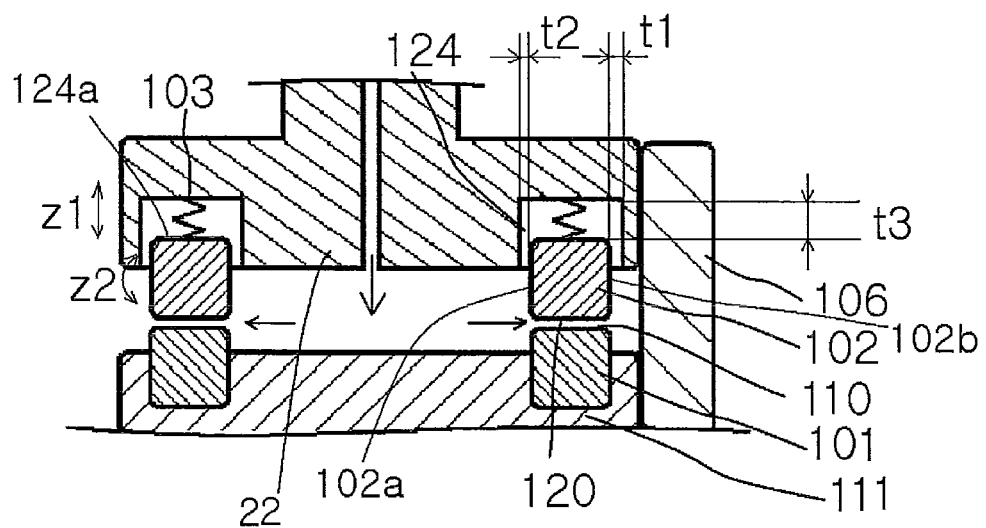
Figure 19:
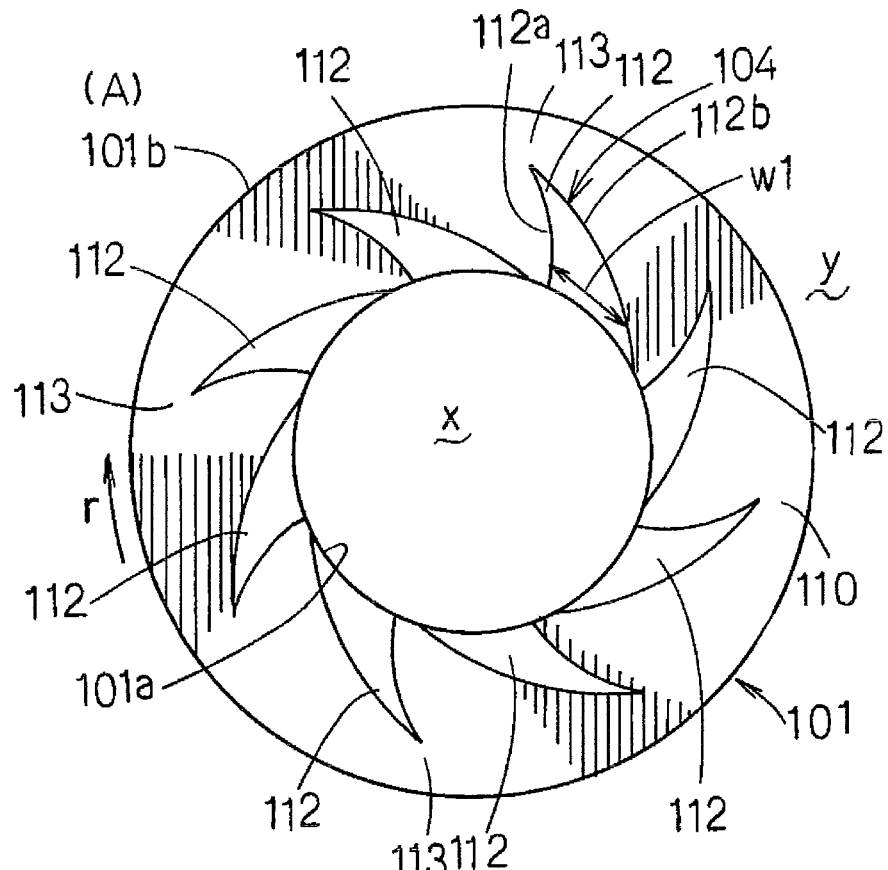
FIG. 19(A) is a plane view of a first processing member in the apparatus shown in FIG. 18.
FIG. 19(B) is a schematic vertical sectional view showing an important part thereof.
Figure 19:
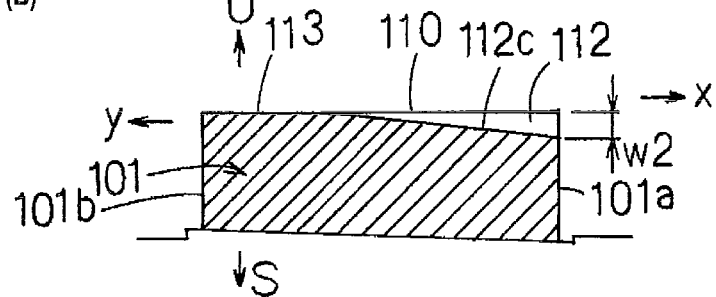
Figure 20:
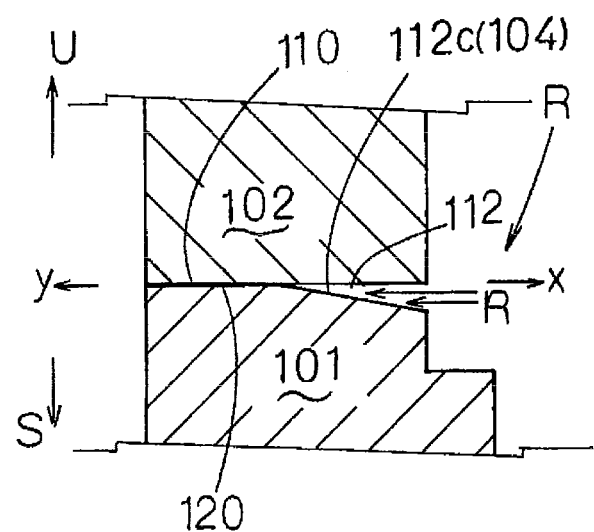
FIG. 20(A) is a schematic vertical sectional view showing an important part of first and second processing members in the apparatus shown in FIG. 18.
FIG. 20(B) is a schematic vertical sectional view showing an important part of the first and second processing members with a minute gap.
Figure 20:
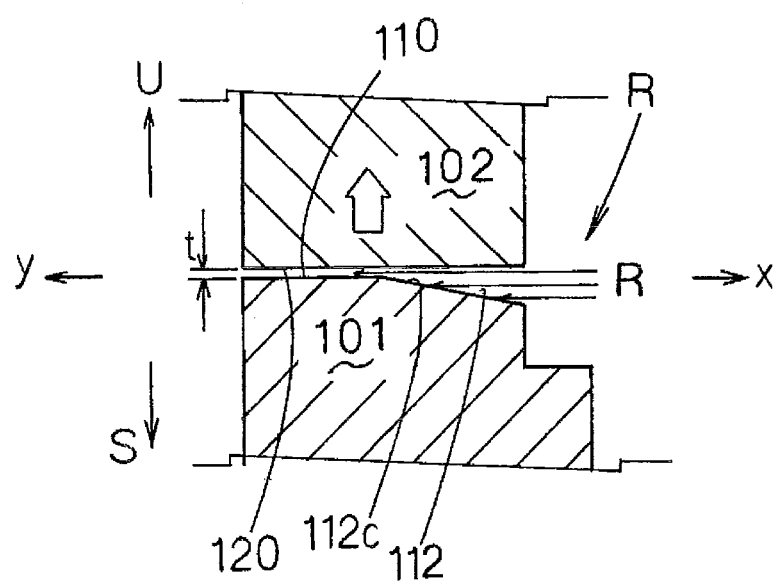

One embodiment of the processing apparatus is shown in FIG. 18 to FIG. 20. The processing apparatus illustrated in this embodiment is an apparatus including a mechanism of removing a liquid from the processed product thereby finally securing objective solids (crystals) only.

FIG. 18(A) is a schematic vertical sectional view of the processing apparatus, and FIG. 18(B) is its partially cut enlarged sectional view. FIG. 19 is a plane view of the first processing member 101 arranged in the processing apparatus in FIG. 18. FIG. 20 is a partially cut schematic vertical sectional view showing an important part of the first and second processing members 101 and 102 in the processing apparatus.

As described above, the apparatus shown in FIG. 18 to FIG. 20 is the one into which a fluid as the object of processing, that is, a processed fluid, or a fluid carrying the object of processing, is to be introduced at atmospheric pressure.

In FIG. 18(B) and FIG. 20, the second introduction part d2 is omitted for simplicity of the drawing (these drawings can be regarded as showing a section at the position where the second introduction part d2 is not arranged).

As shown in FIG. 18(A), this processing apparatus includes a reaction apparatus G and a decompression pump Q. This reaction apparatus G includes a first processing member 101 as a rotating member, a first holder 111 for holding the processing member 101, a second processing member 102 that is a member fixed to the case, a second holder 121 having the second processing member 102 fixed thereto, a bias mechanism 103, a dynamical pressure generating mechanism 104 (FIG. 19(A)), a drive part which rotates the first processing member 101 with the first holder 111, a housing 106, a first introduction part d1 which supplies (introduces) a first processed fluid, and a discharge part 108 that discharges the fluid to the decompression pump Q. The drive part is not shown.

The first processing member 101 and the second processing member 102 are cylindrical bodies that are hollow in the center. The processing members 101 and 102 are members wherein the bottoms of the processing members 101 and 102 in a cylindrical form are processing surfaces 110 and 120 respectively.

The processing surfaces 110 and 120 have a mirror-polished flat part. In this embodiment, the processing surface 120 of the second processing member 102 is a flat surface subjected as a whole to mirror polishing. The processing surface 110 of the first processing member 101 is a flat surface as a whole like the second processing member 102, but has a plurality of grooves 112 . . . 112 in the flat surface as shown in FIG. 19(A). The grooves 112 . . . 112 while centering on the first processing member 101 in a cylindrical form extend radially toward the outer periphery of the cylinder.

The processing surfaces 110 and 120 of the first and second processing members 101 and 102 are mirror-polished such that the surface roughness Ra comes to be in the range of 0.01 μm to 1.0 μm. By this mirror polishing, Ra is regulated preferably in the range of 0.03 μm to 0.3 μm.

The material for the processing members 101 and 102 is one which is rigid and capable of mirror polishing. The rigidity of the processing members 101 and 102 is preferably at least 1500 or more in terms of Vickers hardness. A material having a low linear expansion coefficient or high thermal conductance is preferably used. This is because when the difference in coefficient of expansion between a part which generates heat upon processing and other parts is high, distortion is generated and securement of suitable clearance is influenced.

As the material for the processing members 101 and 102, it is preferable to use particularly SIC, that is, silicon carbide, SIC having a Vickers hardness of 2000 to 2500, SIC having a Vickers hardness of 3000 to 4000 coated thereon with DLC (diamond-like carbon), WC, that is, tungsten carbide having a Vickers hardness of 1800, WC coated thereon with DLC, and boron ceramics represented by $ZrB_2$, BTC and $B_4C$ having a Vickers hardness of 4000 to 5000.

The housing 106 shown in FIG. 18, the bottom of which is not shown though, is a cylinder with a bottom, and the upper part thereof is covered with the second holder 121. The second holder 121 has the second processing member 102 fixed to the lower surface thereof, and the introduction part d1 is arranged in the upper part thereof. The introduction part d1 is provided with a hopper 170 for introducing a fluid or a processed material from the outside.

Although not shown in the figure, the drive part includes a power source such as a motor and a shaft 50 that rotates by receiving power from the power source.

As shown in FIG. 18(A), the shaft 50 is arranged in the housing 106 and extends vertically. Then, the first holder 111 is arranged on the top of the shaft 50. The first holder 111 is to hold the first processing member 101 and is arranged on the shaft 50 as described above, thereby allowing the processing surface 110 of the first processing member 101 to correspond to the processing surface 120 of the second processing member 102.

The first holder 111 is a cylindrical body, and the first processing member 101 is fixed on the center of the upper surface. The first processing member 101 is fixed so as to be integrated with the first holder 111, and does not change its position relative to the first holder 111.

On the other hand, a receiving depression 124 for receiving the second processing member 102 is formed on the center of the upper surface of the second holder 121.

The receiving depression 124 has a circular cross-section. The second processing member 102 is accepted in the cylindrical receiving depression 124 so as to be concentric with the receiving depression 124.

The structure of the receiving depression 124 is similar to that in the embodiment as shown in FIG. 1(A) (the first processing member 101 corresponds to the first ring 10, the first holder 111 to the first holder 11, the second processing member 102 to the second ring 20, and the second holder 121 to the second holder 21).

Then, the second holder 121 is provided with the bias mechanism 103. The bias mechanism 103 preferably uses an elastic body such as spring. The bias mechanism 103 corresponds to the surface-approaching pressure imparting mechanism 4 in FIG. 1(A) and has the same structure. That is, the bias mechanism 103 presses that side (bottom) of the second processing member 102 which is opposite to the processing surface 120 and biases each position of the second processing member 102 uniformly downward to the first processing member 101.

On the other hand, the inner diameter of the receiving depression 124 is made larger than the outer diameter of the second processing member 102, so that when arranged concentrically as described above, a gap t1 is arranged between outer periphery 102b of the second processing member 102 and inner periphery of the receiving depression 124, as shown in FIG. 18(B).

Similarly, a gap t2 is arranged between inner periphery 102a of the second processing member 102 and outer periphery of the central part 22 of the receiving depression 124, as shown in FIG. 18(B).

The gaps t1 and t2 are those for absorbing vibration and eccentric behavior and are set to be in a size to secure operational dimensions or more and to enable sealing. For example, when the diameter of the first processing member 101 is 100 mm to 400 mm, the gaps t1 and t2 are preferably 0.05 mm to 0.3 mm, respectively.

The first holder 111 is fixed integrally with the shaft 50 and rotated with the shaft 50. The second processing member 102 is not rotated relative to the second holder 121 by a baffle (not shown). However, for securing 0.1 micron to 10 micron clearance necessary for processing, that is, the minute gap t between the processing surfaces 110 and 120 as shown in FIG. 20(B), a gap t3 is arranged between the bottom of the receiving depression 124, that is, the top part, and the surface facing a top part 124a of the second processing member 102, that is, the upper part. The gap t3 is established in consideration of the clearance and the vibration and elongation of the shaft 150.

As described above, by the provision of the gaps t1 to t3, the second processing member 102 can move not only in the direction z1 of approaching to and separating from the first processing member 101, but also relative to the center and inclination, that is, the direction z2 of the processing surface 120.

That is, in this embodiment, the bias mechanism 103 and the gaps t1 to t3 constitute a floating mechanism, and by this floating mechanism, the center and inclination of at least the second processing member 102 are made variable in the small range of several μm to several mm. The run-out and expansion of the rotary shaft and the surface vibration and vibration of the first processing member 101 are absorbed.

The groove 112 on the processing surface 110 of the first processing member 101 is described in more detail. The rear end of the groove 112 reaches the inner periphery 101a of the first processing member 101, and its top is elongated toward the outside y of the first processing member 101, that is, toward the outer periphery. As shown in FIG. 19(A), the sectional area of the groove 112 is gradually decreased in the direction from the center x of the circular first processing member 101 to the outside y of the first processing member 101, that is, toward the outer periphery.

The distance w1 of the left and right sides 112a and 112b of the groove 112 is decreased in the direction from the center x of the first processing member 101 to the outside y of the first processing member 101, that is, toward the outer periphery. As shown in FIG. 19(B), the depth w2 of the groove 112 is decreased in the direction from the center x of the first processing member 101 to the outside y of the first processing member 101, that is, toward the outer periphery. That is, the bottom 112c of the groove 112 is decreased in depth in the direction from the center x of the first processing member 101 to the outside y of the first processing member 101, that is, toward the outer periphery.

As described above, the groove 112 is gradually decreased both in width and depth toward the outside y, that is, toward the outer periphery, and its sectional area is gradually decreased toward the outside y. Then, the top of the groove 112, that is, the y side, is a dead end. That is, the top of the groove 112, that is, the y side does not reach the outer periphery 101b of the first processing member 101, and an outer flat surface 113 is interposed between the top of the groove 112 and the outer periphery 101b. The outer flat surface 113 is a part of the processing surface 110.

In the embodiment shown in FIG. 19, the left and right sides 112a and 112b and the bottom 112c of the groove 112 constitute a flow path limiting part. This flow path limiting part, the flat part around the groove 112 of the first processing member 101, and the flat part of the second processing member 102 constitute the dynamical pressure generating mechanism 104.

However, only one of the width and depth of the groove 112 may be constituted as described above to decrease the sectional area.

While the first processing member 101 rotates, the dynamical pressure generating mechanism 104 generates a force in the direction of separating the processing members 101 and 102 from each other to secure a desired minute space between the processing members 101 and 102 by a fluid passing through the space between the processing members 101 and 102. By generation of such dynamical pressure, a 0.1 μm to 10 μm minute space can be generated between the processing surfaces 110 and 120. A minute space like that can be regulated and selected depending on the object of processing, but is preferably 1 μm to 6 μm, more preferably 1 μm to 2 μm. This apparatus can realize a uniform reaction and form microparticles by the minute space, which are not achieved in the prior art.

The grooves 112 . . . 112 may extend straight from the center x to the outside y. In this embodiment, however, as shown in FIG. 19(A), the grooves 112 are curved to extend such that with respect to a rotation direction r of the first processing member 101, the center x of the groove 112 is positioned in front of the outside y of the groove 112.

In this manner, the grooves 112 . . . 112 are curved to extend so that the separation force by the dynamical pressure generating mechanism 104 can be effectively generated.

Then, the working of this apparatus is described.

A first processed fluid R which has been introduced from a hopper 170 and has passed through the first introduction part d1, passes through the hollow part of the circular second processing member 102, and the first processed fluid R that has received the centrifugal force resulting from rotation of the first processing member 101 enters the space between the processing members 101 and 102, and uniform reaction and generation of microparticles are effected and processed between the processing surface 110 of the rotating first processing member 101 and the processing surface 120 of the second processing member 102, then exits from the processing members 101 and 102 and is then discharged from the discharge part 108 to the side of the decompression pump Q. Hereinafter, the first processed fluid R is referred to simply as a fluid R, if necessary.

In the foregoing description, the fluid R that has entered the hollow part of the circular second processing member 102 first enters the groove 112 of the rotating first processing member 101 as shown in FIG. 20(A). On the other hand, the processing surfaces 110 and 120 that are mirror-polished flat parts are kept airtight even by passing a gas such as air or nitrogen. Accordingly, even if the centrifugal force by rotation is received, the fluid cannot enter through the groove 112 into the space between the processing surfaces 110 and 120 that are pushed against each other by the bias mechanism 103. However, the fluid R gradually runs against both the sides 112a and 112b and the bottom 112c of the groove 112 formed as a flow path limiting part to generate dynamical pressure acting in the direction of separating the processing surfaces 110 and 120 from each other. As shown in FIG. 20(B), the fluid R can thereby exude from the groove 112 to the flat surface, to secure a minute gap t, that is, clearance, between the processing surfaces 110 and 120. Then, a uniform reaction and generation of microparticles are effected and processed between the mirror-polished flat surfaces. The groove 112 has been curved so that the centrifugal force is applied more accurately to the fluid to make generation of dynamical pressure more effectively.

In this manner, the processing apparatus can secure a minute and uniform gap, that is, clearance, between the mirror surfaces, that is, the processing surfaces 110 and 120, by the balance between the dynamical pressure and the bias force by the bias mechanism 103. By the structure described above, the minute gap can be as superfine as 1 μm or less.

By utilizing the floating mechanism, the automatic regulation of alignment between the processing surfaces 110 and 120 becomes possible, and the clearance in each position between the processing surfaces 110 and 120 can be prevented from varying against physical deformation of each part by rotation or generated heat, and the minute gap in each position can be maintained.

In the embodiment described above, the floating mechanism is a mechanism arranged for the second holder 121 only. Alternatively, the floating mechanism can be arranged in the first holder 111 instead of, or together with, the second holder 121.

Figure 21:
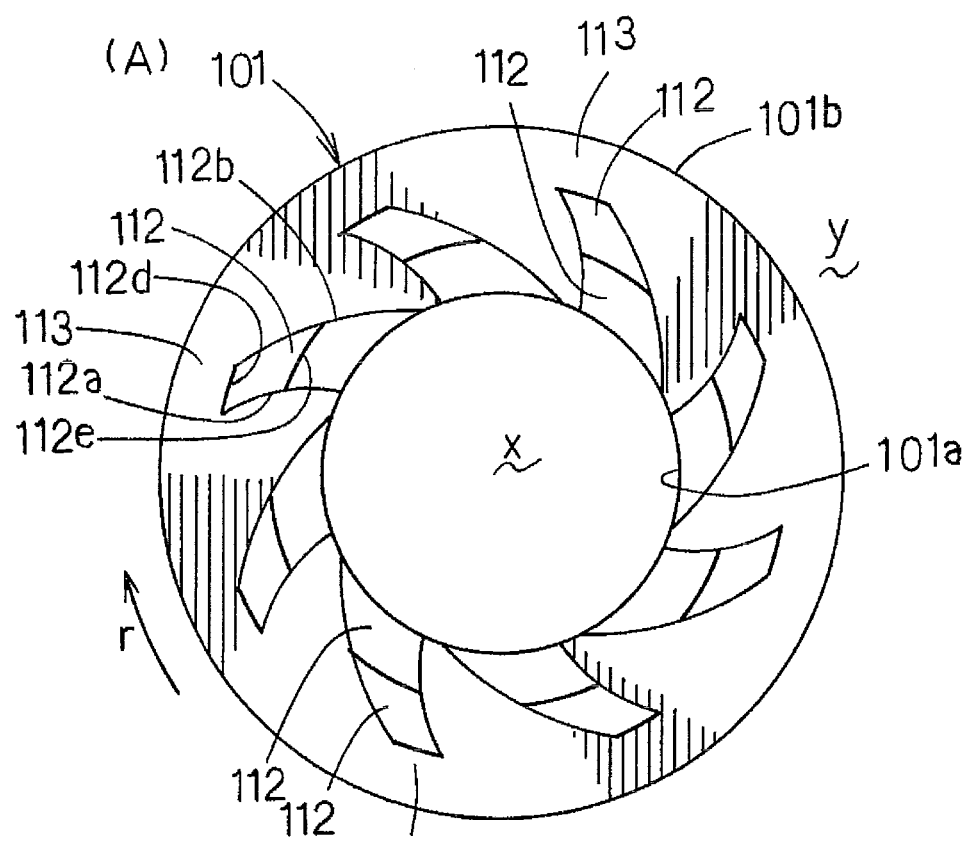
FIG. 21(A) is a plane view of another embodiment of the first processing member.
FIG. 21(B) is a schematic vertical sectional view showing an important part thereof.
Figure 21:
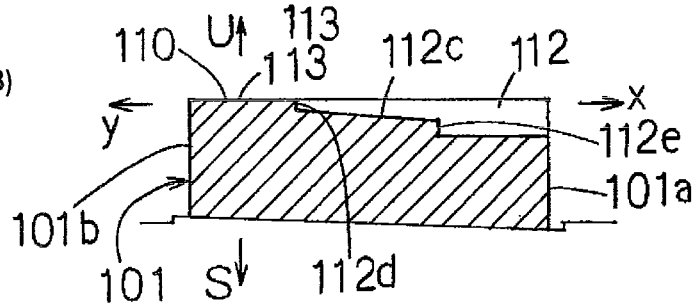
Figure 22:
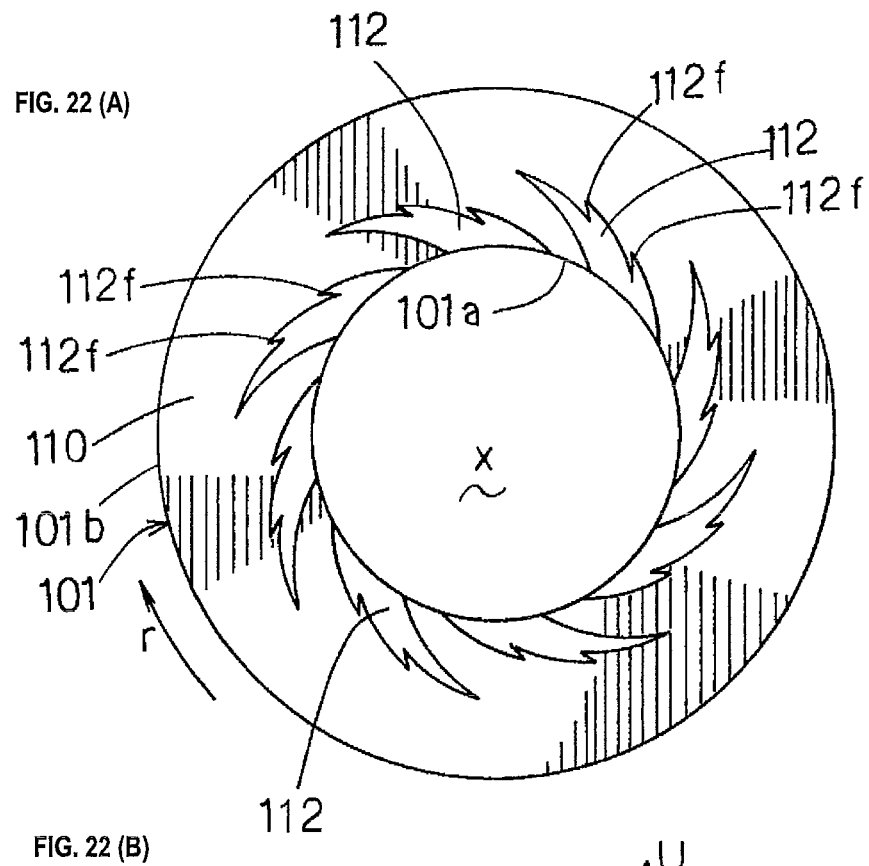
FIG. 22(A) is a plane view of still another embodiment of the first processing member.
FIG. 22(B) is a schematic vertical sectional view showing an important part thereof.
Figure 22:
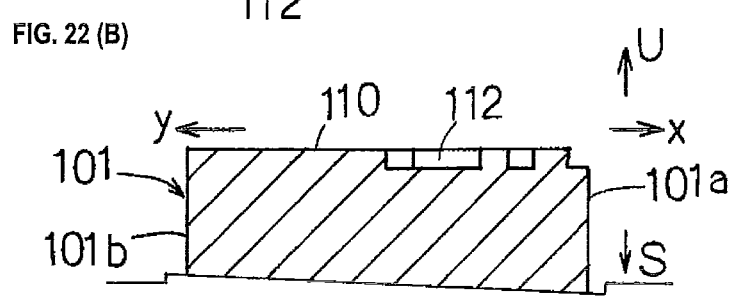
Figure 23:
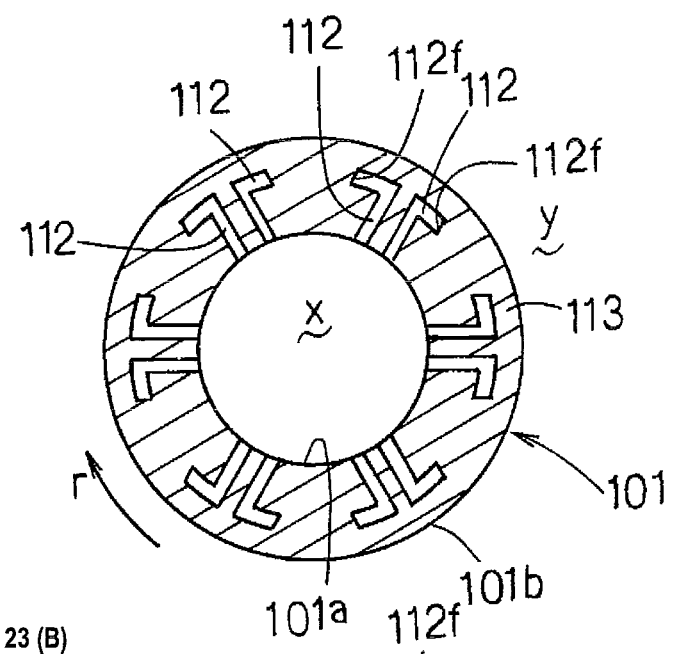
FIG. 23(A) is a plane view of still another embodiment of the first processing member.
FIG. 23(B) is a plane view of still another embodiment of the first processing member.
Figure 23:
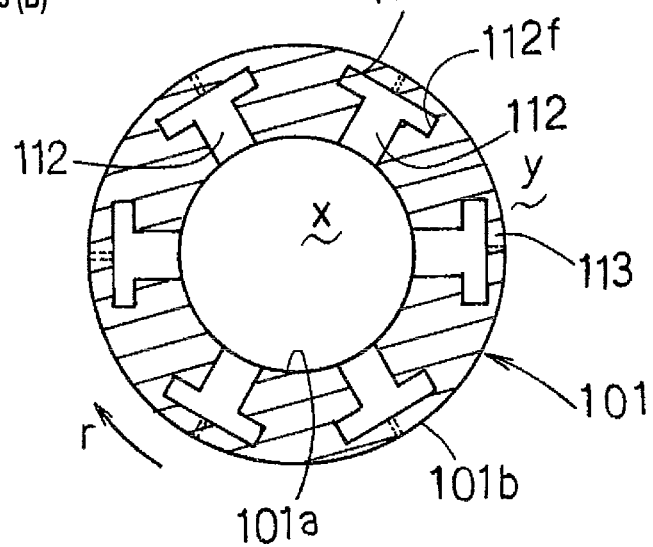

Other embodiments of the groove 112 are shown in FIG. 21 to FIG. 23.

As shown in FIG. 21(A) and FIG. 21(B), the groove 112 can be provided at the top with a flat wall surface 112d as a part of the flow path limiting part. In this embodiment, a step 112e is arranged between the first wall surface 112d and the inner periphery 101a in the bottom 112c, and the step 112e also constitutes a part of the flow path limiting part.

As shown in FIG. 22(A) and FIG. 22(B), the groove 112 includes a plurality of branches 112f . . . 112f, and each branch 112f narrows its width thereby being provided with a flow path limiting part.

With respect to the embodiments as well, structures other than those particularly shown are similar to those of embodiments as shown in FIG. 1(A), FIG. 11(C), and FIG. 18 to FIG. 20.

In the embodiments described above, at least either the width or depth of the groove 112 is gradually decreased in size in the direction from inside to outside the first processing member 101, thereby constituting a flow path limiting part. Alternatively, as shown in FIG. 23(A) or FIG. 23(B), the groove 112 can be provided with a termination surface 112f without changing the width and depth of the groove 112, and the termination surface 112f of the groove 112 can serve as a flow path limiting part. As shown the embodiments in FIG. 19, FIG. 21 and FIG. 22, the width and depth of the groove 112 can be changed as described above thereby slanting the bottom and both sides of the groove 112, so that the slanted surfaces serves as a pressure-receiving part toward the fluid to generate dynamical pressure. In the embodiment shown in FIG. 23(A) and FIG. 23(B), on the other hand, the termination surface of the groove 112 serves as a pressure-receiving part toward the fluid to generate dynamical pressure.

In the embodiment shown in FIG. 23(A) and FIG. 23(B), at least one of the width and depth of the groove 112 may also be gradually decreased in size.

The structure of the groove 112 is not limited to the one shown in FIG. 19 and FIG. 21 to FIG. 23 and can be provided with a flow path limiting part having other shapes.

For example, in the embodiments shown in FIG. 19 and FIG. 21 to FIG. 23, the groove 112 does not penetrate to the outer side of the first processing member 101. That is, there is an outer flat surface 113 between the outer periphery of the first processing member 101 and the groove 112. However, the structure of the groove 112 is not limited to such embodiment, and the groove 112 may reach the outer periphery of the first processing member 101 as long as the dynamical pressure can be generated.

For example, in the case of the first processing member 101 shown in FIG. 23(B), as shown in the dotted line, a part having a smaller sectional area than other sites of the groove 112 can be formed on the outer flat surface 113.

The groove 112 may be formed so as to be gradually decreased in size in the direction from inside to outside as described above, and the part (terminal) of the groove 112 that had reached the outer periphery of the first processing member 101 may have the minimum sectional area (not shown). However, the groove 112 preferably does not penetrate to the outer periphery of the first processing member 101 as shown in FIG. 19 and FIG. 21 to FIG. 23, in order to effectively generate dynamical pressure.

Now, the embodiments shown in FIG. 18 to FIG. 23 are summarized.

This processing apparatus is a processing apparatus wherein a rotating member having a flat processing surface and a fixed member having a flat processing surface are opposite to each other so as to be concentric with each other, and while the rotating member is rotated, a material to be reacted is fed through an opening of the fixed member and subjected to a reaction between the opposite flat processing surfaces of both members, wherein the rotating member is provided with a pressurizing mechanism by which pressure is generated to maintain clearance without mechanically regulating clearance and enables 1 μm to 6 μm microscopic clearance not attainable by mechanical regulation of clearance, thereby significantly improving an ability to atomize formed particles and an ability to uniformize the reaction.

That is, this processing apparatus have a rotating member and a fixed member each having a flat processing surface in the outer periphery thereof and has a sealing mechanism in a plane on the flat processing surface, thereby providing a high speed rotation processing apparatus generating hydrostatic force, hydrodynamic force, or aerostatic-aerodynamic force. The force generates a minute space between the sealed surfaces, and provides a reaction processing apparatus with a function of non-contact and mechanically safe and high-level pulvelization and uniformizing of reactions. One factor for forming this minute space is due to the rotation speed of the rotating member, and the other factor is due to a pressure difference between the introduction side and discharge side of a processed material (fluid). When a pressure imparting mechanism is not arranged in the introduction side, that is, when the processed material (fluid) is introduced at atmospheric pressure, there is no pressure difference, and thus the sealed surfaces should be separated by only the rotation speed of the rotating member. This is known as hydrodynamic or aerodynamic force.

Figure 24:
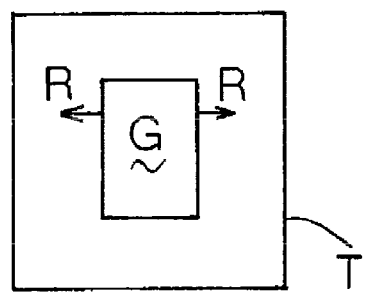
FIG. 24(A), FIG. 24(B) and FIG. 24(C) are diagrams showing embodiments other than those described above with respect to the method of separating a processed material after processing.
Figure 24:
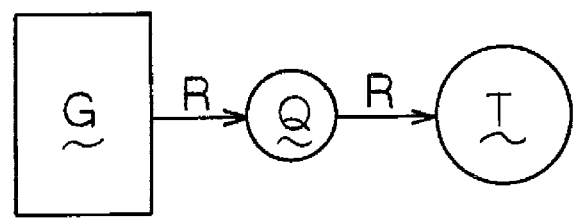
Figure 24:
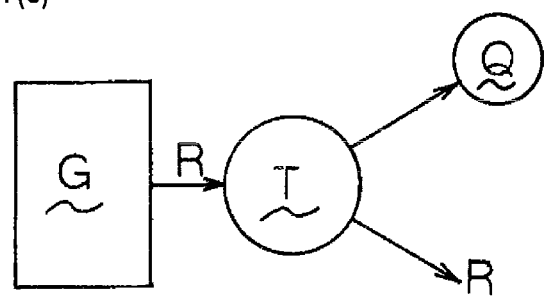

FIG. 18(A) shows the apparatus wherein a decompression pump Q is connected to the discharge part of the reaction apparatus G, but as described above, the reaction apparatus G may be arranged in a decompression tank T without arranging the housing 106 and the decomposition pump Q, as shown in FIG. 24(A).

In this case, the tank T is decompressed in a vacuum or in an almost vacuum, whereby the processed product formed in the reaction apparatus G is sprayed in a mist form in the tank T, and the processed material colliding with, and running down along, the inner wall of the tank T can be recovered, or a gas (vapor) separated from the processed material and filled in an upper part of the tank T, unlike the processed material running down along the wall, can be recovered to obtain the objective product after processing.

When the decompression pump Q is used, an airtight tank T is connected via the decompression pump Q to the processing apparatus G, whereby the processed material after processing can be formed into mist to separate and extract the objective product.

As shown in FIG. 24(C), the decompression pump Q is connected directly to the tank T, and the decompression pump Q and a discharge part for fluid R, different from the decompression pump Q, are connected to the tank T, whereby the objective product can be separated. In this case, a gasified portion is sucked by the decompression pump Q, while the fluid R (liquid portion) is discharged from the discharge part separately from the gasified portion.

In the embodiments described above, the first and second processed fluids are introduced via the second holders 21 and 121 and the second rings 20 and 102 respectively and mixed and reacted with each other.

Now, other embodiments with respect to introduction of fluids to be processed into the apparatus are described.

As shown in FIG. 1(B), the processing apparatus shown in FIG. 1(A) is provided with a third introduction part d3 to introduce a third fluid to be processed into the space between the processing surfaces 1 and 2, and the third fluid is mixed and reacted with the first processed fluid as well as the second processed fluid.

By the third introduction part d3, the third fluid to be mixed with the first processed fluid is fed to the space between the processing surfaces 1 and 2. In this embodiment, the third introduction part d3 is a fluid flow path arranged in the second ring 20 and is open at one end to the second processing surface 2 and has a third fluid feed part p3 connected to the other end.

In the third fluid feed part p3, a compressor or another pump can be used.

The opening of the third introduction part d3 in the second processing surface 2 is positioned outside, and more far from, the rotation center of the first processing surface 1 than the opening of the second introduction part d2. That is, in the second processing surface 2, the opening of the third introduction part d3 is located downstream from the opening of the second introduction part d2. A gap is arranged between the opening of the third introduction d3 and the opening of the second introduction part d2 in the radial direction of the second ring 20.

With respect to structures other than the third introduction d3, the apparatus shown in FIG. 1(B) is similar to that in the embodiment as in FIG. 1(A). In FIG. 1(B) and further in FIG. 1(C), FIG. 1(D) and FIG. 2 to FIG. 11 described later, the case 3 is omitted to simplify the drawings. In FIG. 9(B), FIG. 9(C), FIG. 10, FIG. 11(A) and FIG. 11(B), a part of the case 3 is shown.

As shown in FIG. 1(C), the processing apparatus shown in FIG. 1(B) is provided with a fourth introduction part d4 to introduce a fourth fluid to be processed into the space between the processing surfaces 1 and 2, and the fourth fluid is mixed and reacted with the first processed fluid as well as the second and third processed fluids.

By the fourth introduction part d4, the fourth fluid to be mixed with the first processed fluid is fed to the space between the processing surfaces 1 and 2. In this embodiment, the fourth introduction part d4 is a fluid flow path arranged in the second ring 20, is open at one end to the second processing surface 2, and has a fourth fluid feed part p4 connected to the other end.

In the fourth fluid feed part p4, a compressor or another pump can be used.

The opening of the fourth introduction part d4 in the second processing surface 2 is positioned outside, and more far from, the rotation center of the first processing surface 1 than the opening of the third introduction part d3. That is, in the second processing surface 2, the opening of the fourth introduction part d4 is located downstream from the opening of the third introduction part d3.

With respect to structures other than the fourth introduction part d4, the apparatus shown in FIG. 1(C) is similar to that in the embodiment as in FIG. 1(B).

Five or more introduction parts further including a fifth introduction part, a sixth introduction part and the like can be arranged to mix and react five or more fluids to be processed with one another (not shown).

As shown in FIG. 1(D), the first introduction part d1 arranged in the second holder 21 in the apparatus in FIG. 1(A) can, similar to the second introduction part d2, be arranged in the second processing surface 2 in place of the second holder 21. In this case, the opening of the first introduction part d1 is located at the upstream side from the second introduction part d2, that is, it is positioned nearer to the rotation center than the second introduction part d2 in the second processing surface 2.

In the apparatus shown in FIG. 1(D), the opening of the second introduction part d2 and the opening of the third introduction part d3 both are arranged in the second processing surface 2 of the second ring 20. However, arrangement of the opening of the introduction part is not limited to such arrangement relative to the processing surface. Particularly as shown in FIG. 2(A), the opening of the second introduction part d2 can be arranged in a position adjacent to the second processing surface 2 in the inner periphery of the second ring 20. In the apparatus shown in FIG. 2(A), the opening of the third introduction part d3 is arranged in the second processing surface 2 similarly to the apparatus shown in FIG. 1(B), but the opening of the second introduction part d2 can be arranged inside the second processing surface 2 and adjacent to the second processing surface 2, whereby the second processed fluid can be immediately introduced onto the processing surfaces.

In this manner, the opening of the first introduction part d1 is arranged in the second holder 21, and the opening of the second introduction part d2 is arranged inside the second processing surface 2 and adjacent to the second processing surface 2 (in this case, arrangement of the third introduction part d3 is not essential), so that particularly in reaction of a plurality of fluids, the fluid introduced from the first introduction part d1 and the fluid introduced from the second introduction part d2 are introduced, without being reacted with each other, into the space between the processing surfaces 1 and 2, and then both the fluids can be reacted first between the processing surfaces 1 and 2. Accordingly, the structure described above is suitable for obtaining a particularly reactive fluid.

The term "adjacent" is not limited to the arrangement where the opening of the second introduction part d2 is contacted with the inner side of the second ring 20 as shown in FIG. 2(A). The distance between the second ring 20 and the opening of the second introduction part d2 may be such a degree that a plurality of fluids are not completely mixed and reacted with one another prior to introduction into the space between the processing surfaces 1 and 2. For example, the opening of the second introduction part d2 may be arranged in a position near the second ring 20 of the second holder 21.

Alternatively, the opening of the second introduction part d2 may be arranged on the side of the first ring 10 or the first holder 11.

In the apparatus shown in FIG. 1(B), a gap is arranged between the opening of the third introduction part d3 and the opening of the second introduction part d2 in the radial direction of the second ring 20, but as shown in FIG. 2(B), the second and third fluids can be introduced into the space between the processing surfaces 1 and 2, without providing such gap, thereby immediately joining both the fluids together. The apparatus shown in FIG. 2(B) can be selected depending on the object of processing.

In the apparatus shown in FIG. 1(D), a gap is also arranged between the opening of the first introduction part d1 and the opening of the second introduction part d2 in the radial direction of the second ring 20, but the first and second fluids can be introduced into the space between the processing surfaces 1 and 2, without providing such gap, thereby immediately joining both the fluids together. Such arrangement of the opening can be selected depending on the object of processing.

In the embodiment shown in FIG. 1(B) and FIG. 1(C), the opening of the third introduction part d3 is arranged in the second processing surface 2 downstream from the opening of the second introduction part d2, in other words, outside the opening of the second introduction part d2 in the radial direction of the second ring 20. Alternatively, as shown in FIG. 2(C) and FIG. 3(A), the opening of the third introduction part d3 and the opening of the second introduction part d2 can be arranged in the second processing surface 2 in positions different in a circumferential direction r0 of the second ring 20. In FIG. 3, numeral m1 is the opening (first opening) of the first introduction part d1, numeral m2 is the opening (second opening) of the second introduction part d2, numeral m3 is the opening (third opening) of the third introduction part d3, and numeral r1 is the radical direction of the ring.

When the first introduction part d1 is arranged in the second ring 20, as shown in FIG. 2(D), the opening of the first introduction part d1 and the opening of the second introduction part d2 can be arranged in the second processing surface 2 in positions different in the circumferential direction of the second ring 20.

In the apparatus shown in FIG. 2(C), the openings of two introduction parts are arranged in the second processing surface 2 of the second ring 20 in positions different in the circumferential direction r0, but as shown in FIG. 3(B), the openings of three introduction parts can be arranged in positions different in the circumferential direction r0 of the ring, or as shown in FIG. 3(C), the openings of four introduction parts can be arranged in positions different in the circumferential direction r0 of the ring. In FIG. 3(B) and FIG. 3(C), numeral m4 is the opening of the fourth introduction part, and in FIG. 3(C), numeral m5 is the opening of the fifth introduction part. Five or more openings of introduction parts may be arranged in positions different in the circumferential direction r0 of the ring (not shown).

In the apparatuses shown in FIG. 2(B), FIG. 2(D) and in FIG. 3(A) to FIG. 3(C), the second to fifth introduction parts can introduce different fluids, that is, the second, third, fourth and fifth fluids. On the other hand, the second to fifth openings m2 to m5 can introduce the same fluid, that is, the second fluid into the space between the processing surfaces. In this case, the second to fifth introduction parts are connected to the inside of the ring and can be connected to one fluid feed part, that is, the second fluid feed part p2 (not shown).

A plurality of openings of introduction parts arranged in positions different in the circumferential direction r0 of the ring can be combined with a plurality of openings of introduction parts arranged in positions different in the radial direction r1 of the ring.

For example, as shown in FIG. 3(D), the openings m2 to m9 of eight introduction parts are arranged in the second processing surface 2, wherein four openings m2 to m5 of them are arranged in positions different in the circumferential direction r0 of the ring and identical in the radial direction r1 of the ring, and the other four openings m6 to m9 are arranged in positions different in the circumferential direction r0 of the ring and identical in the radial direction r1 of the ring. Then, the other openings m6 to m9 are arranged outside the radial direction r1 of the four openings m2 to m5. The outside openings and inside openings may be arranged in positions identical in the circumferential direction r0 of the ring, but in consideration of rotation of the ring, may be arranged in positions different in the circumferential direction r0 of the ring as shown in FIG. 3(D). In this case too, the openings are not limited to arrangement and number shown in FIG. 3(D).

For example, as shown in FIG. 3(E), the outside opening in the radial direction can be arranged in the apex of a polygon, that is, in the apex of a rectangle in this case, and the inside opening in the radial direction can be positioned on one side of the rectangle. As a matter of course, other arrangements can also be used.

When the openings other than the first opening m1 feed the second fluid into the space between the processing surfaces, each of the openings may be arranged as continuous openings in the circumferential direction r0 as shown in FIG. 3(F), instead of being arranged discretely in the circumferential direction r0 of the processing surface.

As shown in FIG. 4(A), depending on the object of processing, the second introduction part d2 arranged in the second ring 20 in the apparatus shown in FIG. 1(A) can be, similar to the first introduction part d1, arranged in the central portion 22 of the second holder 21. In this case, the opening of the second introduction part d2 is positioned with a gap outside the opening of the first introduction part d1 positioned in the center of the second ring 20. As shown in FIG. 4(B), in the apparatus shown in FIG. 4(A), the third introduction part d3 can be arranged in the second ring 20. As shown in FIG. 4(C), in the apparatus shown in FIG. 4(A), the first and second processed fluids can be introduced into the space inside the second ring 20 without arranging a gap between the opening of the first introduction part d1 and the opening of the second introduction part d2, so that both the fluids can immediately join together. As shown in FIG. 4(D), depending on the object of processing, in the apparatus shown in FIG. 4(A), the third introduction part d3 can be, similar to the second introduction part d2, arranged in the second holder 21. Four or more introduction parts may be arranged in the second holder 21 (not shown).

As shown in FIG. 5(A), depending on the object of processing, in the apparatus shown in FIG. 4(D), the fourth introduction part d4 can be arranged in the second ring 20, so that the fourth fluid may be introduced into the space between the processing surfaces 1 and 2.

As shown in FIG. 5(B), in the apparatus shown in FIG. 1(A), the second introduction part d2 can be arranged in the first ring 10, and the opening of the second introduction part d2 can be arranged in the first processing surface 1.

As shown in FIG. 5(C), in the apparatus shown in FIG. 5(B), the third introduction part d3 can be arranged in the first ring 10, and the opening of the third introduction part d3 and the opening of the second introduction part d2 can be arranged in the first processing surface 1 in positions different in the circumferential direction of the first ring 10.

As shown in FIG. 5(D), in the apparatus shown in FIG. 5(B), the first introduction part d1 can be arranged in the second ring 20 instead of arranging the first introduction part d1 in the second holder 21, and the opening of the first introduction part d1 can be arranged in the second processing surface 2. In this case, the openings of the first and second introduction parts d1 and d2 are arranged in positions identical in the radial direction of the ring.

As shown in FIG. 6(A), in the apparatus shown in FIG. 1(A), the third introduction part d3 can be arranged in the first ring 10, and the opening of the third introduction part d3 can be arranged in the first processing surface 1. In this case, both the openings of the second and third introduction parts d2 and d3 are arranged in positions identical in the radial direction of the ring. However, both the openings may be arranged in positions different in the radial direction of the ring.

In the apparatus shown in FIG. 5(C), both the openings of the second and third introduction parts d2 and d3 are arranged in positions identical in the radial direction of the first ring 10 and simultaneously arranged in positions different in the circumferential direction (that is, rotation direction) of the first ring 10, but in this apparatus, as shown in FIG. 6(B), both the openings of the second and third introduction parts d2 and d3 can be arranged in positions different in the radical direction of the first ring 10. In this case, as shown in FIG. 6(B), a gap can be arranged between both the openings of the second and third introduction parts d2 and d3 in the radial direction of the first ring 10, or without arranging the gap, the second and third fluids may immediately join together (not shown).

As shown in FIG. 6(C), the first introduction part d1 together with the second introduction part d2 can be arranged in the first ring 10 instead of arranging the first introduction part d1 in the second holder 21. In this case, in the first processing surface 1, the opening of the first introduction part d1 is arranged upstream (inside the radial direction of the first ring 10) from the opening of the second introduction part d2. A gap is arranged between the opening of the first introduction part d1 and the opening of the second introduction part d2 in the radial direction of the first ring 10. Alternatively, such gap may not be arranged (not shown).

As shown in FIG. 6(D), both the openings of the first introduction part d1 and the second introduction part d2 can be arranged in positions different in the circumferential direction of the first ring 10 in the first processing surface 1 in the apparatus shown in FIG. 6(C).

In the embodiment shown in FIG. 6(C) and FIG. 6(D), three or more introduction parts may be arranged in the first ring 10, and in the second processing surface 2, so the respective openings may be arranged in positions different in the circumferential direction or in positions different in the radial direction of the ring (not shown). For example, the arrangement of openings in the second processing surface 2, shown in FIG. 3(B) to FIG. 3(F), can also be used in the first processing surface 1.

As shown in FIG. 7(A), in the apparatus shown in FIG. 1(A), the second introduction part d2 can be arranged in the first holder 11 instead of arranging the part d2 in the second ring 20. In this case, the opening of the second introduction part d2 is arranged preferably in the center of the central shaft of rotation of the first ring 10, in the site surrounded with the first ring 10 on the upper surface of the first holder 11.

As shown in FIG. 7(B), in the embodiment shown in FIG. 7(A), the third introduction part d3 can be arranged in the second ring 20, and the opening of the third introduction part d3 can be arranged in the second processing surface 2.

As shown in FIG. 7(C), the first introduction part d1 can be arranged in the first holder 11 instead of arranging the part d1 in the second holder 21. In this case, the opening of the first introduction part d1 is arranged preferably in the central shaft of rotation of the first ring 10, in the site surrounded with the first ring 10 on the upper surface of the first holder 11. In this case, as shown in the figure, the second introduction part d2 can be arranged in the first ring 10, and its opening can be arranged in the first processing surface 1. In this case, the second introduction part d2 can be arranged in the second ring 20, and its opening can be arranged in the second processing surface 2 (not shown).

As shown in FIG. 7(D), the second introduction part d2 shown in FIG. 7(C) together with the first introduction part d1 can be arranged in the first holder 11. In this case, the opening of the second introduction part d2 is arranged in the site surrounded with the first ring 10 on the upper surface of the first holder 11. In this case, the second introduction part d2 arranged in the second ring 20 may serve as the third introduction part d3 in FIG. 7(C).

In the embodiments shown in FIG. 1 to FIG. 7, the first holder 11 and the first ring 10 are rotated relative to the second holder 21 and the second ring 20, respectively. As shown in FIG. 8(A), in the apparatus shown in FIG. 1(A), the second holder 21 may be provided with a rotary shaft 51 rotating with the turning force from the rotation drive member, to rotate the second holder 21 in a direction opposite to the first holder 11. The rotation drive member may be arranged separately from the one for rotating the rotary shaft 50 of the first holder 11 or may receive power from the drive part for rotating the rotary shaft 50 of the first holder 11 by a power transmission means such as a gear. In this case, the second holder 21 is formed separately from the case, and shall, like the first holder 11, be rotatably accepted in the case.

As shown in FIG. 8(B), in the apparatus shown in FIG. 8(A), the second introduction part d2 can be, similarly in the apparatus in FIG. 7(B), arranged in the first holder 11 in place of the second ring 20.

In the apparatus shown in FIG. 8(B), the second introduction part d2 can be arranged in the second holder 21 in place of the first holder 11 (not shown). In this case, the second introduction part d2 is the same as one in the apparatus in FIG. 4(A). As shown in FIG. 8(C), in the apparatus shown in FIG. 8(B), the third introduction part d3 can be arranged in the second ring 20, and the opening of the third introduction part d3 can be arranged in the second processing surface 2.

As shown in FIG. 8(D), the second holder 21 only can be rotated without rotating the first holder 11. Even in the apparatuses shown in FIG. 1(B) to FIG. 7, the second holder 21 together with the first holder 11, or the second holder 21 alone, can be rotated (not shown).

As shown in FIG. 9(A), the second processing member 20 is a ring, while the first processing member 10 is not a ring and can be a rotating member provided directly with a rotary shaft 50 similar to that of the first holder 11 in other embodiments. In this case, the upper surface of the first processing member 10 serves as the first processing surface 1, and the processing surface is an evenly flat surface which is not circular (that is, hollow-free). In the apparatus shown in FIG. 9(A), similarly in the apparatus in FIG. 1(A), the second introduction part d2 is arranged in the second ring 20, and its opening is arranged in the second processing surface 2.

As shown in FIG. 9(B), in the apparatus shown in FIG. 9(A), the second holder 21 is independent of the case 3, and a surface-approaching pressure imparting mechanism 4 such as an elastic body for approaching to and separating from the first processing member 10 can be provided between the case 3 and the second holder 21. In this case, as shown in FIG. 9(C), the second processing member 20 is not a ring, but is a member corresponding to the second holder 21, and the lower surface of the member can serve as the second processing surface 2. As shown in FIG. 10(A), in the apparatus shown in FIG. 9(C), the first processing member 10 is not a ring either, and in other embodiments similarly in the apparatus shown in FIG. 9(A) and FIG. 9(B), the site corresponding to the first holder 11 can serve as the first processing member 10, and its upper surface can serve as the first processing surface 1.

In the embodiments described above, at least the first fluid is supplied from the first processing member 10 and the second processing member 20, that is, from the central part of the first ring 10 and the second ring 20, and after processing (mixing and reaction) of the other fluids, the processed fluid is discharged to the outside in the radial direction.

Alternatively, as shown in FIG. 10(B), the first fluid can be supplied in the direction from the outside to the inside of the first ring 10 and second ring 20. In this case, the outside of the first holder 11 and the second holder 21 is sealed with the case 3, the first introduction part d1 is arranged directly in the case 3, and the opening of the introduction part is arranged in a site inside the case and corresponding to the abutting position of the rings 10 and 20, as shown in the figure. In the apparatus in FIG. 1(A), a discharge part 36 is arranged in the position in which the first introduction part d1 is arranged, that is, in the central position of the ring 1 of the first holder 11. The opening of the second introduction part d2 is arranged in the opposite side of the opening of the case behind the central shaft of rotation of the holder. However, the opening of the second introduction part d2 may be, similar to the opening of the first introduction part d1, arranged in a site inside the case and corresponding to the abutting position of the rings 10 and 20. As described above, the embodiment is not limited to the one where the opening of the second introduction part d2 is formed to the opposite side of the opening of the first introduction part d1.

A discharge part 36 for the product after processing is arranged. In this case, the outside of the diameter of both rings 10 and 20 is on the upstream side, and the inside of both the rings 10 and 20 is on the downstream side.

As shown in FIG. 10(C), in the apparatus shown in FIG. 10(B), the second introduction part d2, which is arranged in the side of the case 3, can be arranged in the first ring 10 in space of the mentioned position, and its opening can be arranged in the first processing surface 1. In this case, as shown in FIG. 10(D), the first processing member 10 is not formed as a ring. Similarly in the apparatuses shown in FIG. 9(A), FIG. 9(B) and FIG. 10(A), in other embodiments, the site corresponding to the first holder 11 is the first processing member 10, its upper surface being the first processing surface 1, the second introduction part d2 being arranged in the first processing member 10, and its opening may be arranged in the first processing surface 1.

Figure 11A:
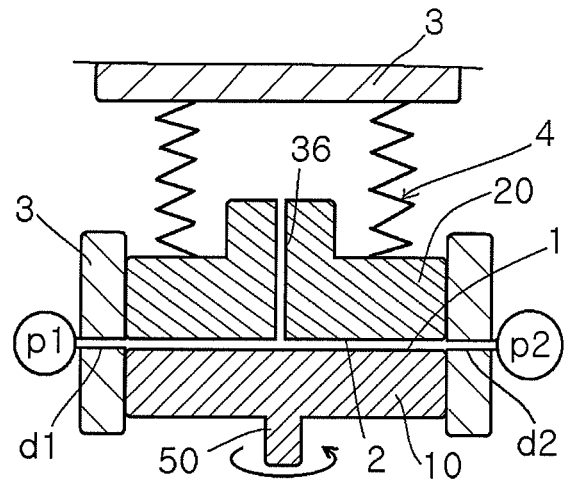
FIG. 11(A) and FIG. 11(B) each show a schematic vertical sectional view showing the concept of still another embodiment of the apparatus shown in FIG. 1.

As shown in FIG. 11(A), in the apparatus shown in FIG. 10(D), the second processing member 20 is not formed as a ring, and in other embodiments, the member corresponding to the second holder 21 serves as the second processing member 20, and its lower surface serves as the second processing surface 2. Then, the second processing member 20 is a member independent of the case 3, and the same surface-approaching pressure imparting mechanism 4 as one in the apparatuses shown in FIG. 9(B), FIG. 9(C) and FIG. 10(A) can be arranged between the case 3 and the second processing member 20.

Figure 11B:
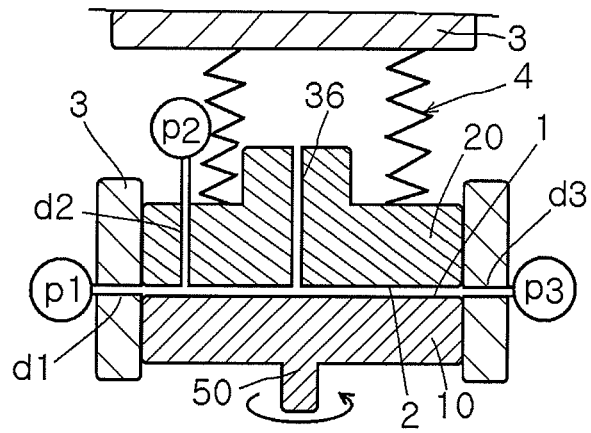
Figure 11C:
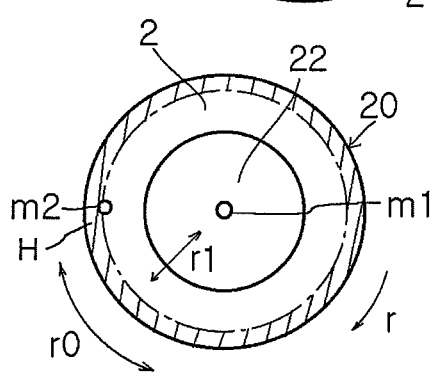
FIG. 11(C) is a schematic bottom view showing an important part of the apparatus shown in FIG. 1(A).

As shown in FIG. 11(B), the second introduction part d2 in the apparatus shown in FIG. 11(A) serves as the third introduction part d3, and separately the second introduction part d2 can be arranged.

Figure 4:
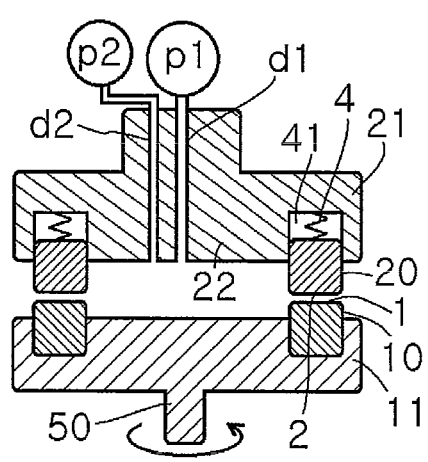
FIG. 4(A) to FIG. 4(D) each show a schematic vertical sectional view showing the concept of still another embodiment of the apparatus shown in FIG. 1.
Figure 4:
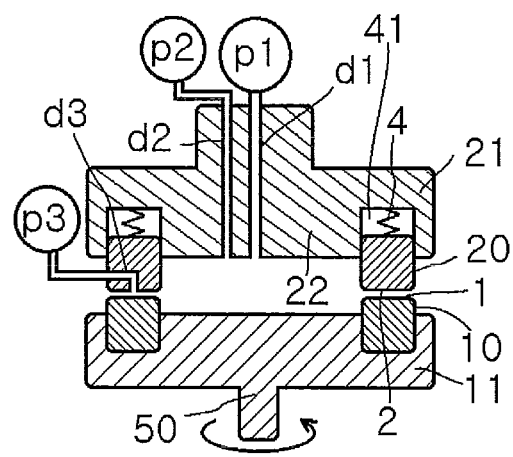
Figure 4:
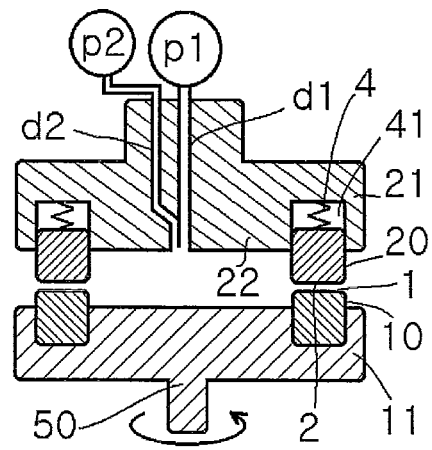
Figure 4:
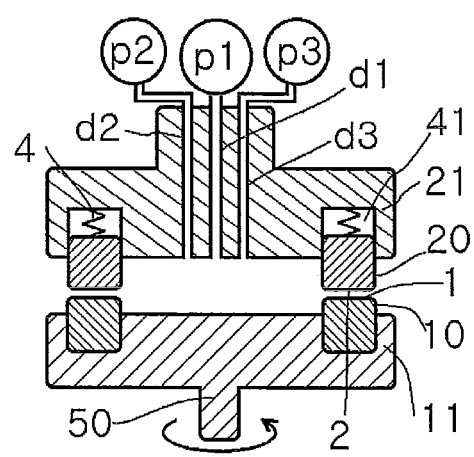
Figure 5:
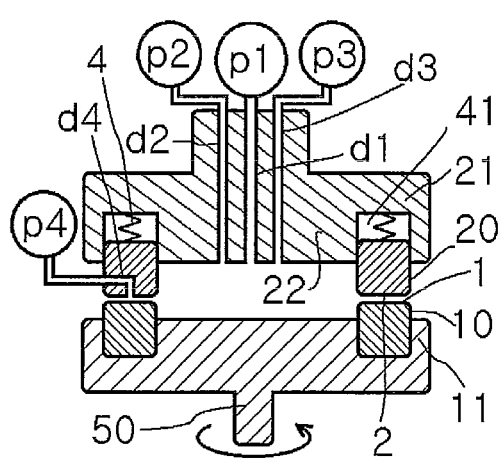
FIG. 5(A) to FIG. 5(D) each show a schematic vertical sectional view showing the concept of still another embodiment of the apparatus shown in FIG. 1.
Figure 5:
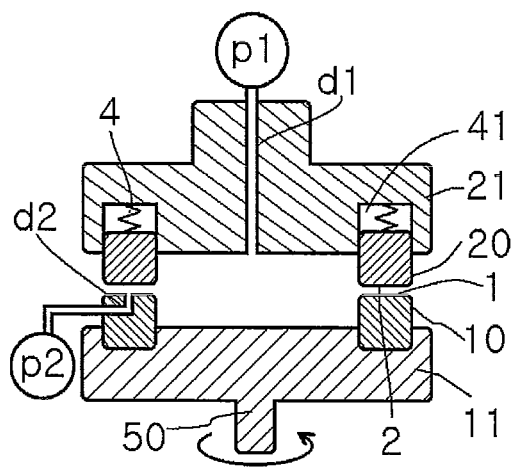
Figure 5:
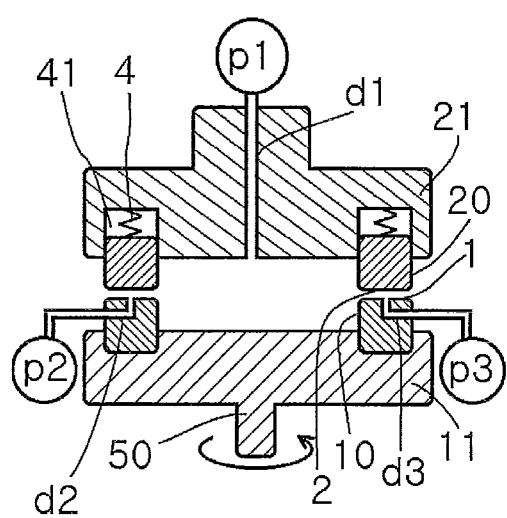
Figure 5:
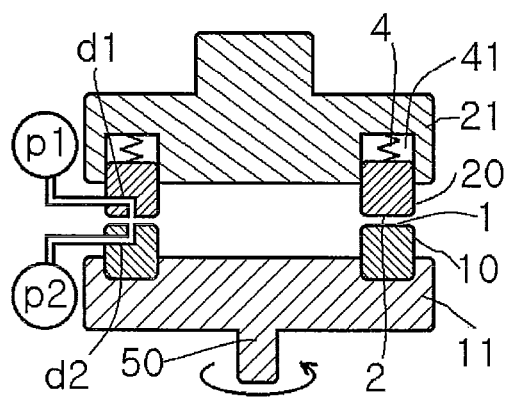
Figure 6:
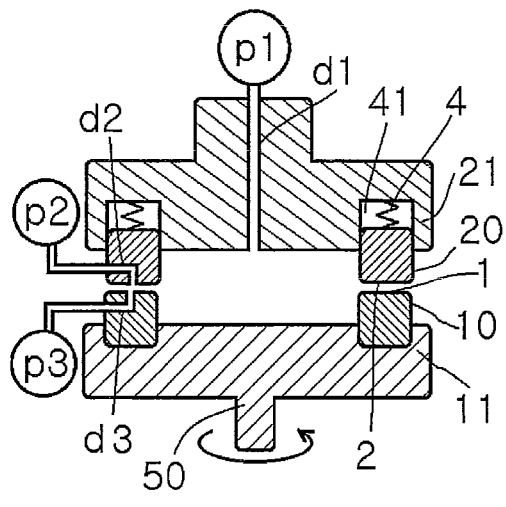
FIG. 6(A) to FIG. 6(D) each show a schematic vertical sectional view showing the concept of still another embodiment of the apparatus shown in FIG. 1.
Figure 6:
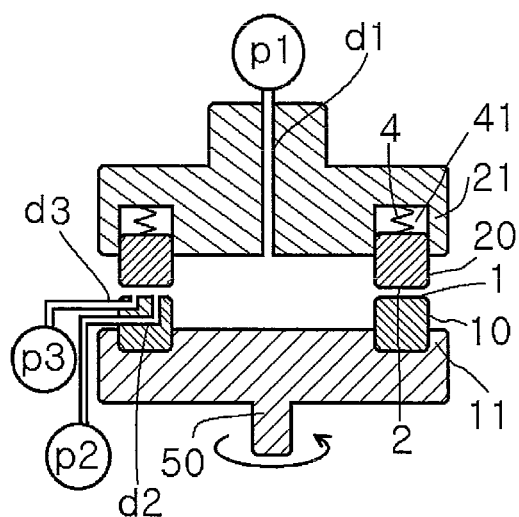
Figure 6:
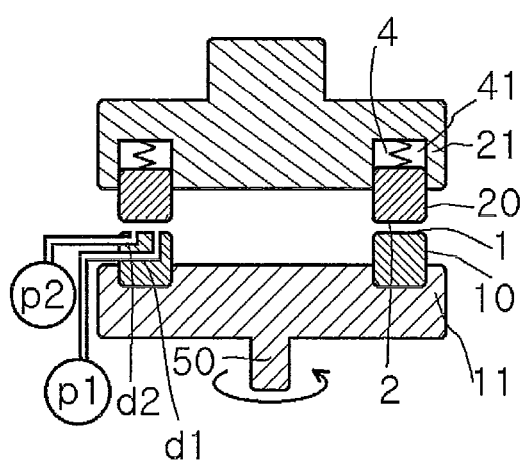
Figure 6:
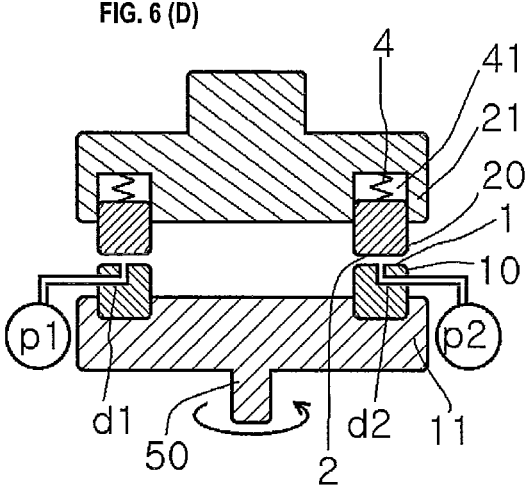
Figure 7:
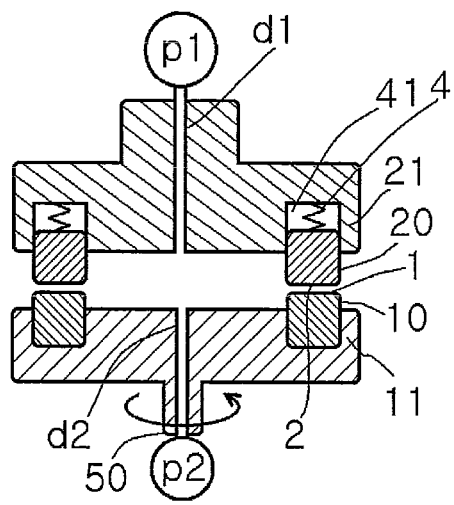
FIG. 7(A) to FIG. 7(D) each show a schematic vertical sectional view showing the concept of still another embodiment of the apparatus shown in FIG. 1.
Figure 7:
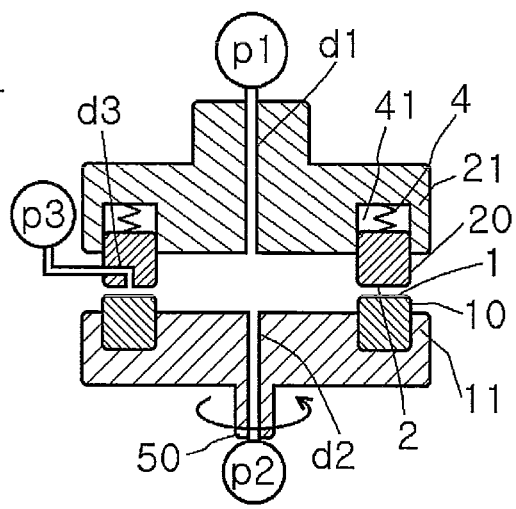
Figure 7:
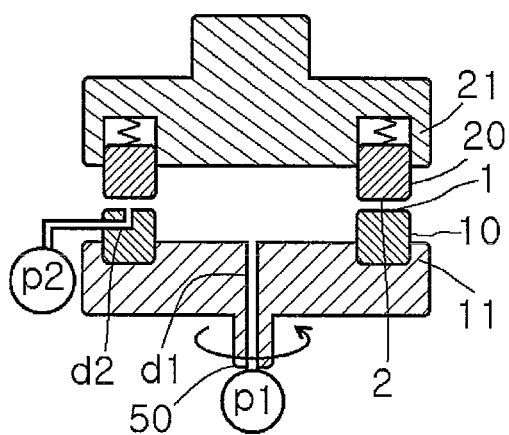
Figure 7:
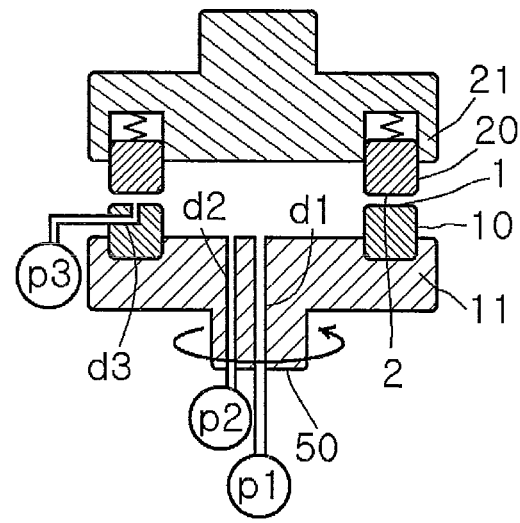
Figure 8:
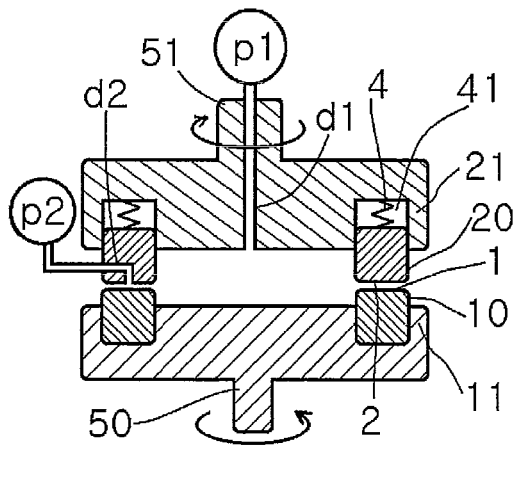
FIG. 8(A) to FIG. 8(D) each show a schematic vertical sectional view showing the concept of still another embodiment of the apparatus shown in FIG. 1.
Figure 8:
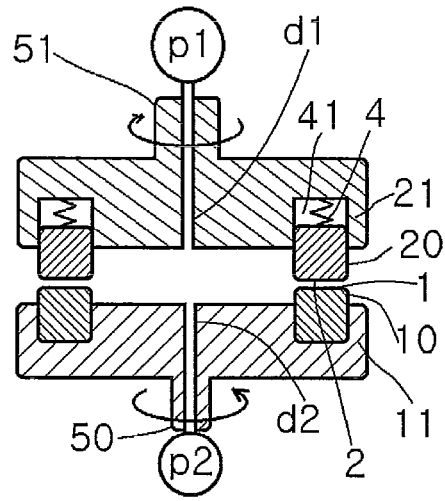
Figure 8:
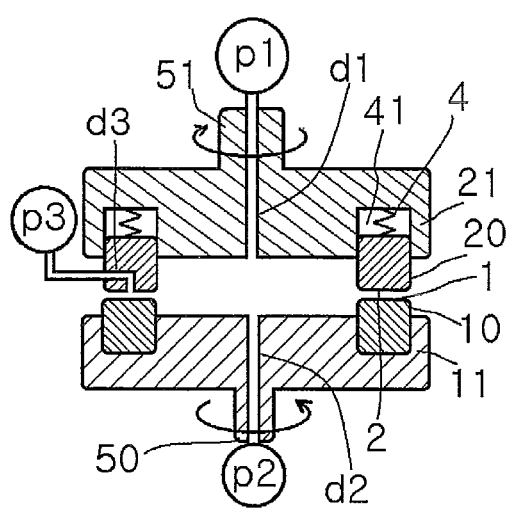
Figure 8:
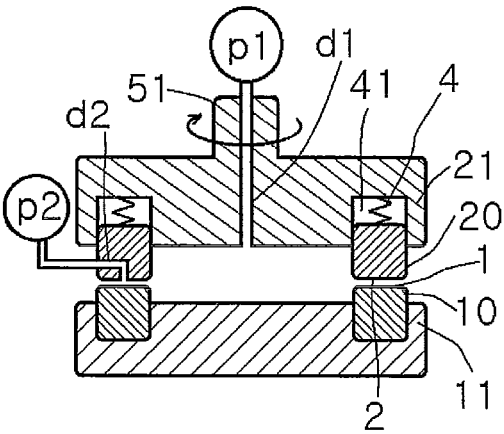
Figure 9:
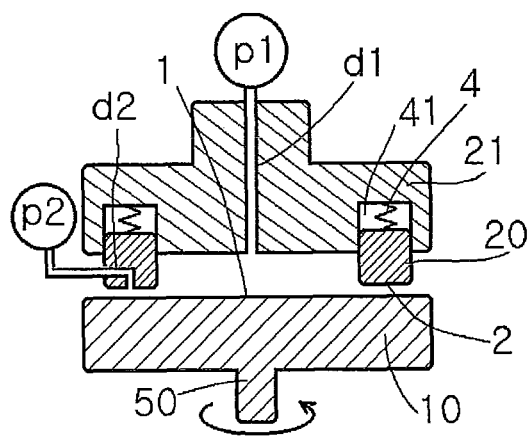
FIG. 9(A) to FIG. 9(C) each show a schematic vertical sectional view showing the concept of still another embodiment of the apparatus shown in FIG. 1.
Figure 9:
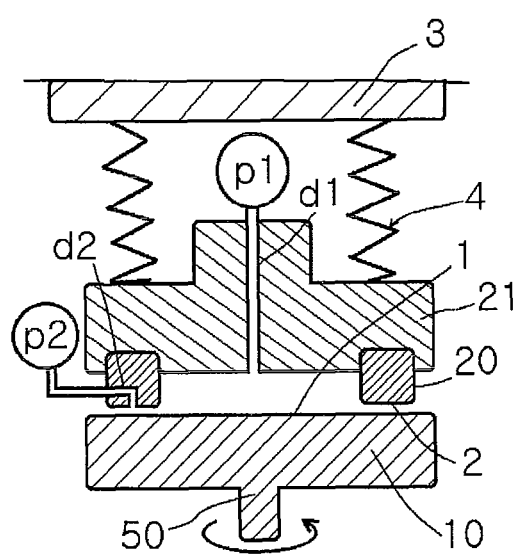
Figure 9:
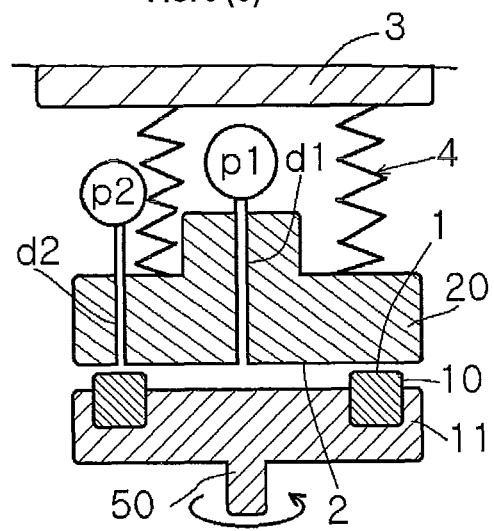
Figure 10:
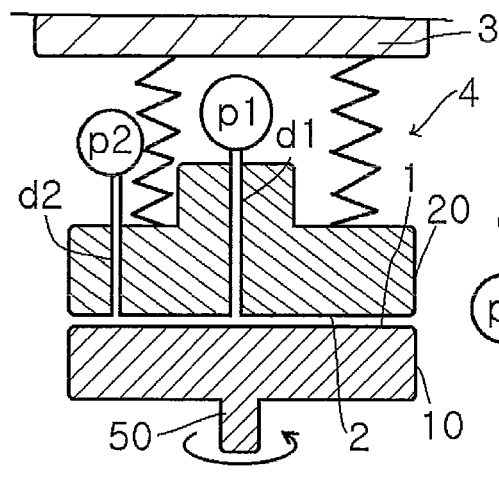
FIG. 10(A) to FIG. 10(D) each show a schematic vertical sectional view showing the concept of still another embodiment of the apparatus shown in FIG. 1.
Figure 10:
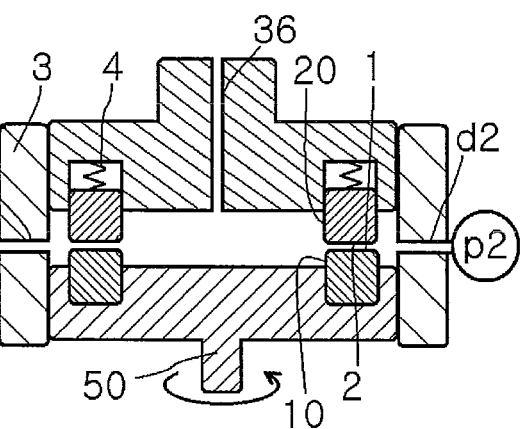
Figure 10:
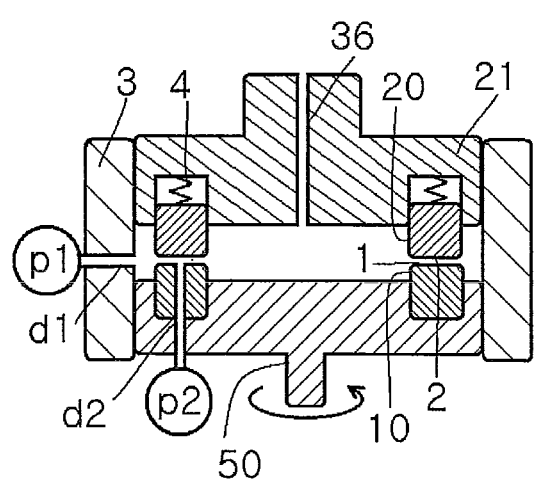
Figure 10:
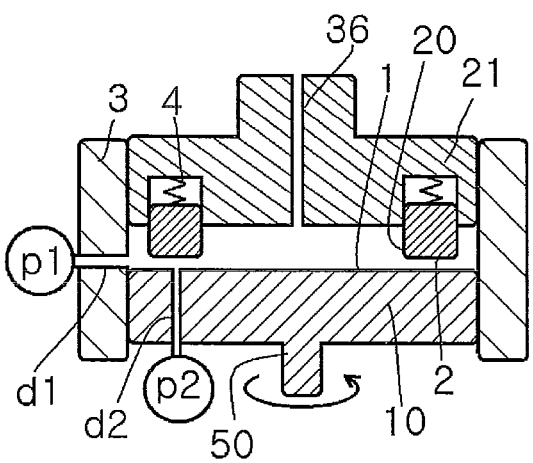

In the apparatuses shown in FIG. 4 and the apparatuses shown in FIG. 5(A), FIG. 7(A), FIG. 7(B), FIG. 7(D), FIG. 8(B) and FIG. 8(C), other fluids to be processed flow into the first fluid before reaching the processing surfaces 1 and 2, and these apparatuses are not suitable for the fluid which is rapidly crystallized or separated. However, these apparatuses can be used for the fluid having a low reaction speed.

The processing apparatus suitable for carrying out the method according to the present invention is summarized as follows.

As described above, the processing apparatus comprises a fluid pressure imparting mechanism that imparts predetermined pressure to a fluid to be processed, at least two processing members, that is, a first processing member 10 arranged in a sealed fluid flow path through which the fluid at the predetermined pressure flows and a second processing member 20 capable of approaching to and separating from the first processing member 10, at least two processing surfaces of a first processing surface 1 and a second processing surface 2 arranged in a position in which they are faced with each other in the processing members 10 and 20, and a rotation drive mechanism that relatively rotates the first processing member 10 and the second processing member 20, wherein at least two fluids to be processed are mixed and reacted between the processing surfaces 1 and 2. Of the first processing member 10 and the second processing member 20, at least the second processing member 20 has a pressure-receiving surface, at least a part of the pressure-receiving surface is comprised of the second processing surface 2, and the pressure-receiving surface receives pressure applied by the fluid pressure imparting mechanism to at least one of the fluids to generate a force to move in the direction of separating the second processing surface 2 from the first processing surface 1. In this apparatus, the fluid that has received said pressure passes through the space between the first processing surface 1 and the second processing surface 2 capable of approaching to and separating from each other, thereby generating a desired reaction between the processed fluids with the fluids being passed between the processing surfaces 1 and 2 and forming a thin film fluid of predetermined thickness.

In this processing apparatus, at least one of the first processing surface 1 and the second processing surface 2 is preferably provided with a buffer mechanism for regulation of micro-vibration and alignment.

In this processing apparatus, one of or both the first processing surface 1 and the second processing surface 2 is preferably provided with a displacement regulating mechanism capable of regulating the displacement in the axial direction caused by abrasion or the like thereby maintaining the thickness of a thin film fluid between the processing surfaces 1 and 2.

In this processing apparatus, a pressure device such as a compressor for applying predetermined feeding pressure to a fluid can be used as the fluid pressure imparting mechanism.

As the pressure device, a device capable of regulating an increase and decrease in feeding pressure is used. This is because the pressure device should be able to keep established pressure constant and should be able to regulate an increase and decrease in feeding pressure as a parameter to regulate the distance between the processing surfaces.

The processing apparatus can be provided with a separation preventing part for defining the maximum distance between the first processing surface 1 and the second processing surface 2 and preventing the processing surfaces 1 and 2 from separating from each other by the maximum distance or more.

The processing apparatus can be provided with an approach preventing part for defining the minimum distance between the first processing surface 1 and the second processing surface 2 and preventing the processing surfaces 1 and 2 from approaching to each other by the minimum distance or less.

The processing apparatus can be one wherein both the first processing surface 1 and the second processing surface 2 are rotated in opposite directions.

The processing apparatus can be provided with a temperature-regulating jacket for regulating the temperature of either or both of the first processing surface 1 and the second processing surface 2.

The processing apparatus is preferably one wherein at least a part of either or both of the first processing surface 1 and the second processing surface 2 is mirror-polished.

The processing apparatus can be one wherein one of or both the first processing surface 1 and the second processing surface 2 is provided with depressions.

The processing apparatus preferably includes, as a means for feeding one fluid to be reacted with another fluid, a separate introduction path independent of a path for another fluid, at least one of the first processing surface and the second processing surface is provided with an opening leading to the separate introduction path, and another fluid sent through the separate introduction path is introduced into the one fluid.

The processing apparatus for carrying out the present invention comprises a fluid pressure imparting mechanism that imparts predetermined pressure to a fluid to be processed, at least two processing surfaces of a first processing surface 1 and a second processing surface 2 capable of approaching to and separating from each other which are connected to a sealed fluid flow path through which the fluid at the predetermined pressure is passed, a surface-approaching pressure imparting mechanism that imparts surface-approaching pressure to the space between the processing surfaces 1 and 2, and a rotation drive mechanism that relatively rotates the first processing surface 1 and the second processing surface 2, wherein at least two fluids to be processed are reacted between the processing surfaces 1 and 2, at least one fluid pressurized with the fluid pressure imparting mechanism is passed through the space between the first processing surface 1 and the second processing surface 2 rotating to each other and supplied with surface-approaching pressure, and another fluid is passed, so that the fluid pressurized with the fluid pressure imparting mechanism, while being passed between the processing surfaces and forming a thin film fluid of predetermined thickness, is mixed with another processed fluid, whereby a desired reaction is caused between the fluids.

The surface-approaching pressure imparting mechanism can constitute a buffer mechanism of regulating micro-vibration and alignment and a displacement regulation mechanism in the apparatus described above.

The processing apparatus for carrying out the present invention comprises a first introduction part that introduces, into the apparatus, at least one of two fluids to be reacted, a fluid pressure imparting mechanism p that is connected to the first introduction part and imparts pressure to a fluid to be processed, a second introduction part that introduces at least the other fluid of the two fluids to be reacted, at least two processing members, that is, a first processing member 10 arranged in a sealed fluid flow path through which the other fluid is passed and a second processing member 20 capable of relatively approaching to and separating from the first processing member 10, at least two processing surfaces, that is, a first processing surface 1 and a second processing surface 2 arranged so as to be opposite to each other in the processing members 10 and 20, a holder 21 that accepts the second processing member 20 so as to expose the second processing surface 2, a rotation drive mechanism that relatively rotates the first processing member 10 and the second processing member 20, and a surface-approaching pressure imparting mechanism 4 that presses the second processing member 20 against the first processing surface 1 such that the second processing surface 2 is contacted against or made close to the first processing surface 1, wherein the fluids to be processed are reacted between the processing surfaces 1 and 2, the holder 21 is provided with an opening of the first introduction part and is not movable so as to influence the space between the processing surfaces 1 and 2, at least one of the first processing member 10 and the second introduction part 20 is provided with an opening of the second introduction part, the second processing member 20 is circular, the second processing surface 2 slides along the holder 21 and approaches to and separates from the first processing surface 1, the second processing member 20 includes a pressure-receiving surface, the pressure-receiving surface receives pressure applied by the fluid pressure imparting mechanism p1 to the fluid to generate a force to move in the direction of separating the second processing surface 2 from the first processing surface 1, at least a part of the pressure-receiving surface is comprised of the second processing surface 2, one of the fluids to which pressure was applied is passed through the space between the first processing surface 1 and the second processing surface 2 rotating to each other and capable of approaching to and separating from each other, and the other fluid is supplied to the space between the processing surfaces 1 and 2, whereby both the fluids form a thin film fluid of predetermined thickness and pass through the space between both the processing surfaces 1 and 2, the passing fluids are mixed thereby promoting a desired reaction between the processed fluids, and the minimum distance for generating the thin film fluid of predetermined thickness is kept between the processing surfaces 1 and 2 by the balance between the surface-approaching pressure by the surface-approaching pressure imparting mechanism 4 and the force of separating the processing surfaces 1 and 2 from each other by the fluid pressure imparted by the fluid pressure imparting mechanism p1.

In this processing apparatus, the second introduction part can be, similarly being connected to the first introduction part, arranged to be connected to a separate fluid pressure imparting mechanism and to be pressurized. The fluid introduced from the second introduction part is not pressurized by the separate fluid pressure imparting mechanism, but is sucked and supplied into the space between the processing surfaces 1 and 2 by negative pressure generated in the second introduction part by the fluid pressure of the fluid introduced into the first introduction part. Alternatively, the other fluid flows downward by its weight in the second introduction part and can be supplied into the space between the processing surfaces 1 and 2.

As described above, the apparatus is not limited to the one wherein the opening of the first introduction part as an inlet for feeding the other fluid to be processed into the apparatus is arranged in the second holder, and the opening of the first introduction part may be arranged in the first holder. The opening of the first introduction part may be formed with at least one of the processing surfaces. However, when the fluid to be previously introduced into the space between the processing surfaces 1 and 2 should, depending on the reaction, be supplied from the first introduction part, the opening of the second introduction part as an inlet for feeding the other fluid into the apparatus should be arranged downstream from the opening of the first introduction part in any of the processing surfaces.

As the processing apparatus for carrying out the present invention, the following apparatus can be used.

This processing apparatus comprises a plurality of introduction parts that separately introduce two or more fluids to be reacted, a fluid pressure imparting mechanism p that imparts pressure to at least one of the two or more fluids, at least two processing members, that is, a first processing member 10 arranged in a sealed fluid flow path through which the processed fluid is passed and a second processing member 20 capable of approaching to and separating from the first processing member 10, at least two processing surfaces 1 and 2, that is, a first processing surface 1 and a second processing surface 2 arranged in a position in which they are faced with each other in the processing members 10 and 20, and a rotation drive mechanism that relatively rotates the first processing member 10 and the second processing member 20, wherein the fluids are reacted between the processing surfaces 1 and 2, at least the second processing member 20 of the first processing member 10 and the second processing member 20 includes a pressure-receiving surface, at least a part of the pressure-receiving surface is comprised of the second processing surface 2, the pressure-receiving surface receives pressure applied by the fluid pressure imparting mechanism to the fluid to generate a force to move in the direction of separating the second processing surface 2 from the first processing surface 1, the second processing member 20 includes an approach regulating surface 24 that is directed to the opposite side of the second processing surface 2, the approach regulating surface 24 receives predetermined pressure applied to the fluid to generate a force to move in the direction of approaching the second processing surface 2 to the first processing surface 1, a force to move in the direction of separating the second processing surface 2 from the first processing surface 1 as a resultant force of total pressure received from the fluid is determined by the area ratio of the projected area of the approach regulating surface 24 in the approaching and separating direction to the projected area of the pressure-receiving surface in the approaching and separating direction, the fluid to which pressure was applied is passed through the space between the first processing surface 1 and the second processing surface 2 that rotate relative to each other and capable of approaching to and separating from each other, the other fluid to be reacted with the one fluid is mixed in the space between the processing surfaces, and the mixed fluid forms a thin film fluid of predetermined thickness and simultaneously passes through the space between the processing surfaces 1 and 2, thereby giving a desired reaction product while passing through the space between the processing surfaces.

The processing method according to the present invention is summarized as follows. The processing method comprises applying predetermined pressure to a first fluid, connecting at least two processing surfaces, that is, a first processing surface 1 and a second processing surface 2, which are capable of approaching to and separating from each other, to a sealed fluid flow path through which the fluid that has received the predetermined pressure is passed, applying a surface-approaching pressure of approaching the first processing surface 1 and the second processing surface 2 each other, rotating the first processing surface 1 and the second processing surface 2 relative to each other, and introducing the fluid into the space between the processing surfaces 1 and 2, wherein the second fluid to be reacted with the first fluid is introduced through a separate flow path into the space between the processing surfaces 1 and 2 thereby reacting both the fluids, the predetermined pressure applied to at least the first fluid functions as a separating force for separating the processing surfaces 1 and 2 from each other, and the separating force and the surface-approaching pressure are balanced via the fluid between the processing surfaces 1 and 2, whereby the distance between the processing surfaces 1 and 2 is kept in a predetermined minute space, the fluid is passed as a thin film fluid of predetermined thickness through the space between the processing surfaces 1 and 2, and when both the fluids are uniformly reacted with each other while passing and accompanied by separation, a desired reaction product is crystallized or separated.

Figure 25:
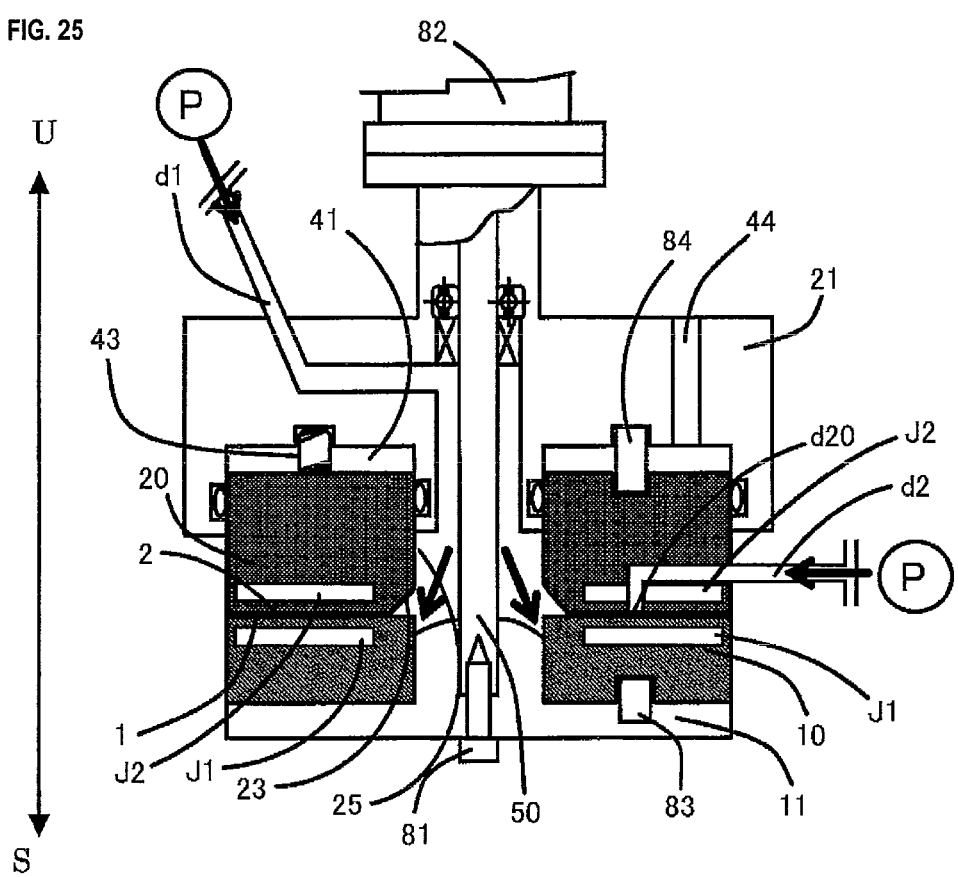
FIG. 25 is a schematic vertical sectional view showing outline of the apparatus of the present invention.
Figure 26:
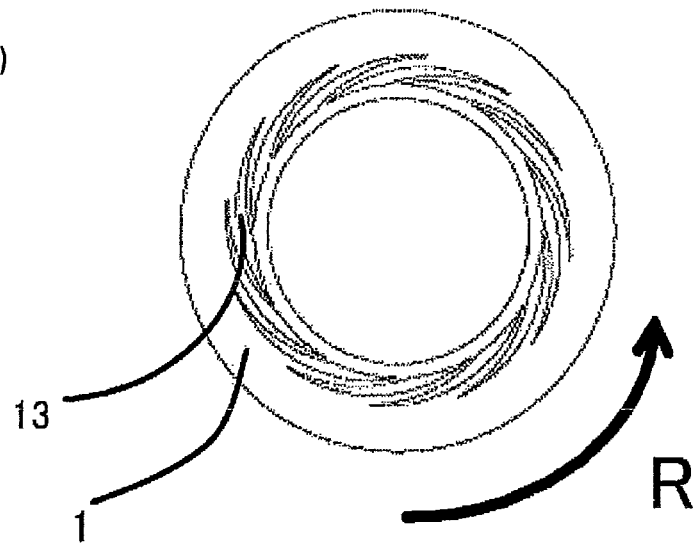
FIG. 26(A) is a schematic plane view of the first processing surface in the apparatus shown in FIG. 25.
FIG. 26(B) is an enlarged view showing an important part of the first processing surface in the apparatus shown in FIG. 25.
Figure 26:
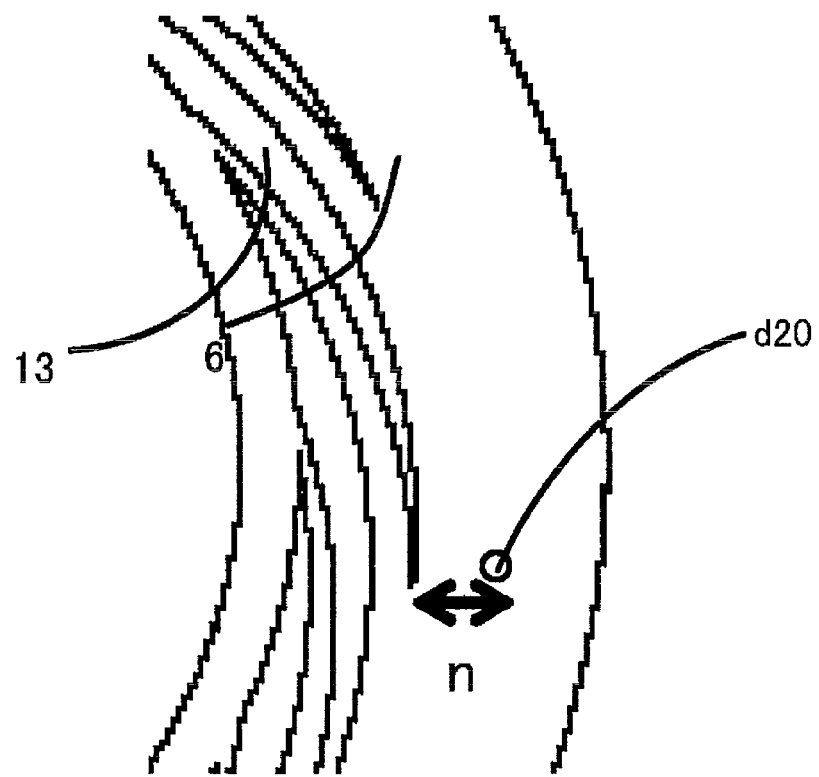
Figure 27:
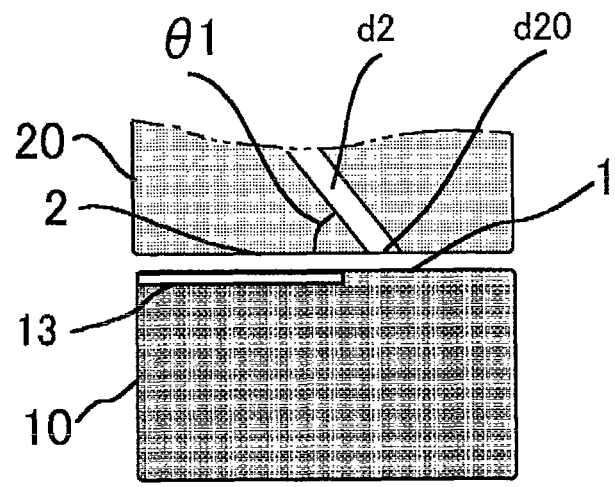
FIG. 27(A) is a sectional view of the second introduction part.
FIG. 27(B) is an enlarged view showing an important part of the processing surface for explaining the second introduction part.
Figure 27:
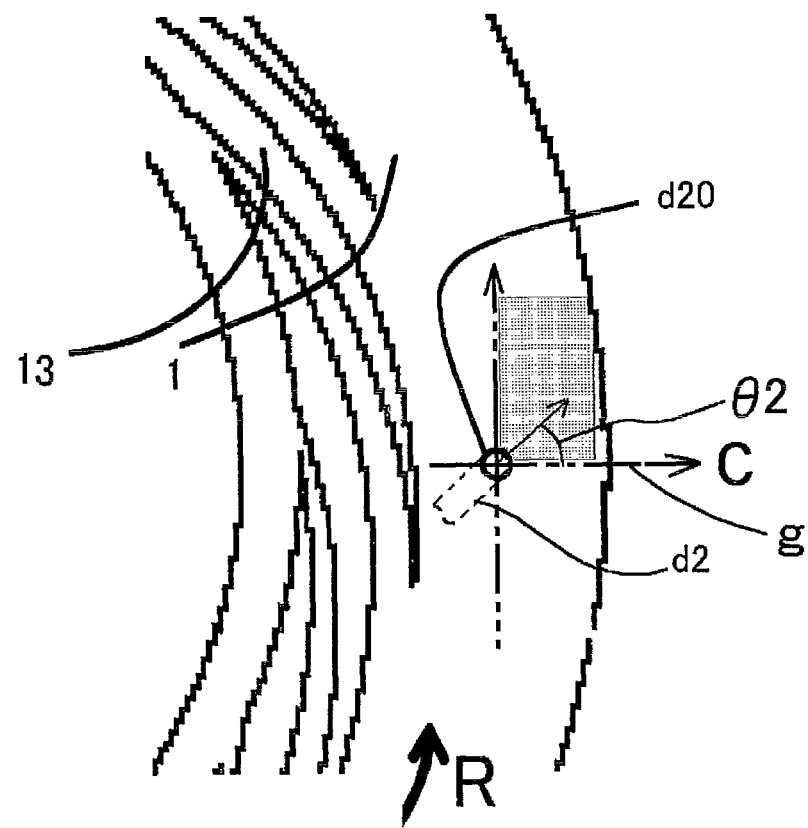

Hereinafter, other embodiments of the present invention are described in detail. FIG. 25 is a schematic sectional view of a reaction apparatus wherein reactants are reacted between processing surfaces, at least one of which rotates relative to the other, and which are capable of approaching to and separating from each other. FIG. 26(A) is a schematic plane view of the first processing surface in the apparatus shown in FIG. 25, and FIG. 26(B) is an enlarged view of an important part of the processing surface in the apparatus shown in FIG. 25. FIG. 27(A) is a sectional view of the second introduction part, and FIG. 27(B) is an enlarged view of an important part for explaining the second introduction part.

In FIG. 25, arrows U and S show upward and downward directions respectively.

In FIG. 26(A) and FIG. 27(B), arrow R shows the direction of rotation.

In FIG. 27(B), arrow C shows the direction of centrifugal force (radial direction).

This apparatus uses at least two fluids as a fluid to be processed that is described above, at least one of which contains at least one kind of reactant, and the fluids join together in the space between the processing surfaces arranged to be opposite so as to able to approach to and separate from each other, at least one of which rotates relative to the other, thereby forming a thin film fluid, and the reactants are reacted in the thin film fluid.

As shown in FIG. 25, this apparatus includes a first holder 11, a second holder 21 arranged over the first holder 11, a fluid pressure imparting mechanism P and a surface-approaching pressure imparting mechanism. The surface-approaching pressure imparting mechanism is comprised of a spring 43 and an air introduction part 44.

The first holder 11 is provided with a first processing member 10 and a rotary shaft 50. The first processing member 10 is a circular body called a mating ring and provided with a mirror-polished first processing surface 1. The rotary shaft 50 is fixed to the center of the first holder 11 with a fixing device 81 such as a bolt and is connected at its rear end to a rotation drive device 82 (rotation drive mechanism) such as a motor, and the drive power of the rotation drive device 82 is transmitted to the first holder 1 thereby rotating the first holder 11. The first processing member 10 is integrated with the first holder 11 and rotated.

A receiving part capable of receiving the first processing member 10 is arranged on the upper part of the first holder 11, wherein the first processing member 10 has been fixed to the first holder 11 by insertion to the receiving part. The first processing member 10 has been fixed with a rotation-preventing pin 83 so as not to be rotated relative to the first holder 11. However, a method such as fitting by burning may be used for fixing in place of the rotation-preventing pin 83 in order to prevent rotation.

The first processing surface 1 is exposed from the first holder 11 and faced with the second holder 21. The material for the first processing surface includes ceramics, sintered metal, abrasion-resistant steel, other hardened metals, and rigid materials subjected to lining, coating or plating.

The second holder 21 is provided with a second processing member 20, a first introduction part d1 for introducing a fluid from the inside of the processing member, a spring 43 as a surface-approaching pressure imparting mechanism, and an air introduction part 44.

The second processing member 20 is a circular member called a compression ring and includes a second processing surface 2 subjected to mirror polishing and a pressure-receiving surface 23 (referred to hereinafter as separation regulating surface 23) which is located inside the second processing surface 2 and adjacent to the second processing surface 2. As shown in the figure, the separation regulating surface 23 is an inclined surface. The method of the mirror polishing to which the second processing surface 2 was subjected is the same as that to the first processing surface 1. The material for the second processing member 20 may be the same as one for the first processing member 10. The separation regulating surface 23 is adjacent to the inner periphery 25 of the circular second processing member 20.

A ring-accepting part 41 is formed in the bottom (lower part) of the second holder 21, and the second processing member 20 together with an O-ring is accepted in the ring-accepting part 41. The second processing member 20 is accepted with a rotation preventive 84 so as not to be rotated relative to the second holder 21. The second processing surface 2 is exposed from the second holder 21. In this state, the second processing surface 2 is faced with the first processing surface 1 of the first processing member 10.

The ring-accepting part 41 arranged in the second holder 21 is a depression for mainly accepting that side of the second ring 20 which is opposite to the processing surface 2 and is a groove formed in a circular form when viewed in a plane.

The ring-accepting part 41 is formed in a larger size than the second ring 20 and accepts the second ring 20 with sufficient clearance between itself and the second ring 20.

By this clearance, the second processing member 20 is accepted in the ring-accepting part 41 such that it can be displaced not only in the axial direction of the accepting part 41 but also in a direction perpendicular to the axial direction. The second processing member 20 is accepted in the ring-accepting part 41 such that the central line (axial direction) of the second processing member 20 can be displaced so as not to be parallel to the axial direction of the ring-accepting part 41.

The spring 43 is arranged as a processing member-biasing part in at least the ring-accepting part 41 of the second holder 21. The spring 43 biases the second processing member 20 toward the first processing member 10. As another bias method, air pressure such as one in the air introduction part 44 or another pressurization means for applying fluid pressure may be used to bias the second processing member 20 held by the second holder 21 in the direction of approaching the second processing member 20 to the first processing member 10.

The surface-approaching pressure imparting mechanism such as the spring 43 or the air introduction part 44 biases each position (each position in the processing surface) in the circumferential direction of the second processing member 20 evenly toward the first processing member 10. The first introduction part d1 is arranged on the center of the second holder 21, and the fluid which is pressure-fed from the first introduction part d1 to the outer periphery of the processing member is first introduced into the space surrounded with the second processing member 20 held by the second holder 21, the first processing member 10, and the first holder 11 that holds the first processing member 10. Then, the feeding pressure (supply pressure) of the fluid by the fluid pressure imparting mechanism P is applied to the pressure-receiving surface 23 arranged in the second processing member 20, in the direction of separating the second processing member 20 from the first processing member 10 against the bias of the biasing part.

Figure 29:
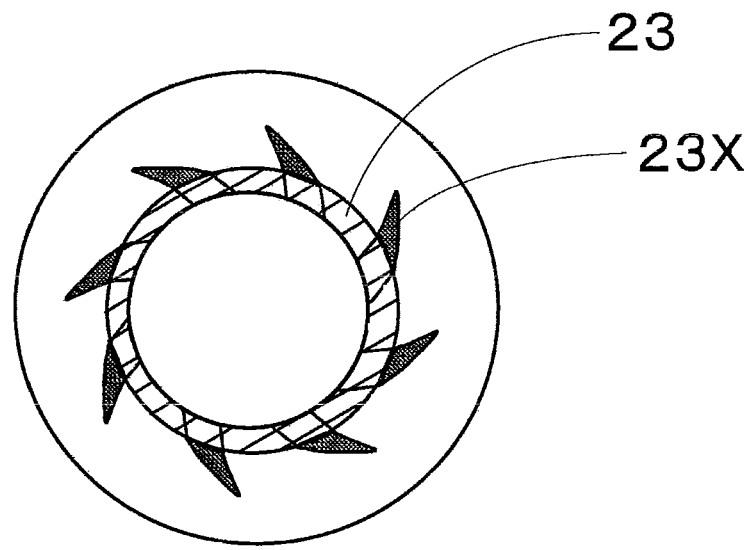
FIG. 29 is a diagram for explaining a pressure-receiving surface arranged in the processing member.
Figure 29:
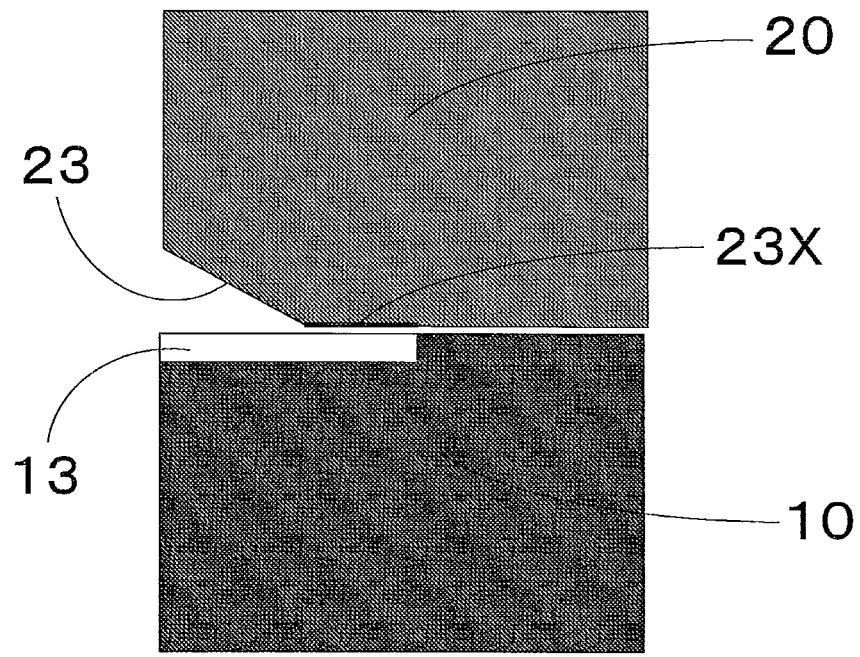

For simplifying the description of other components, only the pressure-receiving surface 23 is described, and as shown in FIG. 29(A) and FIG. 29(B), properly speaking, together with the pressure-receiving surface 23, a part 23X not provided with the pressure-receiving surface 23, out of the projected area in the axial direction relative to the second processing member 20 in a grooved depression 13 described later, serves as a pressure-receiving surface and receives the feeding pressure (supply pressure) of the fluid by the fluid pressure imparting mechanism P.

The apparatus may not be provided with the pressure-receiving surface 23. In this case, as shown in FIG. 26(A), the effect (micro-pump effect) of introduction of the fluid to be processed into the space between the processing surfaces formed by rotation of the first processing surface 1 provided with the grooved depression 13 formed to function the surface-approaching pressure imparting mechanism may be used. The micro-pump effect is an effect by which the fluid in the depression advances with speed toward the end in the circumferential direction by rotation of the first processing surface 1 and then the fluid sent to the end of the depression 13 further receives pressure in the direction of inner periphery of the depression 13 thereby finally receiving pressure in the direction of separating the processing surface and simultaneously introducing the fluid into the space between the processing surfaces. Even if the first processing surface 1 is not rotated, the pressure applied to the fluid in the depression 13 arranged in the first processing surface 1 finally acts on the second processing surface 2 to be separated as a pressure-receiving surface.

For the depression 13 arranged on the processing surface, its total area in the horizontal direction relative to the processing surface, and the depth, number, and shape of depressions, can be established depending on the physical properties of a fluid containing reactants and reaction products.

The pressure-receiving surface 23 and the depression 13 may be arranged in the same apparatus.

The depression 13 is a depression having a depth of 1 μm to 50 μm, preferably 3 μm to 20 μm, which is arranged on the processing surface, the total area thereof in the horizontal direction is 5% to 50%, preferably 15% to 25%, based on the whole of the processing surface, the number of depressions is 3 to 50, preferably 8 to 24, and the depression extends in a curved or spiral form on the processing surface or bends at a right angle. By having depth changing continuously, fluids with high to low viscosity, even containing solids, can be introduced into the space between the processing surfaces stably by the micro-pump effect. The depressions 13 arranged on the processing surface may be connected to one another or separated from one another in the side of introduction, that is, inside the processing surface.

As described above, the pressure-receiving surface 23 is inclined. This inclined surface (pressure-receiving surface 23) is formed such that the distance in the axial direction between the upstream end in the direction of flow of the fluid and the processing surface of the processing member provided with the depression 13 is longer than the distance between the downstream end and the aforesaid processing surface. The downstream end of this inclined surface in the direction of flow of the fluid is arranged preferably on the projected area in the axial direction of the depression 13.

Figure 28:
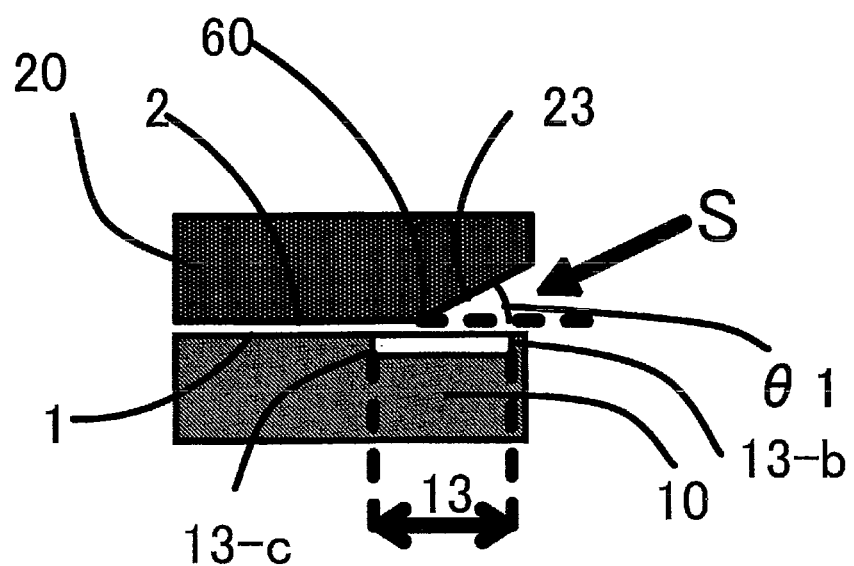
FIG. 28(A) and FIG. 28(B) are each an enlarged sectional view of an important part for explaining an inclined surface (pressure-receiving surface) arranged in the processing member.
Figure 28:
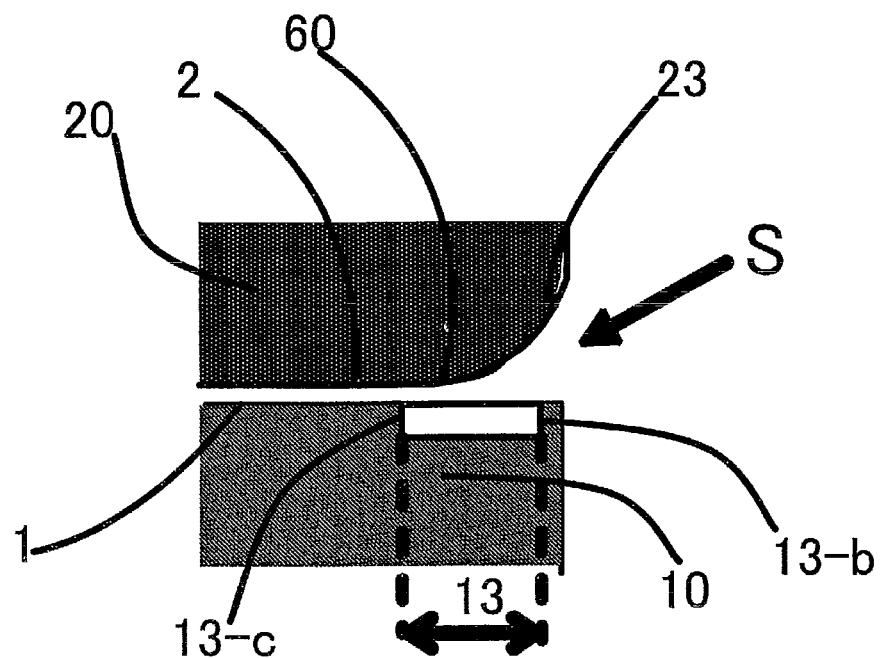

Specifically, as shown in FIG. 28(A), a downstream end 60 of the inclined surface (pressure-receiving surface 23) is arranged on the projected area in the axial direction of the depression 13. The angle θ1 of the inclined surface to the second processing surface 2 is preferably in the range of 0.1° to 85°, more preferably in the range of 10° to 55°, still more preferably in the range of 15° to 45°. The angle θ1 can vary depending on properties of the product before processing. The downstream end 60 of the inclined surface is arranged in the region extending from the position apart downstream by 0.01 mm from an upstream end 13-b to the position apart upstream by 0.5 mm from a downstream end 13-c in the depression 13 arranged in the first processing surface 1. The downstream end 60 of the inclined surface is arranged more preferably in the region extending from the position apart downstream by 0.05 mm from the upstream end 13-b to the position apart upstream by 1.0 mm from the downstream end 13-c. Like the angle of the inclined surface, the position of the downstream end 60 can vary depending on properties of a material to be processed. As shown in FIG. 28(B), the inclined surface (pressure-receiving surface 23) can be a curved surface. The material to be processed can thereby be introduced more uniformly.

The depressions 13 may be connected to one another or separated from one another as described above. When the depressions 13 are separated, the upstream end at the innermost peripheral side of the first processing surface 1 is 13-b, and the upstream end at the outermost peripheral side of the first processing surface 1 is 13-c.

In the foregoing description, the depression 13 was formed on the first processing surface 1 and the pressure-receiving surface 23 was formed on the second processing surface 2. On the contrary, the depression 13 may be formed on the second processing surface 2, and the pressure-receiving surface 23 may be formed on the first processing surface 1.

Alternatively, the depression 13 is formed both on the first processing surface 1 and the second processing surface 2, and the depression 13 and the pressure-receiving surface 23 are alternately arranged in the circumferential direction of each of the respective processing surfaces 1 and 2, whereby the depression 13 formed on the first processing surface 1 and the pressure-receiving surface 23 formed on the second processing surface 2 are faced with each other and simultaneously the pressure-receiving surface 23 formed on the first processing surface 1 and the depression 13 formed on the second processing surface 2 are faced with each other.

A groove different from the depression 13 can be formed on the processing surface. Specifically, as shown in FIG. 16(F) and FIG. 16(G), a radially extending novel depression 14 instead of the depression 13 can be formed outward in the radial direction (FIG. 16(F)) or inward in the radial direction (FIG. 16(G)). This is advantageous for prolongation of retention time between the processing surfaces or for processing a highly viscous fluid.

The groove different from the depression 13 is not particularly limited with respect to the shape, area, number of depressions, and depth. The groove can be formed depending on the object.

The second introduction part d2 independent of the fluid flow path introduced into the processing surface and provided with the opening d20 leading to the space between the processing surfaces is formed on the second processing member 20.

Specifically, as shown in FIG. 27(A), the direction of introduction of the second introduction part d2 from the opening d20 of the second processing surface 2 is inclined at a predetermined elevation angle (θ1) relative to the second processing surface 2. The elevation angle (θ1) is arranged at more than 0° and less than 90°, and when the reaction speed is high, the angle (θ1) is preferably arranged at 1° to 45°.

As shown in FIG. 27(B), the direction of introduction of the second processing surface 2 from the opening d20 has directionality in a plane along the second processing surface 2. The direction of introduction of the second fluid is in the direction in which a component on the processing surface is made apart in the radial direction and in the direction in which the component is forwarded in the rotation direction of the fluid between the rotating processing surfaces. In other words, a predetermined angle (θ2) exists facing the rotation direction R from a reference line g in the outward direction and in the radial direction passing through the opening d20.

The elevation angle (θ1) is arranged at more than 0° and less than 90°, and when the reaction speed is high, the angle (θ1) is preferably arranged at 1° to 45°.

The angle (θ2) is also arranged at more than 0° and less than 90° at which the fluid is discharged from the opening d20 in the shaded region in FIG. 27(B). When the reaction speed is high, the angle (θ2) may be small, and when the reaction speed is low, the angle (θ2) is preferably arranged larger. This angle can vary depending on various conditions such as the type of fluid, the reaction speed, viscosity, and the rotation speed of the processing surface.

The bore diameter of the opening d20 is preferably 0.2 μm to 3000 μm, more preferably 10 μm to 1000 μm. Even if the bore diameter of the opening d20 is relatively large, the diameter of the second introduction part d2 shall be 0.2 μm to 3000 μm, more preferably 10 μm to 1000 μm, and when the diameter of the opening d20 does not substantially influence the flow of a fluid, the diameter of the second introduction part d2 may be established in this range. Depending on whether the fluid is intended to be transferred straight or dispersed, the shape of the opening d20 is preferably changed and can be changed depending on various conditions such as the type of fluid, reaction speed, viscosity, and rotation speed of the processing surface.

The opening d20 in the separate flow path may be arranged at a position nearer to the outer diameter than a position where the direction of flow upon introduction by the micro-pump effect from the depression arranged in the first processing surface 1 is converted into the direction of flow of a spiral laminar flow formed between the processing surfaces. That is, in FIG. 26(B), the distance n from the outermost side in the radial direction of the processing surface of the depression arranged in the first processing surface 1 to the outside in the radial direction is preferably 0.5 mm or more. When a plurality of openings are arranged for the same fluid, the openings are arranged preferably concentrically. When a plurality of openings are arranged for different fluids, the openings are arranged preferably concentrically in positions different in radius. This is effective for the reactions such as cases (1) A+B→C and (2) C+D→E should occur in due order, but other case, i.e., A+B+C→F should not occur, or for circumventing a problem that an intended reaction does not occur due to insufficient contact among reactants.

The processing members are dipped in a fluid, and a fluid obtained by reaction between the processing surfaces can be directly introduced into a liquid outside the processing members or into a gas other than air.

Further, ultrasonic energy can be applied to the material just after being discharged from the space between the processing surfaces or from the processing surface.

Then, the case where temperature regulating mechanisms J1 and J2 are arranged in at least one of the first processing member 10 and the second processing member 20 for generating a temperature difference between the first processing surface 1 and the second processing surface 2 is described.

The temperature regulating mechanism is not particularly limited. A cooling part is arranged in the processing members 10 and 20 when cooling is intended. Specifically, a piping for passing ice water and various cooling media or a cooling element such as a Peltier device capable of electric or chemical cooling is attached to the processing members 10 and 20.

When heating is intended, a heating part is arranged in the processing members 10 and 20. Specifically, steam as a temperature regulating medium, a piping for passing various hot media, and a heating element such as an electric heater capable of electric or chemical heating is attached to the processing members 10 and 20.

An accepting part for a new temperature regulating medium capable of directly contacting with the processing members may be arranged in the ring-accepting part. The temperature of the processing surfaces can be regulated by heat conduction of the processing members. Alternatively, a cooling or heating element may be embedded in the processing members 10 and 20 and electrified, or a path for passing a cooling medium may be embedded, and a temperature regulating medium (cooling medium) is passed through the path, whereby the temperature of the processing surfaces can be regulated from the inside. By way of example, the temperature regulating mechanisms J1 and J2 which are pipes (jackets) arranged inside the processing members 10 and 20 are shown in FIG. 25.

By utilizing the temperature regulating mechanisms J1 and J2, the temperature of one of the processing surfaces is made higher than that of the other, to generate a temperature difference between the processing surfaces. For example, the first processing member 10 is heated to 60° C. by any of the methods, and the second processing member 20 is set at 15° C. by any of the methods. In this case, the temperature of the fluid introduced between the processing surfaces is changed from 60° C. to 15° C. in the direction from the first processing surface 1 to the second processing surface 2. That is, the fluid between the processing surfaces has a temperature gradient. The fluid between the processing surfaces initiates convection due to the temperature gradient, and a flow in a direction perpendicular to the processing surface is generated. The "flow in a direction perpendicular to the processing surface" refers to a flow in which components flowing in a direction perpendicular to at least the processing surface are contained in flowing components.

Even when the first processing surface 1 or the second processing surface 2 rotates, the flow in a direction perpendicular to the processing surface is continued, and thus the flow in a direction perpendicular to the processing surface can be added to a spiral laminar flow between the processing surfaces caused by rotation of the processing surfaces. The temperature difference between the processing surfaces is 1° C. to 400° C., preferably 5° C. to 100° C.

The rotary shaft 50 in this apparatus is not limited to a vertically arranged shaft. For example, the rotary shaft may be arranged at a slant. This is because the influence of gravity can be substantially eliminated by a thin film fluid formed between the processing surfaces 1 and 2 during processing. As shown in FIG. 25, the first introduction part d1 coincides with the shaft center of the second ring 20 in the second holder 21 and extends vertically. However, the first introduction part d1 is not limited to the one coinciding with the shaft center of the second ring 20, and as far as it can supply the first fluid to the space surrounded with the rings 10 and 20, the part d1 may be arranged at a position outside the shaft center in the central part 22 of the second holder 21 and may extend obliquely as well as vertically. Regardless of the angle at which the part d1 is arranged, a flow perpendicular to the processing surface can be generated by the temperature gradient between the processing surfaces.

When the temperature gradient of the fluid between the processing surfaces is low, heat conduction merely occurs in the fluid, but when the temperature gradient exceeds a certain border value, a phenomenon called Benard convection is generated in the fluid. This phenomenon is governed by Rayleigh number Ra, a dimensionless number, defined by the following equation:

$$Ra = L^3 \cdot g \cdot \beta \cdot \Delta T / (\alpha \cdot v)$$

wherein L is the distance between processing surfaces; g is gravitational acceleration; $\beta$ is coefficient of volumetric thermal expansion of fluid; $v$ is dynamic viscosity of fluid; $\alpha$ is heat diffusivity of fluid; and $\Delta T$ is temperature difference between processing surfaces. The critical Rayleigh number at which Benard convection is initiated to occur, although varying depending on the properties of a boundary phase between the processing surface and the fluid, is regarded as about 1700. At a value higher than this value, Benard convection occurs. Under the condition where the Rayleigh number Ra is a large value of about $10^{10}$ or more, the fluid becomes a turbulent flow. That is, the temperature difference $\Delta T$ between the processing surfaces or the distance L between the processing surfaces in this apparatus are regulated such that the Rayleigh number Ra becomes 1700 or more, whereby a flow perpendicular to the processing surface can be generated between the processing surfaces, and the reaction procedures described above can be carried out.

However, the Benard convection hardly occurs when the distance between the processing surfaces is about 1 μm to 10 μm. Strictly, when the Rayleigh number is applied to a fluid between the processing surfaces having a distance of 10 μm or less therebetween to examine the conditions under which Benard convection is generated, the temperature difference should be several thousands of degrees or more in the case of water, which is practically difficult. Benard convection is one related to density difference in temperature gradient of a fluid, that is, to gravity. When the distance between the processing surfaces is 10 μm or less, there is high possibility of minute gravity field, and in such a place, buoyancy convection is suppressed. That is, it is the case where the distance between the processing surfaces is 10 μm or more that Benard convection actually occurs.

When the distance between the processing surfaces is about 1 μm to 10 μm, convection is generated not due to density difference but due to surface tension difference of a fluid resulting from temperature gradient. Such convection is Marangoni convection. This phenomenon is governed by Marangoni number Ma, a dimensionless number, defined by the following equation:

$$Ma = \sigma \cdot \Delta T \cdot L / (\rho \cdot v \cdot \alpha)$$

wherein L is the distance between processing surfaces; $v$ is dynamic viscosity of fluid; $\alpha$ is heat diffusivity of fluid; $\Delta T$ is temperature difference between processing surfaces; $\rho$ is density of fluid; and $\sigma$ is temperature coefficient of surface tension (temperature gradient of surface tension). The critical Marangoni number at which Marangoni convection is initiated to occur is about 80, and under the conditions where the Marangoni number is higher than this value, Marangoni convection occurs. That is, the temperature difference $\Delta T$ between the processing surfaces or the distance L between the processing surfaces in this apparatus is regulated such that the Marangoni number Ma becomes 80 or more, whereby a flow perpendicular to the processing surface can be generated between the processing surfaces even if the distance therebetween is as small as 10 µm or less, and the reaction procedures described above can be carried out.

For calculation of Rayleigh number, the following equations were used.

$$Ra = \frac{L^3 \cdot \beta \cdot g}{v \cdot \alpha} \Delta T \quad \text{[Equation 1]}$$

$$\Delta T = (T_1 - T_0)$$

$$\alpha = \frac{k}{\rho \cdot C_p}$$

L is the distance (m) between processing surfaces; β is coefficient of volumetric thermal expansion (1/K); g is gravitational acceleration (m/s$^2$); ν is dynamic viscosity (m$^2$/s); α is heat diffusivity (m$^2$/s); ΔT is temperature difference (K) between processing surfaces; ρ is density (kg/m$^3$); Cp is isobaric specific heat (J/kg·K); k is heat conductivity (W/m·K); $T_1$ is temperature (K) at high temperature side in processing surface; and $T_0$ is temperature (K) at low temperature side in processing surface.

When the Rayleigh number at which Benard convection is initiated to occur is the critical Rayleigh number $Ra_c$, the temperature difference $\Delta T_{c1}$ is determined as follows:

$$\Delta T_{C1} = \frac{Ra_C \cdot v \cdot \alpha}{L^3 \cdot \beta \cdot g} \quad \text{[Equation 2]}$$

For calculation of Marangoni number, the following equations were used.

$$Ma = \frac{\sigma_t \cdot L}{\rho \cdot v \cdot \alpha} \Delta T \quad \text{[Equation 3]}$$

$$\Delta T = (T_1 - T_0)$$

$$\alpha = \frac{k}{\rho \cdot C_p}$$

L is the distance (m) between processing surfaces; ν is dynamic viscosity (m$^2$/s); α is heat diffusivity (m$^2$/s); ΔT is temperature difference (K) between processing surfaces; ρ is density (kg/m$^3$); Cp is isobaric specific heat (J/kg·K); k is heat conductivity (W/m·K); $\sigma_t$ is surface tension temperature coefficient (N/m·k); $T_1$ is temperature (K) of a high-temperature surface out of processing surface; and $T_0$ is temperature (K) of a low-temperature surface out of processing surface.

When the Marangoni number at which Marangoni convection is initiated to occur is the critical Marangoni number $Ma_c$, the temperature difference $\Delta T_{c2}$ is determined as follows:

$$\Delta T_{C2} = \frac{Ma_C \cdot \rho \cdot v \cdot \alpha}{\sigma_t \cdot L} \quad \text{[Equation 4]}$$

The materials for the processing surface arranged to be opposite to each other so as to be able to approach to and separate from each other, at least one of which rotates relative to the other, are not particularly limited, and the processing surfaces 1 and 2 can be prepared from ceramics, sintered metals, abrasion-resistant steels, other metals subjected to hardening treatment, or rigid materials subjected to lining, coating or plating. In the present invention, the distance between the processing surfaces 1 and 2 arranged to be opposite to each other so as to be able to approach to and separate from each other, at least one of which rotates relative to the other, is 0.1 µm to 100 µm, particularly preferably 1 µm to 10 µm.

In addition, the space between the processing surfaces may be heated (warmed), or may be radiated with ultraviolet ray (UV). Particularly, when a difference in temperature is set between the first processing surface 1 and the second processing surface 2, there is an advantage that since convection can be generated in a thin film fluid, the reaction can be promoted.

In order that separation of crystals does not occur due to a drop in liquid temperature before fluids are mixed, the temperature of the liquid sending tube extending from a pot for dissolution of the compound to a liquid spouting outlet in a mixing apparatus is preferably regulated so that the solution of the compound is always kept high at a temperature enough not to become supersaturated.

The producing method is conducted in a container capable of securing a depressurized or vacuum state, so as to form a depressurized or vacuum state of a secondary side at which the fluid after processing is discharged thereby removing a gas generated during the separation, removing a gas discharged from the processing member, or removing the solvent of the fluid. By doing so, a fluid containing the biologically ingestible microparticles separated between the processing surfaces is discharged in an atomized state from the processing surfaces, even when the producing method and removal of the solvent are almost simultaneously conducted, so that the surface area of the fluid is increased, and there is extremely high advantage to the efficiency of removal of the solvent.

Hereinafter, specific aspects of the method for producing biologically ingestible microparticles, which are carried out using the apparatus described above, will be described. First, a method of separating biologically ingestible microparticles by change in solubility is described.

In the thin film fluid formed between the processing surfaces in the apparatus described above, a solution containing a first solvent in which at least one kind of biologically ingestible microparticle material to be formed into microparticles has been dissolved is mixed with a solvent capable of serving as a second solvent in which the solubility of the biologically ingestible microparticle material is lower than in the first solvent, to separate biologically ingestible microparticles.

The biological ingestion material includes drugs. The present invention can be carried out using various drugs. The drug is preferably an organic substance occurring in a substantially pure state. The drug should be dispersible with low solubility in at least one kind of solvent and soluble in at least one kind of solvent. The low solubility means that the drug has a solubility of less than about 10 mg/mL, preferably less than about 1 mg/mL, in a solvent (for example, water) at a processing temperature (for example, room temperature). Solubility means that the drug is soluble in an amount of not less than 10 mg/mL. If necessary, the solvent may be heated or cooled. Preferably a dispersant (surfactant), a water-soluble polymer, a stabilizer, a preservative, a pH regulating agent, and a tonicity agent are previously added to one of or both of the first and second solvent.

Suitable drugs can be selected from various known drugs including, for example, analgesic agents, anti-inflammatory agents, anthelmintic agents, antiarrhythmic agents, antibiotics (including penicillin), anticoagulants, antihypotensive drugs, antidiabetic agents, antiepileptic drugs, antihistaminic agents, anti-malignant tumor agents, anti-obesity drugs, anorectic drugs, antihypertensive agents, antimuscarinic drugs, antimycobacterial agents, antineoplastic agents, immunosuppressive agents, antithyroid agents, antibacterial agents, antiviral agents, anti-anxiety drugs (hypnotics and neuroleptics), astringents, beta-adrenoreceptor blockers, blood preparations and plasma substitutes, myocardial inotropic agents, contrast media, corticosteroids, cough suppressants (expectorants and mucus-destructive agents), diagnostic agents, diagnostic image-forming agents, diuretic agents, dopaminergic agents (antiparkinson agents), hemostatic drugs, immunological agents, lipid regulatory agents, muscle relaxants, parasympathomimetic agents, parathyroid calcitonin and biphosphonates, prostaglandins, radioactive agents, sex hormones (including steroids), antiallergic agents, stimulants and anorexigenic agents, sympathomimetics, thyroid agents, vasodilators and xanthines, cataract remedies, and adrenal corticosteroids. The drugs are preferably those with low water solubility intended for oral administration or injections. Drugs of these classes and lists contained in each class can be found in "Martindale, The Extra Pharmacopoeia, $29^{th}$ edition, The Pharmaceutical Press, London, 1989". These drugs are commercially available or can be produced by methods known in the art.

Specific examples of drugs useful in the present invention include 17-α-pregno-2,4-diene-20-ino-[2,3-d]-isoxazol-17-ol (danazol), tacrolimus hydrate, progesterone, tranilast, benzbromarone, mefenamic acid, [6-methoxy-4-(1-methylethyl)-3-oxo-1,2-benzisothiazole-2(3H)-yl]methyl 2,6-dichlorobenzoate 1,1-dioxide (WIN 63, 394), 3-amino-1,2,4-benzotriazine-1,4-dioxide (WIN 59, 075), piposulfam, piposulfan, camptothecin, acetminophen, acetylsalicylic acid, amiodarone, cholestyramine, colestipol, cromolyn sodium, albuterol, sucralfate, sulfasalazine, minoxidil, tempazepam, alprazolam, propoxyphene, auranofin, erythromycin, cyclosporine, aciclovir, ganciclovir, etoposide, mephalan, methotrexate, minoxantrone, daunorubicin, doxorubicin, megestrol, tamoxifen, medroxyprogesterone, nystatin, terbutaline, amphotericin B, aspirin, ibuprofen, naproxen, indomethacin, diclofenac, ketoprofen, flurbiprofen, diflunisal, ethyl-3,5-diacetamide-2,4,6-triiodobenzoate (WIN 8883), ethyl (3,5-bis(acetylamino)-2,4,6-triiodobenzoyloxy)acetate (WIN 12, 901) and ethyl-2-(3,5-bis(acetylamino)-2,4,6-triiodobenzoyloxy)aceta to (WIN 16, 318).

In a preferable embodiment of the present invention, the drug is an immunosuppressive agent such as danazol or tacrolimus hydrate, an antiallergic drug such as tranilast, a steroid such as progesterone, an antiviral agent, an anti-malignant tumor agent or an anti-inflammatory agent.

Particularly preferable examples of the stabilizer and dispersant (surfactant) include sodium dodecylbenzene sulfonate, dodecyl sodium sulfate, tetradecyl sodium sulfate, pentadecyl sodium sulfate, octyl sodium sulfate, sodium oleate, sodium laurate, sodium stearate, calcium stearate, Tween 20 and Tween 80 (which are polyoxyethylene sorbitan fatty acid esters available from ICI Specialty Chemicals), polyvinyl pyrrolidone, tyloxapol, Pluronic F68 and F108 (which are ethylene oxide/propylene oxide block copolymers available from BASF), Tetronic 908 (T908) (which is a tetrafunctional block copolymer derived from an adduct of ethylenediamine to which ethylene oxide and propylene oxide are continuously added, available from BASF), dextran, lecithin, Aerosol OT (which is a dioctyl ester of sodium sulfosuccinate, available from American Cyanamid), Duponol P (which is sodium lauryl sulfate available from DuPont), Triton X-200 (which is an alkylaryl polyether sulfonate available from Rohm and Haas), Carbowax 3350 and 934 (which are polyethylene glycols available from Union Carbide), Crodesta F-110 (which is a mixture of sucrose stearate and sucrose distearate, available from Croda Inc.), Crodesta 5L-40 (which is available from Croda Inc.), and SA90HCO (which is $C_{18}H_{37}CH_2$—$(CON(CH_3)CH_2(CHOCH)_4CH_2OH)_2$), as well as quaternary amine surfactants such as benzethonium chloride and benzalkonium chloride and nonionic surfactants such as polyoxyethylene higher alcohol ethers, glycerin fatty acid esters, polyoxyethylene hardened castor oil, polyoxyethylene fatty acid esters, polyoxyethylene nonyl phenyl ether, polyoxyethylene octyl phenyl ether, sorbitan fatty acid ester, propylene glycol fatty acid ester, fatty acid polyethylene glycol, polyglycerin fatty acid ester, and sucrose fatty acid ester. These may be used depending on the objective biologically ingestible microparticles and the separating reaction.

The water-soluble polymer includes, for example, methyl cellulose, ethyl cellulose, propylmethyl cellulose, propyl cellulose, carboxymethyl cellulose, polyvinyl alcohol, and polyvinyl pyrrolidone.

The content of the drug in the present invention is not particularly limited. A highly concentrated suspension can be prepared and diluted to an intended concentration to prepare a pharmaceutical.

The stabilizer includes, for example, sodium edetate, sodium sulfite, sodium hydrogen sulfite, sodium thiosulfate, dibutyl hydroxy toluene, and tocopherol.

The preservative includes, for example, paraoxybenzoic acid ester, chlorobutanol, phenylethyl alcohol, benzalkonium chloride, benzethonium chloride, chlorhexidine gluconate, alkyl polyaminoethyl glycine, and sorbic acid.

The pH regulating agent includes, for example, hydrochloric acid, sulfuric acid, acetic acid, lactic acid, citric acid, tartaric acid, malic acid, phosphoric acid, boric acid, sodium hydroxide, potassium hydroxide, calcium hydroxide, monoethanolamine, diethanolamine, diethylamine, ammonia and salts thereof.

The tonicity agent includes, for example, sodium chloride, potassium chloride, calcium chloride, and mannitol.

As the solvent used in a fluid containing at least one kind of biologically ingestible microparticle material in the present invention, water such as ultrapure water and ion-exchange water, a water-miscible organic solvent such as methyl alcohol, ethyl alcohol, acetone, dimethylformamide, dimethylacetamide and dimethylsulfoxide, and a water-immiscible organic solvent such as octane, cyclohexane, benzene, xylene, diethyl ether and ethyl acetate can be appropriately selected depending on the object.

The biologically ingestible microparticles of the present invention are not particularly limited as long as they are intended to be ingested by the living body. Examples of such microparticles include: those which, like drugs in pharmaceutical preparations, are intended to be absorbed into the living body to exhibit their effect in the living body; those which, like barium sulfate as a contrast medium, pass through the living body; carrier substances of a chemical component in a drug delivery system; those which, like cosmetics, are applied to a skin of the living body; and intermediates between foods and the above substances.

The separating reaction of microparticles occurs by forced uniform mixing between the processing surfaces 1 and 2 arranged to be opposite to each other so as to be able to approach to and separate from each other, at least one of which rotates relative to the other, in the apparatus shown in FIG. 1(A).

First, a solution containing the first solvent is introduced through one flow path, that is, the first introduction part d1 into the space between the processing surfaces 1 and 2 arranged to be opposite to each other so as to be able to approach to and separate from each other, at least one of which rotates relative to the other, thereby forming a thin film fluid out of the first fluid between the processing surfaces.

Then, a solvent capable of serving as the second solvent in which the intended material has lower solubility than in the first solvent is introduced directly through another flow path, that is, the second introduction part d2 into the thin film fluid out of the first fluid produced between the processing surfaces 1 and 2.

As described above, the first solvent-containing solution and the second solvent are mixed in the space between the processing surfaces 1 and 2, the distance of which is regulated by the pressure balance between the supply pressure of the fluid and the pressure exerted between the rotating processing surfaces 1 and 2, thereby effecting the separating reaction of microparticles.

To effect the reaction between the processing surfaces 1 and 2, the second fluid may be introduced through the first introduction part d1 and the first fluid through the second introduction part d2 (this applies to the Examples that follow), as opposed to the above description. That is, the expression "first" or "second" for each solvent has a meaning for merely discriminating an $n^{th}$ solvent among a plurality of solvents present, and a third or more solvents can also be present.

As described above, the processing apparatus can be provided with a third introduction part d3 in addition to the first introduction part d1 and the second introduction part d2. In this case, the first solvent-containing solution, the second solvent, and a solution containing a stabilizer/dispersant can be introduced separately through the respective introduction parts into the processing apparatus. By doing so, the concentration and pressure of each solution can be controlled separately, and the separating reaction can be regulated more accurately. When the processing apparatus is provided with four or more introduction parts, the foregoing applies and fluids to be introduced into the processing apparatus can be subdivided in this manner.

Then, the method of separating biologically ingestible microparticles by neutralization reaction or by pH change is described. The following method is characterized in that when biologically ingestible microparticles are produced by separating biologically ingestible microparticle materials in a fluid by neutralization reaction or pH change, the fluid is formed into a thin film fluid generated between the processing surfaces arranged to be opposite to each other so as to be able to approach to and separate from each other, at least one of which rotates relative to the other, thereby separating biologically ingestible microparticles by neutralization reaction or pH change.

Hereinafter, specific examples of the present invention are described in more detail with reference to examples of biologically ingestible barium sulfate microparticles ingested as a contrast medium into the living body. However, the present invention is not limited to these examples.

This reaction occurs by forced uniform mixing between the processing surfaces 1 and 2 arranged to be opposite to each other so as to be able to approach to and separate from each other, at least one of which rotates relative to the other, in the apparatus shown in FIG. 1(A).

First, a fluid containing at least one kind of solution of a water-soluble barium salt such as barium chloride, barium hydroxide or barium acetate is introduced as a first fluid through one flow path, that is, the first introduction part d1 into the space between the processing surfaces 1 and 2 arranged to be opposite to each other so as to be able to approach to and separate from each other, at least one of which rotates relative to the other, thereby forming a thin film fluid out of the first fluid between the processing surfaces.

Then, a fluid containing at least one kind of water-soluble sulfuric acid compound solution such as sulfuric acid or ammonium sulfate is introduced as a second fluid directly through another flow path, that is, the second introduction part d2 into the thin film fluid out of the first fluid produced between the processing surfaces 1 and 2.

As described above, the first fluid and the second fluid are allowed to join together in a thin film fluid formed between the processing surfaces 1 and 2, the distance of which is regulated by the pressure balance between the supply pressure of the fluid and the pressure exerted between the rotating processing surfaces. The first fluid and the second fluid are mixed in the thin film fluid, and the two substances are reacted. Specifically, the reaction of forming biologically ingestible barium sulfate microparticles can be carried out by neutralization reaction or by pH change.

Then, a method of obtaining biologically ingestible microparticles other than barium sulfate is described.

Here, the simplest chemical reaction formula (Ion reaction formula) related to separation of barium sulfate exemplified above is as follows.

(Ionic Reaction Formula)

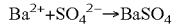

$$Ba^{2+} + SO_4^{2-} \rightarrow BaSO_4$$

The neutralization reaction in the present invention includes a neutralization reaction as the most fundamental acid-base reaction, that is, a neutralization reaction of negating the properties of both acid and base and simultaneously forming water and a salt, and a reaction wherein in the above ionic reaction formula, the cationic substance $Ba^{2+}$ and the anionic substance $SO_4^{2-}$ are reacted with each other to form the substance such as $BaSO_4$. The acid and base in this case may be those defined by Arrhenius, Broensted-Lowry, or Lewis.

Herein, the objective substance can be changed and obtained by changing the cationic or anionic substance to be used. The cationic or anionic substance is not particularly limited and may be a single atom ion such as $Na^+$ or $Cl^-$, or a polyatomic ion such as $NH^{4+}$ or $CH_3COO^-$. The objective substance may also be a complex ion. Organic matters whose structure is partially ionized in solution as often observed particularly in medical drugs can also be used.

Both the first and second fluids may contain the same ion.

When the neutralization reaction is carried out, the reaction may be accompanied by change in solvent pH.

The particle size, monodispersity or crystal form of the biologically ingestible microparticles obtained in the present invention can be regulated by changing the number of revolutions of the processing surfaces 1 and 2, the distance between the processing surfaces 1 and 2, the flow rate and temperature of the thin film fluid, and the concentration of the starting materials.

The biologically ingestible microparticles obtained in the present invention have desired particle size distribution/particle diameter distribution, the degree of crystallinity is 50% or more based on the total mass of the obtained particles, and a fluid containing the particles is a stable dispersion over hours, free of coagulating sedimentation or particle aggregation after preparation. The distance between the processing surfaces arranged to be opposite to each other can be freely regulated, so the particle diameter can be controlled, and at least one of the processing surfaces can rotate relative to the other, thereby controlling the crystal form freely.

The dispersion obtained by the present invention is stable, and this dispersion is comprised of a liquid dispersing medium and the biologically ingestible microparticles. A pharmaceutical composition can be obtained by mixing a pharmaceutically acceptable carrier in the biologically ingestible microparticles or a dispersion containing the particles of the present invention.

When this dispersion is used as a suspended ophthalmic solution as shown in examples below, the solution in which the intended drug is not dissolved shall be used and has preferably pH 3 to pH 9, more preferably pH 3.0 to pH 6.5, depending on physical properties of the drug. A pH value outside this range is not preferable because of high stimulation on the eye.

It is preferable that 90% of the obtained biologically ingestible microparticles in particle size distribution/particle diameter distribution have a particle size of 500 nm or less (that is, those particles having a particle diameter larger than 500 nm account for less than 10% of the particles). When 90% of the microparticles in particle size distribution/particle diameter distribution have a particle size of 500 nm or less, coarse particles serve as cores to prevent the phenomenon of aggregation, so that the surface area is increased and the apparent solubility is increased, and therefore, the corneal permeability of the active ingredient in the suspended ophthalmic solution is improved.

From the viewpoint of filtration sterilization, 90% of the particles in a suspended ophthalmic solution in particle size distribution/particle diameter distribution have a particle size of preferably 220 nm or less, whereby the solution can be sterilized by filtration and can be sterilized more inexpensively than in the conventional art.

The filtration sterilization filter that can be used may be any filter made of various materials as long as it is a commercial filter assured to be aseptic. Its materials include, for example, cellulose acetate, polycarbonate, polyvinylidene fluoride (PVDF), and the like.

The pore size of the filter is preferably 0.45 μm or less, and more preferably 0.22 μm or less. In the case of particle size distribution/particle diameter distribution higher than the above range, the filtration filter may be undesirably clogged and the yield may be undesirably decreased.

The dispersion stability of the suspended ophthalmic solution in the present invention can be improved by adding a surfactant and/or a water-soluble polymer to regulate the absolute value of zeta potential of the drug particles in the range of 20 mV to 150 mV. The amount of the surfactant/water-soluble polymer used in regulation of zeta potential varies depending on pH, but is preferably in the range of 0.05% to 3% in the suspended ophthalmic solution.

In this manner, an aqueous dispersion (suspension) in which biologically ingestible microparticles having an average primary particle size of 0.5 nm to 10000 nm, preferably 1 nm to 500 nm, more preferably 30 nm to 200 nm have been dispersed can be prepared. When the dispersant is added to a solution containing biologically ingestible microparticle materials, an aqueous dispersion (suspension) in which biologically ingestible microparticles coordinated thereon with the dispersant have been dispersed can be prepared, and the obtained biologically ingestible microparticles are made very excellent in re-dispersibility. Because contamination in the production process is low and the degree of crystallization can be highly controlled in separating crystals, this production method is particularly convenient for obtaining biologically ingestible microparticles which, like pharmaceuticals and cosmetics, are intended to be ingested into the living body.

The "particle size" used in this specification refers to an average particle size determined by usual particle size measuring methods known in the art such as a dynamic light scattering method/laser diffraction method.

The effective dose level of the treatment drug is an effective dose for obtaining a desired therapeutic response to a specific administered composition and method. Accordingly, the selected dose level depends on a specific drug, a desired therapeutic effect, administration route, desired treatment duration, and other factors. As described above, the pharmaceutical composition of the present invention exhibits a surprisingly high in vivo absorption ratio which will be described specifically in Examples below and is extremely useful.

The pharmaceutical composition of the present invention is considered particularly useful in oral and parenteral administration methods including intravenous injection. It is anticipated that water-sparingly-soluble drugs which could not be intravenously injected in a conventional way can be administered safely according to the present invention. Drugs which could not be orally administered due to poor bioavailability can be effectively administered according to the present invention.

EXAMPLES

Hereinafter, the present invention is described in detail with reference to Examples, but the present invention is not limited only to Examples.

In the following examples, the term "from the center" means "through the first introduction part d1" in the processing apparatus shown in FIG. 1(A), the first fluid refers to the first processed fluid, and the second fluid refers to the second processed fluid introduced "through the second introduction part d2" in the processing apparatus shown in FIG. 1(A).

Example 1

Production of Danazol Particles

A mixed solution of an aqueous solution having the drug dissolved therein, a solution having low solubility for the drug, and a polymer dispersant or a stabilizer are mixed and subjected to crystallization reaction in a thin film fluid formed between the processing surfaces 1 and 2 arranged to be opposite to each other so as to be able to approach to and separate from each other, at least one of which rotates relative to the other, in the uniformly dispersing, stirring and mixing reaction apparatus shown in FIG. 1(A).

While 0.1% aqueous solution of Tween 80 was sent as a first fluid from the center at a supply pressure/back pressure of 0.02 MPa/0.01 MPa, at a revolution number of 1000 rpm and at a sending solution temperature of 35° C., a solution prepared by dissolving powdery danazol in ethanol was introduced at a rate of 10 ml/min. as a second fluid into the space between the processing surfaces. The first and second fluids were mixed with each other in the thin film fluid, and a danazol dispersion solution was discharged at a rate of 30 g/min. from the processing surfaces.

When the recovered danazol dispersion solution was measured with a particle size distribution measuring instrument utilizing a dynamic light scattering method as measurement principle (trade name: Microtrac UPA150, manufactured by Nikkiso Co., Ltd.), the volume average particle size was 65 nm and the CV value of its particle size distribution/particle diameter distribution was 170. The recovered danazol dispersion solution was dissolved with ethanol, and when its contamination with foreign substance was confirmed with a particle counter (trade name: Particle Counter KS65, manufactured by Rion Co., Ltd.), there were 13 particles having a size of 10 μm or more and 1 particle having a size of 25 μm or more per mL (0.05% danazol solution).

Then, the recovered danazol dispersion solution was dried, and its substance when identified with an X-ray diffraction/differential scanning calorimeter (DSC) and a Fourier transform infrared spectroscopy (FT-IR) instrument coincided with the danazol bulk powder and showed a crystallinity degree of 80%.

When the microparticles (volume average particle size 65 nm) of the present invention described above were administered as a nano suspension into a dog, the bioavailability (BA) thereof was 92.9%. Because the bioavailability (BA) of a commercial product (volume average particle size 10 μm) administered as a suspension was 5.1%, it can be said that the in vivo absorption ratio significantly improved.

The energy quantity required for atomization was 1/32000 as compared with that required for pulverization with a pulverizing machine SS5-100 manufactured by the present applicant.

Then, the conditions were changed as follows. While 0.1% aqueous solution of Tween 80 was sent as a first fluid from the center at a supply pressure/back pressure of 0.10 MPa/0.02 MPa, at a revolution number of 1000 rpm and at a sending solution temperature of 35° C., a solution prepared by dissolving powdery danazol in ethanol was introduced at a rate of 10 ml/min. as a second fluid into the space between the processing surfaces. The first and second fluids were mixed with each other in the thin film fluid, and a danazol dispersion solution was discharged at a rate of 70 g/min. from the processing surfaces.

When the recovered danazol dispersion solution was measured with a particle size distribution measuring instrument utilizing a dynamic light scattering method as measurement principle (trade name: Microtrac UPA150, manufactured by Nikkiso Co., Ltd.), the volume average particle size was 135 nm and the CV value of its particle size distribution/particle diameter distribution was 19%.

Then, the recovered danazol dispersion solution was dried, and its substance when identified with an X-ray diffraction/differential scanning calorimeter (DSC) and a Fourier transform infrared spectroscopy (FT-IR) instrument coincided with the danazol bulk powder and showed a crystallinity degree of 75%.

The conditions were further changed as follows. While water was sent as a first fluid from the center at a supply pressure/back pressure of 0.02 MPa/0.01 MPa, at a revolution number of 1000 rpm and at a sending solution temperature of 35° C., a solution prepared by dissolving powdery danazol in Tween 80-admixed ethanol was introduced at a rate of 10 ml/min. as a second fluid into the space between the processing surfaces. The first and second fluids were mixed with each other in the thin film fluid, and a danazol dispersion solution was discharged at a rate of 30 g/min. from the processing surfaces.

When the recovered danazol dispersion solution was measured with a particle size distribution measuring instrument utilizing a dynamic light scattering method as measurement principle (trade name: Microtrac UPA150, manufactured by Nikkiso Co., Ltd.), the volume average particle size was 78 nm and the CV value of its particle size distribution/particle diameter distribution was 18%.

Then, the recovered danazol dispersion solution was dried, and its substance when identified with an X-ray diffraction/differential scanning calorimeter (DSC) and a Fourier transform infrared spectroscopy (FT-IR) instrument coincided with the danazol bulk powder and showed a crystallinity degree of 82%.

Example 2

Production of Tacrolimus Hydrate Particles

While 0.1% aqueous solution of Tween 80 was sent as a first fluid from the center at a supply pressure/back pressure of 0.02 MPa/0.01 MPa, at a revolution number of 2000 rpm and at a sending solution temperature of 30° C., a solution prepared by dissolving tacrolimus hydrate in ethanol was introduced at a rate of 10 ml/min. as a second fluid into the space between the processing surfaces. The first and second fluids were mixed with each other in the thin film fluid, and a tacrolimus hydrate dispersion solution was discharged at a rate of 30 g/min. from the processing surfaces.

When the recovered tacrolimus hydrate dispersion solution was measured with a particle size distribution measuring instrument utilizing a dynamic light scattering method as measurement principle (trade name: Microtrac UPA150, manufactured by Nikkiso Co., Ltd.), the volume average particle size was 116 nm and the CV value of its particle size distribution/particle diameter distribution was 16%.

Then, the recovered tacrolimus hydrate dispersion solution was dried, and its substance when identified with an X-ray diffraction/differential scanning calorimeter (DSC) and a Fourier transform infrared spectroscopy (FT-IR) instrument coincided with the tacrolimus bulk powder and showed a crystallinity degree of 90%.

Then, the conditions were changed as follows. While 0.1% aqueous solution of Tween 80 was sent as a first fluid from the center at a supply pressure/back pressure of 0.02 MPa/0.01 MPa, at a revolution number of 1000 rpm and at a sending solution temperature of 30° C., a solution prepared by dissolving tacrolimus hydrate in ethanol was introduced at a rate of 10 ml/min. as a second fluid into the space between the processing surfaces. The first and second fluids were mixed with each other in the thin film fluid, and a tacrolimus hydrate dispersion solution was discharged at a rate of 20 g/min. from the processing surfaces.

When the recovered tacrolimus hydrate dispersion solution was measured with a particle size distribution measuring instrument utilizing a dynamic light scattering method as measurement principle (trade name: Microtrac UPA150, manufactured by Nikkiso Co., Ltd.), the volume average particle size was 98 nm and the CV value of its particle size distribution/particle diameter distribution was 13%.

Then, the recovered tacrolimus hydrate dispersion solution was dried, and its substance when identified with an X-ray diffraction/differential scanning calorimeter (DSC) and a Fourier transform infrared spectroscopy (FT-IR) instrument coincided with the tacrolimus bulk powder and showed a crystallinity degree of 95%.

Example 3

Production of Tranilast Particles

While water was sent as a first fluid from the center at a supply pressure/back pressure of 0.02 MPa/0.01 MPa, at a revolution number of 1000 rpm and at a sending solution temperature of 27° C., a solution prepared by dissolving tranilast in a Tween 80-containing potassium hydroxide solution, pH 13 was introduced at a rate of 10 ml/min. as a second fluid into the space between the processing surfaces. The first and second fluids were mixed with each other in the thin film fluid, and a tranilast dispersion solution was discharged at a rate of 30 g/min. from the processing surfaces.

When the recovered tranilast dispersion solution was measured with a particle size distribution measuring instrument utilizing a dynamic light scattering method as measurement principle (trade name: Microtrac UPA150, manufactured by Nikkiso Co., Ltd.), the volume average particle size was 120 nm and the CV value of its particle size distribution/particle diameter distribution was 15%.

Then, the recovered tranilast dispersion solution was dialyzed with a cellulose dialysis tube against purified water to remove the salt and then dried, and its substance when identified with an X-ray diffraction/differential scanning calorimeter (DSC) and a Fourier trans form infrared spectroscopy (FT-IR) instrument coincided with the tranilast bulk powder and showed a crystallinity degree of 86%.

When the microparticles (volume average particle size 120 nm) of the present invention described above were formed into an O/W cream preparation and examined in a skin permeability test for 8 hours with a test skin (LSE-high), it showed 5-fold permeability as compared with the bulk powder (volume average particle size 45 µm).

Examples 4 to 7

Separation of Barium Sulfate Particles

An aqueous solution of barium chloride and an aqueous solution of sodium sulfate are subjected to neutralization reaction in a thin film fluid formed between the processing surfaces 1 and 2 arranged to be opposite to each other so as to be able to approach to and separate from each other, at least one of which rotates relative to the other, in the uniformly dispersing, stirring and mixing reaction apparatus as shown in FIG. 1(A), thereby separating barium sulfate.

Example 4

While 25% sodium sulfate aqueous solution was sent as a first fluid from the center at a supply pressure/back pressure of 0.02 MPa/0.01 MPa, at a revolution number of 500 rpm and at a sending solution temperature of 25° C., 17% barium chloride aqueous solution was introduced at a rate of 10 ml/min. as a second fluid into the space between the processing surfaces. The first and second fluids were mixed with each other in the thin film fluid, and a barium sulfate dispersion solution was discharged at a rate of 20 g/min. from the processing surfaces.

Then, impurities were removed from this dispersion by a dialysis tube, and barium sulfate microparticles in this dispersion were observed with a transmission electron microscope (TEM). Randomly, 100 particles were selected therefrom, and their measured average primary particle size was 50 nm.

Further, the barium sulfate dispersion solution was vacuum-freeze dried to give powdery barium sulfate microscopes which were then introduced again into ion-exchange water and stirred with a high-speed stirring dispersing machine (trade name: CLEARMIX manufactured by M Technique Co., Ltd.), whereby a barium sulfate dispersion solution was obtained again, its average particle size was 50 nm which was the same as that of the barium sulfate dispersion before vacuum-freeze drying, and the resulting barium sulfate microparticle powders were thus confirmed to be excellent in re-dispersibility.

In Examples 5 to 7, the same sodium sulfate aqueous solution and barium chloride aqueous solution as in Example 1 were used to obtain a barium sulfate particle dispersion solution and barium sulfate powder by changing the number of revolutions, supply pressure and back pressure.

Comparative Example 1

The sodium sulfate aqueous solution was added to the barium chloride aqueous solution under stirring with CLEARMIX (manufactured by M Technique Co., Ltd.) to form a barium sulfate microparticle dispersion. At this time, the number of revolutions with CLEARMIX was 20000 rpm, and stirring was conducted for 30 minutes. A barium sulfate microparticle dispersion having an average primary particle size of 900 nm was obtained. When re-dispersibility was confirmed in the same manner as in Examples, the particle size became 1700 nm after re-dispersion, indicating stronger aggregation than before vacuum freeze drying. The results are shown in Table 1.

TABLE 1

| Example | First Fluid | Second Fluid | Number of Revolutions [rpm] | Supply Pressure [MPaG] | Back Pressure [MPaG] | Volume-Average Primary Particle Size [nm] | Re-dispersibility |
|---|---|---|---|---|---|---|---|
| 4 | 25% sodium sulfate aqueous solution | 17% barium chloride aqueous solution | 500 | 0.02 | 0.01 | 50 | ○ |
| 5 | | | | 0.04 | | 75 | ○ |
| 6 | | | 1000 | 0.04 | 0.01 | 40 | ○ |
| 7 | | | | | 0.05 | 30 | ○ |
| Comparative Example 1 | | | 20000 | — | — | 900 | x |

Examples 8 to 10

Production of Fluorometholone-Suspended Ophthalmic Solution

While 0.05% solution of Tween 80 was sent as a first fluid from the center at a revolution number of 100 to 1000 rpm and at a sending solution temperature of 25° C., a solution prepared by dissolving fluorometholone in pyridine was introduced as a second fluid into the space between the processing surfaces. The first and second fluids were mixed with each other in the thin film fluid, and a fluorometholone suspension was discharged from the processing surfaces. The recovered fluorometholone suspension was measured with a particle size distribution measuring instrument utilizing a dynamic light scattering method as measurement principle (trade name: Microtrac UPA150, manufactured by Nikkiso Co., Ltd.). The recovered fluorometholone suspension was dried, and its substance when identified with an X-ray diffraction/differential scanning calorimeter (DSC) and a Fourier transform infrared spectroscopy (FT-IR) instrument coincided with the fluorometholone bulk powder.

In Comparative Examples 2 and 3, on the other hand, fluorometholone bulk powder was preliminarily pulverized and dispersed at 20000 rpm for 30 min. with a homogenizer (CLEARMIX 2.2S manufactured by M Technique Co., Ltd.). In Comparative Example 2, the sample was thereafter further finely divided, atomized and dispersed with an ultrathin film high-speed rotary pulverizer (SS5-100 manufactured by M Technique Co., Ltd.). In Comparative Example 4, none of the treatment was conducted, and only the pH adjustment of the bulk powder was conducted. Then, the bulk powders subjected to the above treatment were dissolved to prepare a separated suspension. The processing conditions and the particle size distribution/particle diameter distribution measurement results are shown in Table 2.

TABLE 2

| | Example 8 | Example 9 | Example 10 | Comparative Example 2 | Comparative Example 3 | comparative Example 4 |
|---|---|---|---|---|---|---|
| Homogenizer processing | absent | absent | absent | present | present | absent |
| Ultrathin film high-speed rotary pulverizing processing | absent | Absent | absent | present | absent | absent |
| Mixing ratio of first fluid/second fluid | 4:1 | 2:1 | 2:1 | — | — | — |
| Discharge flow rate (mL/min) | 30 | 20 | 20 | — | — | — |
| Number of revolutions (rpm) Homogenizer/ultrathin film high-speed rotary pulverizing | 100 | 100 | 1000 | 20000/10000 | 20000/— | — |
| Final fluorometholone concentration | 0.08 | 0.05 | 0.05 | 0.05 | 0.05 | 0.05 |
| Median particle diameter (nm) | 218 | 186 | 96 | 1027 | 6287 | 33232 |
| 90% median diameter (nm) | 498 | 325 | 198 | 2479 | 20670 | 180815 |
| Amount of energy applied | $1.45 \times 10^{-6}$ | $1.45 \times 10^{-6}$ | $1.45 \times 10^{-3}$ | 47.20 | 0.90 | — |

<Confirmation of Aptitude for Filtering Sterilization>

The 6 test solutions in Examples 8 to 10 and Comparative Examples 2 to 4 were subjected to filtering sterilization treatment with a PVDF filter having 0.22 µm pores. The concentration of fluorometholone before and after filtering sterilization was measured by HPLC, and the yield during filtering sterilization was determined. The results are shown in Table 3.

TABLE 3

|  | Example 8 | Example 9 | Example 10 | Comparative Example 2 | Comparative Example 3 | comparative Example 4 |
|---|---|---|---|---|---|---|
| Concentration before filtration (%) | 0.0050 | 0.0052 | 0.0050 | 0.0051 | 0.0050 | 0.0051 |
| Concentration after filtration (%) | 0.0012 | 0.0046 | 0.0050 | not filterable | not filterable | not filterable |
| Yield (%) | 24.0 | 88.5 | 100.0 | — | — | — |

The yield with a PVDF filter having 0.45 µm pores is shown in Table 4.

TABLE 4

|  | Example 8 | Example 9 | Example 10 | Comparative Example 2 | Comparative Example 3 | comparative Example 4 |
|---|---|---|---|---|---|---|
| Concentration before filtration (%) | 0.0049 | 0.0052 | 0.0051 | 0.0051 | 0.0050 | 0.0051 |
| Concentration after filtration (%) | 0.0040 | 0.0052 | 0.0051 | not filterable | not filterable | not filterable |
| Yield (%) | 81.6 | 100.0 | 100.0 | — | — | — |

Examples 11 to 13

Production of Pirenoxine-Suspended Ophthalmic Solution

While 0.05 mol/L nitric acid aqueous solution was sent as a first fluid from the center at a revolution number of 100 to 1000 rpm and at a sending solution temperature of 25° C., a solution prepared by dissolving pirenoxine in 0.1 mol/L sodium hydroxide was introduced as a second fluid into the space between the processing surfaces. The first and second fluids were mixed with each other in the thin film fluid, and a pirenoxine suspension was discharged from the processing surfaces. The recovered pirenoxine suspension was dialyzed with a dialysis tube against purified water to remove byproducts and then measured with a particle size distribution measuring instrument utilizing a dynamic light scattering method as measurement principle (trade name: Microtrac UPA150, manufactured by Nikkiso Co., Ltd.). The recovered pirenoxine suspension was dried, and its substance when identified with an X-ray diffraction/differential scanning calorimeter (DSC) and a Fourier transform infrared spectroscopy (FT-IR) instrument coincided with the pirenoxine bulk powder.

In Comparative Examples 5 and 6, on the other hand, pirenoxine bulk powders were preliminarily pulverized and dispersed at 18000 rpm for 30 min. with a homogenizer (CLEARMIX 2.2S manufactured by M Technique Co., Ltd.). In Comparative Example 5, the sample was thereafter further finely divided, atomized and dispersed with an ultrathin film high-speed rotary pulverizer (SS5-100 manufactured by M Technique Co., Ltd.). In Comparative Example 7, none of the treatment was conducted, and only the pH adjustment of the bulk powder was conducted. Then, the bulk powders subjected to the above treatment were dissolved to prepare a separated suspension.

The processing conditions and the particle size distribution/particle diameter distribution measurement results are shown in Table 5.

TABLE 5

|  | Example 11 | Example 12 | Example 13 | Comparative Example 5 | Comparative Example 6 | Comparative Example 7 |
|---|---|---|---|---|---|---|
| Homogenizer processing | absent | absent | absent | present | present | Absent |
| Ultrathin film high-speed rotary pulverizing processing | absent | absent | absent | present | absent | absent |
| Mixing ratio of first fluid/second fluid | 4:1 | 2:1 | 2:1 | — | — | — |
| Number of revolutions (rpm) Homogenizer/ultrathin film high-speed rotary pulverizing | 100 | 100 | 1000 | 18000/10000 | 18000/— | — |
| Final pirenoxine concentration | 0.08 | 0.05 | 0.05 | 0.05 | 0.05 | 0.05 |
| Median particle diameter (nm) | 98 | 20 | 8 | 97 | 800 | 21970 |
| 90% median diameter (nm) | 186 | 105 | 89 | 198 | 5890 | 65860 |
| Amount of energy applied | $1.45 \times 10^{-6}$ | $1.45 \times 10^{-6}$ | $1.45 \times 10^{-3}$ | 46.96 | 0.66 | — |

The amount of applied energy necessary for atomization was $1/3.2\times10^7$ to $1/3.2\times10^4$ relative to that by the ultrathin film high-speed rotary pulverizer (SS5-100 manufactured by M Technique Co., Ltd.), thus indicating excellent energy efficiency.

In Examples 11 to 13, when pH was adjusted to 3.0 to 5.5, the average particle size was 8 nm to 98 nm, and 90% particle size was 89 nm to 186 nm.

<Photostability Test>

Each test solution, 10 mL, in Examples 11 to 13 and Comparative Examples 5 to 7 was placed in a glass transparent vial and irradiated with light from a 2000 Lux·hr light source in a photoirradiation testing machine. Each test solution in a vial was sampled with time, and the pirenoxine concentration was measured with HPLC, to evaluate the residual degree of pirenoxine (%). The results are shown in Table 6. The numerical values in the table are mean values in triplicate.

TABLE 6

| Number of days elapsed | Example 11 | Example 12 | Example 13 | Comparative Example 5 | Comparative Example 6 | Comparative Example 7 |
|---|---|---|---|---|---|---|
| 0 | 100.0 | 100.0 | 100.0 | 100.0 | 100.0 | 100.0 |
| 1 | 98.3 | 97.8 | 98.6 | 98.3 | 97.9 | 95.4 |
| 2 | 97.0 | 98.1 | 98.2 | 97.0 | 97.3 | 90.8 |
| 3 | 96.3 | 97.9 | 97.6 | 96.3 | 97.0 | 88.7 |
| 4 | 95.0 | 97.4 | 98.0 | 95.0 | 96.7 | 84.0 |
| 5 | 93.5 | 97.0 | 97.7 | 93.7 | 96.8 | 79.5 |
| 6 | 92.3 | 96.9 | 97.3 | 92.6 | 95.1 | 75.6 |
| 7 | 89.9 | 95.0 | 96.6 | 89.5 | 93.5 | 72.8 |
| 10 | 85.7 | 94.6 | 95.1 | 85.7 | 86.8 | 61.4 |
| 25 | 81.9 | 93.0 | 94.5 | 80.2 | 79.0 | 50.9 |

Mean value in triplicate

<Skin Permeability Test>

The cornea excised from Japanese domestic rabbit was fixed to a horizontal 2-chamber diffusion cell (effective area, 0.3 cm²; cell volume, 5 mL; temperature, 32° C.) such that the corneal epithelium was faced with the donor side. A reservoir liquid was a phosphate isotonic buffer, pH 7.5. Each test solution in Examples 11 to 13 and Comparative Examples 5 to 7 was used at the donor side. The time when each test solution was added to the donor side was time 0, and the reservoir liquid was sampled with time. The pirenoxine concentration in the sampled solution was measured with HPLC, and pirenoxine that had moved in the cornea was evaluated. The results are shown in Table 7. The numerical values in the table are mean values in triplicate.

TABLE 7

| Time (hr) | Example 11 | Example 12 | Example 13 | Comparative Example 5 | Comparative Example 6 | Comparative Example 7 |
|---|---|---|---|---|---|---|
| 0.0 | 0.0 | 0.0 | 0.0 | 0.0 | 0.0 | 0.0 |
| 0.5 | 0.0 | 0.0 | 0.0 | 0.0 | 0.0 | 0.0 |
| 1.0 | 4.2 | 13.4 | 14.6 | 4.5 | 0.0 | 0.0 |
| 1.5 | 36.7 | 56.7 | 58.8 | 35.7 | 3.8 | 0.0 |
| 2.0 | 85.9 | 102.8 | 112.6 | 85.9 | 34.7 | 18.3 |
| 3.0 | 128.6 | 179.6 | 198.0 | 123.8 | 64.8 | 26.8 |
| 6.0 | 405.6 | 530.5 | 584.2 | 412.8 | 286.7 | 38.9 |

Unit (ng/mL): mean value in triplicate

<Confirmation of Aptitude for Filtering Sterilization>

The 6 test solutions in Examples 11 to 13 and Comparative Examples 5 to 7 were subjected to filtering sterilization treatment with a PVDF filter having 0.22 μm pores. The concentration of pirenoxine before and after filtering sterilization was measured by HPLC, and the yield during filtering sterilization was determined. The results are shown in Table 8.

TABLE 8

|  | Example 11 | Example 12 | Example 13 | Comparative Example 5 | Comparative Example 6 | Comparative Example 7 |
|---|---|---|---|---|---|---|
| Concentration before filtration (%) | 0.0050 | 0.0052 | 0.0049 | 0.0052 | 0.0050 | 0.0051 |
| Concentration after filtration (%) | 0.0049 | 0.0052 | 0.0049 | 0.0051 | 0.0012 | not filterable |
| Yield (%) | 98.0 | 100.0 | 100.0 | 98.1 | 24.0 | — |

Example 14

Amount of Applied Energy

Fluorometholone-Suspended Ophthalmic Solution

In Example 14, when a first fluid that is 0.05% Tween 80 solution and a second fluid that is a solution of fluorometholone (solvent: acetone) were aseptically filtered with a 0.22 μm filter, then mixed at a revolution number of 100 rpm at a first fluid/second fluid ratio of 4/1 and discharged at a flow rate of 150 mL/min., powder having an average particle size of 2.2 μm was obtained. In the comparative example (Comparative Example 8), when the bulk powder was sterilized by dry heat and atomized with a homogenizer (18000 rpm for 30 min., CLEARMIX 2.2S manufactured by M Technique Co., Ltd.) and an ultrathin film high-speed rotary pulverizer (SS5-100 manufactured by M Technique Co., Ltd.), the average particle size was 2.1 μm. The amount of applied energy necessary for the method (Example 14) of the present invention was about 1/30000 as compared with that necessary in the comparative example (Comparative Example 8) described above.

The invention claimed is:

1. A method for producing biologically ingestible microparticles, comprising the steps of:
    providing a first processing surface and a second processing surface, the first processing surface and the second processing surface being arranged to be opposite to each other so as to be able to approach to and separate from each other, at least one of the first processing surface and the second processing surface rotating relative to the other;
    forming a flat surface and a plurality of grooves on the flat surface in the first processing surface, wherein a flow path limiting part constitutes the plurality of grooves, and wherein the flow path limiting part, the first processing surface and the second processing surface constitute a dynamical pressure generating mechanism, the plurality of grooves having a depth of 1 μm to 50 μm, which is arranged on the processing surface, the total area thereof in the horizontal direction being 5% to 50%, based on the whole of the processing surface, the number of grooves being 3 to 50, and the grooves extending in a curved or spiral form on the processing surface or bending at a right angle, having depth changing continuously;
    introducing a fluid to be processed between the first processing surface and the second processing surface;
    generating a moving force by a fluid pressure of the fluid in a direction of separating the second processing surface from the first processing surface;
    maintaining a distance between the first processing surface and the second processing by the moving force to form a minute space, wherein the fluid pressure contains dynamical pressure generated by the dynamical pressure generating mechanism due to the plurality of grooves, while the fluid to be processed is passed through the minute space between the first processing surface and the second processing surface, and wherein the minute space is maintained by the pressure of the fluid to be processed including the dynamical pressure;
    forming a thin film fluid by passing the fluid through the minute space between the first processing surface and the second processing surface; and
    separating biologically ingestible microparticles in the thin film fluid,
    wherein the fluid to be processed comprises at least two kinds of fluids, said at least two kinds of fluids including a first kind of fluid and a second kind of fluid, and
    wherein the method further comprises the steps of:
    passing the first kind of fluid through a first flow path into the minute space between the first processing surface and the second processing surface, forming the thin film fluid;
    providing a second flow path independent of the first flow path; and
    passing the second kind of fluid through the second flow path into the minute space between the first and second processing surfaces, whereby the first kind of fluid and the second kind of fluid are mixed in the thin film fluid,
    wherein the second flow path is inclined, with respect to the second processing surface, at an angle more than 0° and less than 90°,
    wherein the objective substance of the biologically ingestible microparticles is a drug selected from the group consisting of analgesic agents, anti-inflammatory agents, anthelmintic agents, antiarrhythmic agents, antibiotics, anticoagulants, antihypotensive drugs, antidiabetic agents, antiepileptic drugs, antihistaminic agents, anti-malignant tumor agents, anorectic drugs, anti-obesity drugs, antihypertensive agents, antimuscarinic drugs, antimycobacterial agents, antineoplastic agents, immunosuppressive agents, antithyroid agents, antibacterial agents, antiviral agents, anti-anxiety drugs, astringents, beta-adrenoreceptor blockers, blood preparations, plasma substitutes, myocardial inotropic agents, contrast media, corticosteroids, cough suppressants, diagnostic agents, diagnostic image-forming agents, diuretic agents, dopaminergic agents, hemostatic drugs, immunological agents, lipid regulatory agents, muscle relaxants, parasympathomimetic agents, parathyroid calcitonin, biphosphonates, prostaglandins, radioactive agents, sex hormones, antiallergic agents, stimulants, anorexigenic agents, sympathomimetics, thyroid agents, vasodilators and xanthines, cataract remedies, and adrenal corticosteroids.

2. The method for producing biologically ingestible microparticles according to claim 1, wherein
    either one of the first kind of fluid and the second kind of fluid has at least one kind of raw material of biologically ingestible microparticles dissolved in a first solvent, the other of the first kind of fluid or the second kind of fluid is a solvent capable of serving as a second solvent having lower solubility than that of the first solvent, whereby biologically ingestible microparticles are separated in the thin film fluid.

3. The method for producing biologically ingestible microparticles according to claim 1, wherein either one of the first kind of fluid and the second kind of fluid contains at least one acidic substance or cationic substance, the other of the first kind of fluid or the second kind of fluid contains at least one basic substance or anionic substance, whereby biologically ingestible microparticles are separated by a neutralization reaction in the thin film fluid.

4. The method for producing biologically ingestible microparticles according to claim 1, further comprising the steps of:

providing a fluid pressure imparting mechanism for imparting pressure to the fluid to be processed, providing at least two processing members of a first processing member and a second processing member, the second processing member being capable of approaching to and separating from the first processing member, and providing a rotation drive mechanism for rotating the first processing member and the second processing member relative to each other, wherein the first processing member is provided with the first processing surface and the second processing member is provided with the second processing surface disposed in a position facing the first processing surface, wherein each of the processing surfaces constitutes part of the first flow path through which the fluid to be processed under the pressure is passed, wherein, of the first and second processing members, at least the second processing member is provided with a pressure-receiving surface, and at least part of the pressure-receiving surface is comprised of the second processing surface, wherein the pressure-receiving surface receives pressure applied to the fluid to be processed by the fluid pressure imparting mechanism thereby generating a force to move in the direction of separating the second processing surface from the first processing surface, wherein the first kind of fluid under pressure imparted by the fluid pressure imparting mechanism is passed between the first and second processing surfaces being capable of approaching to and separating from each other and rotating relative to each other, whereby the first kind of fluid forms a thin film fluid while passing between both the processing surfaces; and the method for producing biologically ingestible microparticles further comprising the steps of:

providing at least one opening leading to the second flow path and being arranged in at least either the first processing surface or the second processing surface.

5. The method for producing biologically ingestible microparticles according to claim 1, wherein heat or warmth is added between the processing surfaces; ultraviolet ray (UV) is irradiated between the processing surfaces; or ultrasonic energy is supplied between the processing surfaces.

6. The method for producing biologically ingestible microparticles according to claim 1, wherein the producing method is conducted in a container capable of securing a depressurized or vacuum state, so as to form a depressurized or vacuum state of a side at which the fluid to be processed is discharged after processing, thereby removing a gas generated during the separation, removing a gas discharged from the processing member, or removing the solvent of the fluid.

7. The method for producing biologically ingestible microparticles according to claim 1, wherein at least one of the fluids to be processed comprises at least one kind selected from a dispersant, a water-soluble polymer, a stabilizer, a preservative, a pH regulating agent and a tonicity agent.

8. The method for producing biologically ingestible microparticles according to claim 1, wherein each of the fluids to be processed is subjected to aseptic filtration before or after the processing of the separation.

9. The method for producing biologically ingestible microparticles according to claim 2, further comprising the steps of:

providing a fluid pressure imparting mechanism for imparting pressure to the fluid to be processed, providing at least two processing members of a first processing member and a second processing member, the second processing member being capable of approaching to and separating from the first processing member, and providing a rotation drive mechanism for rotating the first processing member and the second processing member relative to each other, wherein the first processing member is provided with the first processing surface and the second processing member is provided with the second processing surface disposed in a position facing the first processing surface, wherein each of the processing surfaces constitutes part of the first flow path through which the fluid to be processed under the pressure is passed, wherein, of the first and second processing members, at least the second processing member is provided with a pressure-receiving surface, and at least part of the pressure-receiving surface is comprised of the second processing surface, wherein the pressure-receiving surface receives pressure applied to the fluid to be processed by the fluid pressure imparting mechanism thereby generating a force to move in the direction of separating the second processing surface from the first processing surface, wherein the first kind of fluid under pressure imparted by the fluid pressure imparting mechanism is passed between the first and second processing surfaces being capable of approaching to and separating from each other and rotating relative to each other, whereby the first kind of fluid forms a thin film fluid while passing between both the processing surfaces; and the method for producing biologically ingestible microparticles further comprising the steps of:

providing at least one opening leading to the second flow path and being arranged in at least either the first processing surface or the second processing surface.

10. The method for producing biologically ingestible microparticles according to claim 3, further comprising the steps of:

providing a fluid pressure imparting mechanism for imparting pressure to the fluid to be processed, providing at least two processing members of a first processing member and a second processing member, the second processing member being capable of approaching to and separating from the first processing member, and providing a rotation drive mechanism for rotating the first processing member and the second processing member relative to each other, wherein the first processing member is provided with the first processing surface and the second processing member is provided with the second processing surface disposed in a position facing the first processing surface, wherein each of the processing surfaces constitutes part of the first flow path through which the fluid to be processed under the pressure is passed, wherein, of the first and second processing members, at least the second processing member is provided with a pressure-receiving surface, and at least part of the pressure-receiving surface is comprised of the second processing surface, wherein the pressure-receiving surface receives pressure applied to the fluid to be processed by the fluid pressure imparting mechanism thereby generating a force to move in the direction of separating the second processing surface from the first processing surface, wherein the first kind of fluid under pressure imparted by the fluid pressure imparting mechanism is passed between the first and second processing surfaces being capable of approaching to and separating from each other and rotating relative to each other, whereby the first kind of fluid forms a thin film fluid while passing between both the processing surfaces; and the method for producing biologically ingestible microparticles further comprising the steps of:

providing at least one opening leading to the second flow path and being arranged in at least either the first processing surface or the second processing surface.

11. The method for producing biologically ingestible microparticles according to claim 2, wherein heat or warmth is added between the processing surfaces; ultraviolet ray (UV) is irradiated between the processing surfaces; or ultrasonic energy is supplied between the processing surfaces.

12. The method for producing biologically ingestible microparticles according to claim 3, wherein heat or warmth is added between the processing surfaces; ultraviolet ray (UV) is irradiated between the processing surfaces; or ultrasonic energy is supplied between the processing surfaces.

13. The method for producing biologically ingestible microparticles according to claim 4, wherein heat or warmth is added between the processing surfaces; ultraviolet ray (UV) is irradiated between the processing surfaces; or ultrasonic energy is supplied between the processing surfaces.

14. The method for producing biologically ingestible microparticles according to claim 4, wherein the opening is positioned downstream at a point where a direction of flow of the first kind of fluid is changed to a direction of flow of the spiral laminar flow formed between the both of processing surfaces.

15. The method for producing biologically ingestible microparticles according to claim 9, wherein the opening is positioned downstream at a point where a direction of flow of the first kind of fluid is changed to a direction of flow of the spiral laminar flow formed between the both of processing surfaces.

16. The method for producing biologically ingestible microparticles according to claim 10, wherein the opening is positioned downstream at a point where a direction of flow of the first kind of fluid is changed to a direction of flow of the spiral laminar flow formed between the both of processing surfaces.

17. The method for producing biologically ingestible microparticles according to claim 1, wherein the second flow path includes an opening formed in either the first processing surface or the second processing surface, and the second flow path is configured such that an introduction of the second kind of fluid through the opening into between the both processing surfaces is toward a direction that is angularly offset, in a rotation direction of either the first processing surface or the second processing surface, from a line which passes through a center rotation axis of either the first processing surface or the second processing surface and the opening.

* * * * *